(12) United States Patent
De Libero et al.

(10) Patent No.: US 11,702,459 B2
(45) Date of Patent: Jul. 18, 2023

(54) MR1 RESTRICTED T CELL RECEPTORS FOR CANCER IMMUNOTHERAPY

(71) Applicant: UNIVERSITÄT BASEL, Basel (CH)

(72) Inventors: Gennaro De Libero, Bottmingen (CH); Marco Lepore, Abingdon (GB); Lucia Mori, Bottmingen (CH)

(73) Assignee: UNIVERSITÄT BASEL, Basel (CH)

( * ) Notice: Subject to any disclaimer, the term of this patent is extended or adjusted under 35 U.S.C. 154(b) by 733 days.

(21) Appl. No.: 16/563,987

(22) Filed: Sep. 9, 2019

(65) Prior Publication Data

US 2019/0389926 A1    Dec. 26, 2019

Related U.S. Application Data

(63) Continuation-in-part of application No. PCT/EP2018/055620, filed on Mar. 7, 2018.

(30) Foreign Application Priority Data

| Mar. 7, 2017 | (EP) | .................................... 17159754 |
| Jul. 3, 2017 | (EP) | .................................... 17179309 |
| Sep. 12, 2018 | (EP) | .................................... 18194025 |

(51) Int. Cl.
| C07K 14/725 | (2006.01) |
| C12N 5/0783 | (2010.01) |
| G01N 1/30 | (2006.01) |
| G01N 33/569 | (2006.01) |
| C12N 5/09 | (2010.01) |
| C12N 15/85 | (2006.01) |
| A61K 35/17 | (2015.01) |
| A61P 35/00 | (2006.01) |

(52) U.S. Cl.
CPC .......... *C07K 14/7051* (2013.01); *A61K 35/17* (2013.01); *A61P 35/00* (2018.01); *C12N 5/0636* (2013.01); *C12N 5/0693* (2013.01); *C12N 15/85* (2013.01); *G01N 1/30* (2013.01); *G01N 33/56966* (2013.01); *C12N 2501/2302* (2013.01); *C12N 2501/2307* (2013.01); *C12N 2501/2315* (2013.01); *C12N 2502/1114* (2013.01); *C12N 2502/30* (2013.01)

(58) Field of Classification Search
None
See application file for complete search history.

(56) References Cited

FOREIGN PATENT DOCUMENTS

| EP | 2899269 | 7/2015 |
| WO | 2014/160030 | 10/2014 |

OTHER PUBLICATIONS

Janeway et al., Immunobiology, 5th Ed., Garland Science, pp. 106-108 and 260-263, (2001). (Year: 2001).*
Manning et al., Immunity, vol. 8, 413-425, Apr. 1998. (Year: 1998).*
Garcia et al., Cell, vol. 122, 333-336, Aug. 12, 2005. (Year: 2005).*
Portolano et al., J Immunol. Feb. 1, 1993;150(3):880-7. (Year: 1993).*
Woodsworth et al., Genome Medicine 2013, 5:98. (Year: 2013).*
Robins et al., Blood. 2009;114:4099-4107. (Year: 2009).*
Eun Jeong Won et al: "Clinical relevance of circulating mucosal-associated invariant T cell levels and their anti-cancer activity in patients with mucosal-associated cancer", Oncotarget, vol. 7, No. 46, Nov. 15, 2016, XP55469874, United States, ISSN: 1949-2553, DOI: 10.18632/oncotarget.11187 abstract.
Lars Kjer-Nielsen et al: "MR1 presents microbial vitamin B metabolites to MAIT cells", Nature, Oct. 10, 2012, XP055433997, ISSN: 0028-0836, DOI: 10.1038/nature11605.
Marco Lepore et al: "Functionally diverse human T cells recognize non-microbial antigens presented by MR1", ELIFE, vol. 6, May 18, 2017, XP055434063, DOI: 10.7554/eLife.24476.
Limain Ling et al.; "Circulating and tumor-infiltrating mucosal associated invariant T (MAIT) cells in colorectal cancer patients"; Scientific Reports, 2016, vol. 6, 20358 (10 pages).
Marco Lepore et al.; "Parallel T-cell cloning and deep sequencing of human MAIT cells reveal stable oligoclonal TCBB repertoire"; Nature Communications, 2014, vol. 5, 3866 (14 pages).

* cited by examiner

*Primary Examiner* — Zachary S Skelding
(74) *Attorney, Agent, or Firm* — JMB Davis Ben-David

(57) ABSTRACT

The invention relates to a method of isolating a T cell that expresses a T cell receptor capable of binding specifically to an antigen presented by a cancer cell in association with an MR1 molecule. The method comprises the steps of (a) providing a preparation of T cells, (b) contacting the preparation with cancer cells expressing MR1 protein; (c) isolating a T cell that is specifically reactive to said cancer cells. The invention further relates to a method of preparing a T cell preparation expressing select MR1 recognizing T cell receptors from transgene expression vectors, the use of such T cell preparations in treatment of cancer, and to collections of MR1 reactive T cell receptor encoding nucleic acids and cells.

16 Claims, 12 Drawing Sheets

Specification includes a Sequence Listing.

SEQUENCE LISTING

<160> NUMBER OF SEQ ID NOS: 102

<210> SEQ ID NO 1
<211> LENGTH: 280
<212> TYPE: PRT
<213> ORGANISM: Homo sapiens

<400> SEQUENCE: 1

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

```
Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                 85                  90                  95

Lys His Leu Ser Leu His Ile Val Pro Ser Gln Pro Gly Asp Ser Ala
            100                 105                 110

Val Tyr Phe Cys Ala Ala Gln Ile Tyr Asn Gln Gly Gly Lys Leu Ile
        115                 120                 125

Phe Gly Gln Gly Thr Glu Leu Ser Val Lys Pro Asn Ile Gln Asn Pro
130                 135                 140

Asp Pro Ala Val Tyr Gln Leu Arg Asp Ser Lys Ser Ser Asp Lys Ser
145                 150                 155                 160

Val Cys Leu Phe Thr Asp Phe Asp Ser Gln Thr Asn Val Ser Gln Ser
                165                 170                 175

Lys Asp Ser Asp Val Tyr Ile Thr Asp Lys Thr Val Leu Asp Met Arg
            180                 185                 190

Ser Met Asp Phe Lys Ser Asn Ser Ala Val Ala Trp Ser Asn Lys Ser
        195                 200                 205

Asp Phe Ala Cys Ala Asn Ala Phe Asn Asn Ser Ile Ile Pro Glu Asp
210                 215                 220

Thr Phe Phe Pro Ser Pro Glu Ser Ser Cys Asp Val Lys Leu Val Glu
225                 230                 235                 240

Lys Ser Phe Glu Thr Asp Thr Asn Leu Asn Phe Gln Asn Leu Ser Val
                245                 250                 255

Ile Gly Phe Arg Ile Leu Leu Leu Lys Val Ala Gly Phe Asn Leu Leu
            260                 265                 270

Met Thr Leu Arg Leu Trp Ser Ser
        275                 280

<210> SEQ ID NO 2
<211> LENGTH: 309
<212> TYPE: PRT
<213> ORGANISM: Homo sapiens

<400> SEQUENCE: 2

Met Gly Ile Arg Leu Leu Cys Arg Val Ala Phe Cys Phe Leu Ala Val
 1               5                  10                  15

Gly Leu Val Asp Val Lys Val Thr Gln Ser Ser Arg Tyr Leu Val Lys
                 20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
 50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
            100                 105                 110

Ser Phe Ser Gly Lys Gln Tyr Phe Gly Pro Gly Thr Arg Leu Thr
        115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160
```

```
Cys Leu Ala Thr Gly Phe Tyr Pro Asp His Val Glu Leu Ser Trp Trp
                165                 170                 175
Val Asn Gly Lys Glu Val His Ser Gly Val Ser Thr Asp Pro Gln Pro
            180                 185                 190
Leu Lys Glu Gln Pro Ala Leu Asn Asp Ser Arg Tyr Cys Leu Ser Ser
        195                 200                 205
Arg Leu Arg Val Ser Ala Thr Phe Trp Gln Asn Pro Arg Asn His Phe
    210                 215                 220
Arg Cys Gln Val Gln Phe Tyr Gly Leu Ser Glu Asn Asp Glu Trp Thr
225                 230                 235                 240
Gln Asp Arg Ala Lys Pro Val Thr Gln Ile Val Ser Ala Glu Ala Trp
                245                 250                 255
Gly Arg Ala Asp Cys Gly Phe Thr Ser Glu Ser Tyr Gln Gln Gly Val
            260                 265                 270
Leu Ser Ala Thr Ile Leu Tyr Glu Ile Leu Leu Gly Lys Ala Thr Leu
        275                 280                 285
Tyr Ala Val Leu Val Ser Ala Leu Val Leu Met Ala Met Val Lys Arg
    290                 295                 300
Lys Asp Ser Arg Gly
305

<210> SEQ ID NO 3
<211> LENGTH: 269
<212> TYPE: PRT
<213> ORGANISM: Homo sapiens

<400> SEQUENCE: 3

Met Ile Ser Leu Arg Val Leu Leu Val Ile Leu Trp Leu Gln Leu Ser
1               5                   10                  15
Trp Val Trp Ser Gln Arg Lys Glu Val Glu Gln Asp Pro Gly Pro Phe
                20                  25                  30
Asn Val Pro Glu Gly Ala Thr Val Ala Phe Asn Cys Thr Tyr Ser Asn
            35                  40                  45
Ser Ala Ser Gln Ser Phe Phe Trp Tyr Arg Gln Asp Cys Arg Lys Glu
        50                  55                  60
Pro Lys Leu Leu Met Ser Val Tyr Ser Ser Gly Asn Glu Asp Gly Arg
65                  70                  75                  80
Phe Thr Ala Gln Leu Asn Arg Ala Ser Gln Tyr Ile Ser Leu Leu Ile
                85                  90                  95
Arg Asp Ser Lys Leu Ser Asp Ser Ala Thr Tyr Leu Cys Val Val Thr
            100                 105                 110
Gly Asn Gln Phe Tyr Phe Gly Thr Gly Thr Ser Leu Thr Val Ile Pro
        115                 120                 125
Asn Ile Gln Asn Pro Asp Pro Ala Val Tyr Gln Leu Arg Asp Ser Lys
    130                 135                 140
Ser Ser Asp Lys Ser Val Cys Leu Phe Thr Asp Phe Asp Ser Gln Thr
145                 150                 155                 160
Asn Val Ser Gln Ser Lys Asp Ser Asp Val Tyr Ile Thr Asp Lys Thr
                165                 170                 175
Val Leu Asp Met Arg Ser Met Asp Phe Lys Ser Asn Ser Ala Val Ala
            180                 185                 190
Trp Ser Asn Lys Ser Asp Phe Ala Cys Ala Asn Ala Phe Asn Asn Ser
        195                 200                 205
Ile Ile Pro Glu Asp Thr Phe Phe Pro Ser Pro Glu Ser Ser Cys Asp
```

```
            210                 215                 220
Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Lys Val Ala
                245                 250                 255

Gly Phe Asn Leu Met Thr Leu Arg Leu Trp Ser Ser
                260                 265

<210> SEQ ID NO 4
<211> LENGTH: 313
<212> TYPE: PRT
<213> ORGANISM: Homo sapiens

<400> SEQUENCE: 4

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
                20                  25                  30

Lys Thr Gly Lys Arg Ile Met Leu Glu Cys Ser Gln Thr Lys Gly His
                35                  40                  45

Asp Arg Met Tyr Trp Tyr Arg Gln Asp Pro Gly Leu Gly Leu Arg Leu
50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
                100                 105                 110

Ser Asp Val Gly Thr Gly Asp Thr Gly Glu Leu Phe Phe Gly Glu Gly
                115                 120                 125

Ser Arg Leu Thr Val Leu Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
                195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
                260                 265                 270

Gln Gln Gly Val Leu Ser Ala Thr Ile Leu Tyr Glu Ile Leu Leu Gly
                275                 280                 285

Lys Ala Thr Leu Tyr Ala Val Leu Val Ser Ala Leu Val Leu Met Ala
                290                 295                 300

Met Val Lys Arg Lys Asp Ser Arg Gly
305                 310
```

```
<210> SEQ ID NO 5
<211> LENGTH: 277
<212> TYPE: PRT
<213> ORGANISM: Homo sapiens

<400> SEQUENCE: 5

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Glu Pro Ser Asn Thr Gly Lys Leu Ile Phe Gly Gln
        115                 120                 125

Gly Thr Thr Leu Gln Val Lys Pro Asp Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 6
<211> LENGTH: 313
<212> TYPE: PRT
<213> ORGANISM: Homo sapiens

<400> SEQUENCE: 6

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45
```

Glu Asn Met Phe Trp Tyr Arg Gln Asp Pro Gly Leu Gly Leu Arg Leu
 50                  55                  60
Ile Tyr Phe Ser Tyr Asp Val Lys Met Lys Glu Lys Gly Asp Ile Pro
 65                  70                  75                  80
Glu Gly Tyr Ser Val Ser Arg Glu Lys Lys Glu Arg Phe Ser Leu Ile
                 85                  90                  95
Leu Glu Ser Ala Ser Thr Asn Gln Thr Ser Met Tyr Leu Cys Ala Ser
                100                 105                 110
Ser Arg Leu Leu Ala Gly Gly Gln Asn Glu Gln Phe Phe Gly Pro Gly
            115                 120                 125
Thr Arg Leu Thr Val Leu Glu Asp Leu Lys Asn Val Phe Pro Pro Glu
130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Tyr Pro Asp His Val Glu
                165                 170                 175
Leu Ser Trp Trp Val Asn Gly Lys Glu Val His Ser Gly Val Ser Thr
            180                 185                 190
Asp Pro Gln Pro Leu Lys Glu Gln Pro Ala Leu Asn Asp Ser Arg Tyr
        195                 200                 205
Cys Leu Ser Ser Arg Leu Arg Val Ser Ala Thr Phe Trp Gln Asn Pro
210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Glu Ser Tyr
            260                 265                 270
Gln Gln Gly Val Leu Ser Ala Thr Ile Leu Tyr Glu Ile Leu Leu Gly
        275                 280                 285
Lys Ala Thr Leu Tyr Ala Val Leu Val Ser Ala Leu Val Leu Met Ala
290                 295                 300
Met Val Lys Arg Lys Asp Ser Arg Gly
305                 310

<210> SEQ ID NO 7
<211> LENGTH: 840
<212> TYPE: DNA
<213> ORGANISM: Homo sapiens

<400> SEQUENCE: 7
atggccatgc tcctgggggc atcagtgctg attctgtggc ttcagccaga ctgggtaaac     60
agtcaacaga agaatgatga ccagcaagtt aagcaaaatt caccatccct gagcgtccag    120
gaaggaagaa tttctattct gaactgtgac tatactaaca gcatgtttga ttatttccta    180
tggtacaaaa ataccctgc tgaaggtcct acattcctga tatctataag ttccattaag    240
gataaaaatg aagatggaag attcactgtc ttcttaaaca aaagtgccaa gcacctctct    300
ctgcacattg tgccctccca gcctggagac tctgcagtgt acttctgtgc agcccagatt    360
tataaccagg gaggaaagct tatcttcgga cagggaacgg agttatctgt gaaacccaat    420
atccagaacc ctgaccctgc cgtgtaccag ctgagagact ctaaatccag tgacaagtct    480
gtctgcctat tcaccgattt tgattctcaa acaaatgtgt cacaaagtaa ggattctgat    540
gtgtatatca cagacaaaac tgtgctagac atgaggtcta tggacttcaa gagcaacagt    600

```
gctgtggcct ggagcaacaa atctgacttt gcatgtgcaa acgccttcaa caacagcatt    660
attccagaag acaccttctt ccccagccca gaaagttcct gtgatgtcaa gctggtcgag    720
aaaagctttg aaacagatac gaacctaaac tttcaaaacc tgtcagtgat tgggttccga    780
atcctcctcc tgaaagtggc cgggtttaat ctgctcatga cgctgcggct gtggtccagc    840
```

```
<210> SEQ ID NO 8
<211> LENGTH: 927
<212> TYPE: DNA
<213> ORGANISM: Homo sapiens

<400> SEQUENCE: 8
atgggaatca ggctcctgtg tcgtgtggcc ttttgtttcc tggctgtagg cctcgtagat     60
gtgaaagtaa cccagagctc gagatatcta gtcaaaagga cgggagagaa agttttctg    120 gaatgtgtcc aggatatgga ccatgaaaat atgttctggt atcgacaaga cccaggtctg    180
gggctacggc tgatctattt ctcatatgat gttaaaatga agaaaaagg agatattcct    240 gagggtaca gtgtctctag agagaagaag gagcgcttct ccctgattct ggagtccgcc    300
agcaccaacc agacatctat gtacctctgt gccagcagtt tttctagcgg aaagcagtac    360
ttcgggccgg gcaccaggct cacggtcaca gaggacctga aaaacgtgtt cccacccgag    420
gtcgctgtgt ttgagccatc agaagcagag atctcccaca cccaaaaggc cacactggtg    480
tgcctggcca caggcttcta ccccgaccac gtggagctga ctggtgggt gaatgggaag    540 gaggtgcaca gtgggtcag cacagacccg cagcccctca aggagcagcc cgccctcaat    600
gactccagat actgcctgag cagccgcctg agggtctcgg ccaccttctg gcagaacccc    660
cgcaaccact ccgctgtca agtccagttc tacgggctct cggagaatga cgagtggacc    720
caggataggg ccaaacctgt cacccagatc gtcagcgccg aggcctgggg tagagcagac    780
tgtggcttca cctccgagtc ttaccagcaa ggggtcctgt ctgccaccat cctctatgag    840
atcttgctag ggaaggccac cttgtatgcc gtgctggtca gtgccctcgt gctgatggcc    900
atggtcaaga gaaaggattc cagaggc                                       927
```

```
<210> SEQ ID NO 9
<211> LENGTH: 807
<212> TYPE: DNA
<213> ORGANISM: Homo sapiens

<400> SEQUENCE: 9
atgatatcct tgagagtttt actggtgatc ctgtggcttc agttaagctg ggtttggagc     60
caacggaagg aggtggagca ggatcctgga cccttcaatg ttccagaggg agccactgtc    120
gctttcaact gtacttacag caacagtgct tctcagtctt tcttctggta cagacaggat    180
tgcaggaaag aacctaagtt gctgatgtcg gtatactcca gtggtaatga agatggaagg    240
tttacagcac agctcaatag agccagccag tatatttccc tgctcatcag agactccaag    300
ctcagtgatt cagccaccta cctctgtgtg gtgaccggta accagttcta ttttgggaca    360
gggacaagtt tgacggtcat tccaaatatc agaaccctg accctgccgt gtaccagctg    420
agagactcta atccagtgaa caagtctgtc tgcctattca ccgattttga ttctcaaaca    480
aatgtgtcac aaagtaagga ttctgatgtg tatatcacag acaaaactgt gctagacatg    540
aggtctatgg acttcaagag caacagtgct gtggcctgga gcaacaaatc tgactttgca    600
tgtgcaaacg ccttcaacaa cagcattatt ccagaagaca ccttcttccc cagcccagaa    660
agttcctgtg atgtcaagct ggtcgagaaa agctttgaaa cagatacgaa cctaaacttt    720
```

| | |
|---|---:|
| caaaacctgt cagtgattgg gttccgaatc ctcctcctga aagtggccgg gtttaatctg | 780 |
| ctcatgacgc tgcggctgtg gtccagc | 807 |

<210> SEQ ID NO 10
<211> LENGTH: 939
<212> TYPE: DNA
<213> ORGANISM: Homo sapiens

<400> SEQUENCE: 10

| | |
|---|---:|
| atggcctccc tgctcttctt ctgtggggcc ttttatctcc tgggaacagg gtccatggat | 60 |
| gctgatgtta cccagacccc aaggaatagg atcacaaaga caggaaagag gattatgctg | 120 |
| gaatgttctc agactaaggg tcatgataga atgtactggt atcgacaaga cccaggactg | 180 |
| ggcctacggt tgatctatta ctcctttgat gtcaaagata taaacaaagg agagatctct | 240 |
| gatggataca gtgtctctcg acaggcacag gctaaattct ccctgtccct agagtctgcc | 300 |
| atccccaacc agacagctct ttacttctgt gccaccagtg atgtcgggac aggggacacc | 360 |
| ggggagctgt ttttggaga aggctctagg ctgaccgtac tggaggacct gaaaaacgtg | 420 |
| ttcccacccg aggtcgctgt gtttgagcca tcagaagcag atctcccca cacccaaaag | 480 |
| gccacactgg tgtgcctggc acaggcttc taccccgacc acgtggagct gagctggtgg | 540 |
| gtgaatggga aggaggtgca cagtggggtc agcacagacc cgcagcccct caaggagcag | 600 |
| cccgccctca tgactccag atactgcctg agcagccgcc tgagggtctc ggccaccttc | 660 |
| tggcagaacc cccgcaacca cttccgctgt caagtccagt tctacgggct ctcggagaat | 720 |
| gacgagtgga cccaggatag gccaaacct gtcacccaga tcgtcagcgc cgaggcctgg | 780 |
| ggtagagcag actgtggctt cacctccgag tcttaccagc aaggggtcct gtctgccacc | 840 |
| atcctctatg agatcttgct agggaaggcc accttgtatg ccgtgctggt cagtgccctc | 900 |
| gtgctgatgg ccatggtcaa gagaaaggat tccagaggc | 939 |

<210> SEQ ID NO 11
<211> LENGTH: 831
<212> TYPE: DNA
<213> ORGANISM: Homo sapiens

<400> SEQUENCE: 11

| | |
|---|---:|
| atgctgactg ccagcctgtt gagggcagtc atagcctcca tctgtgttgt atccagcatg | 60 |
| gctcagaagg taactcaagc gcagactgaa atttctgtgg tggagaagga ggatgtgacc | 120 |
| ttggactgtg tgtatgaaac ccgtgatact acttattact tattctggta caagcaacca | 180 |
| ccaagtggag aattggtttt ccttattcgt cggaactctt ttgatgagca aaatgaaata | 240 |
| agtggtcggt attcttggaa cttcagaaa tccaccagtt ccttcaactt caccatcaca | 300 |
| gcctcacaag tcgtggactc agcagtatac ttctgtgctc tgagtgagga acctagcaac | 360 |
| acaggcaaac taatctttgg gcaagggaca actttacaag taaaaccaga tatccagaac | 420 |
| cctgacccctg ccgtgtacca gctgagagac tctaaatcca gtgacaagtc tgtctgccta | 480 |
| ttcaccgatt ttgattctca aacaaatgtg tcacaaagta aggattctga tgtgtatatc | 540 |
| acagacaaaa ctgtgctaga catgaggtct atggacttca gagcaacag tgctgtggcc | 600 |
| tggagcaaca aatctgactt tgcatgtgca aacgccttca caacagcat tattccagaa | 660 |
| gacaccttct tccccagccc agaaagttcc tgtgatgtca gctggtcga gaaagctttt | 720 |
| gaaacagata cgaacctaaa ctttcaaaac ctgtcagtga ttgggttccg aatcctcctc | 780 | ctgaaagtgg ccgggtttaa tctgctcatg acgctgcggc tgtggtccag c             831

<210> SEQ ID NO 12
<211> LENGTH: 939
<212> TYPE: DNA
<213> ORGANISM: Homo sapiens

<400> SEQUENCE: 12
atgggaatca ggctcctgtg tcgtgtggcc ttttgtttcc tggctgtagg cctcgtagat    60
gtgaaagtaa cccagagctc gagatatcta gtcaaaagga cgggagagaa agttttctg   120
gaatgtgtcc aggatatgga ccatgaaaat atgttctggt atcgacaaga cccaggtctg   180
gggctacggc tgatctattt ctcatatgat gttaaaatga agaaaaagg agatattcct    240
gaggggtaca gtgtctctag agagaagaag gagcgcttct ccctgattct ggagtccgcc   300
agcaccaacc agacatctat gtacctctgt gccagcagtc gactactagc ggggggggcag   360
aatgagcagt tcttcgggcc agggacacgg ctcaccgtgc tagaggacct gaaaaacgtg    420
ttcccacccg aggtcgctgt gtttgagcca tcagaagcag atctcccca cacccaaaag    480
gccacactgg tatgcctggc cacaggcttc taccccgacc acgtggagct gagctggtgg    540
gtgaatggga aggaggtgca cagtggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt cacctccgag tcttaccagc aagggtcct gtctgccacc    840
atcctctatg agatcttgct agggaaggcc accttgtatg ccgtgctggt cagtgccctc    900
gtgctgatgg ccatggtcaa gagaaaggat tccagaggc                          939

<210> SEQ ID NO 13
<211> LENGTH: 267
<212> TYPE: PRT
<213> ORGANISM: Homo sapiens

<400> SEQUENCE: 13

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Met Asp Ser Ser Tyr
            100                 105                 110

Lys Leu Ile Phe Gly Ser Gly Thr Arg Leu Leu Val Arg Pro Asp Ile
        115                 120                 125

Gln Asn Pro Asp Pro Ala Val Tyr Gln Leu Arg Asp Ser Lys Ser Ser
    130                 135                 140

Asp Lys Ser Val Cys Leu Phe Thr Asp Phe Asp Ser Gln Thr Asn Val
145                 150                 155                 160

```
Ser Gln Ser Lys Asp Ser Asp Val Tyr Ile Thr Asp Lys Thr Val Leu
            165                 170                 175
Asp Met Arg Ser Met Asp Phe Lys Ser Asn Ser Ala Val Ala Trp Ser
        180                 185                 190
Asn Lys Ser Asp Phe Ala Cys Ala Asn Ala Phe Asn Asn Ser Ile Ile
        195                 200                 205
Pro Glu Asp Thr Phe Phe Pro Ser Pro Glu Ser Ser Cys Asp Val Lys
        210                 215                 220
Leu Val Glu Lys Ser Phe Glu Thr Asp Thr Asn Leu Asn Phe Gln Asn
225                 230                 235                 240
Leu Ser Val Ile Gly Phe Arg Ile Leu Leu Leu Lys Val Ala Gly Phe
                245                 250                 255
Asn Leu Leu Met Thr Leu Arg Leu Trp Ser Ser
                260                 265

<210> SEQ ID NO 14
<211> LENGTH: 271
<212> TYPE: PRT
<213> ORGANISM: Homo sapiens

<400> SEQUENCE: 14

Met Leu Leu Ile Thr Ser Met Leu Val Leu Trp Met Gln Leu Ser Gln
1               5                   10                  15
Val Asn Gly Gln Gln Val Met Gln Ile Pro Gln Tyr Gln His Val Gln
                20                  25                  30
Glu Gly Glu Asp Phe Thr Thr Tyr Cys Asn Ser Ser Thr Thr Leu Ser
            35                  40                  45
Asn Ile Gln Trp Tyr Lys Gln Arg Pro Gly Gly His Pro Val Phe Leu
        50                  55                  60
Ile Gln Leu Val Lys Ser Gly Glu Val Lys Lys Gln Lys Arg Leu Thr
65                  70                  75                  80
Phe Gln Phe Gly Glu Ala Lys Lys Asn Ser Ser Leu His Ile Thr Ala
                85                  90                  95
Thr Gln Thr Thr Asp Val Gly Thr Tyr Phe Cys Ala Ala Ala Gly Gly
            100                 105                 110
Thr Ser Tyr Gly Lys Leu Thr Phe Gly Gln Gly Thr Ile Leu Thr Val
        115                 120                 125
His Pro Asn Ile Gln Asn Pro Asp Pro Ala Val Tyr Gln Leu Arg Asp
    130                 135                 140
Ser Lys Ser Ser Asp Lys Ser Val Cys Leu Phe Thr Asp Phe Asp Ser
145                 150                 155                 160
Gln Thr Asn Val Ser Gln Ser Lys Asp Ser Asp Val Tyr Ile Thr Asp
                165                 170                 175
Lys Thr Val Leu Asp Met Arg Ser Met Asp Phe Lys Ser Asn Ser Ala
            180                 185                 190
Val Ala Trp Ser Asn Lys Ser Asp Phe Ala Cys Ala Asn Ala Phe Asn
        195                 200                 205
Asn Ser Ile Ile Pro Glu Asp Thr Phe Phe Pro Ser Pro Glu Ser Ser
    210                 215                 220
Cys Asp Val Lys Leu Val Glu Lys Ser Phe Glu Thr Asp Thr Asn Leu
225                 230                 235                 240
Asn Phe Gln Asn Leu Ser Val Ile Gly Phe Arg Ile Leu Leu Leu Lys
                245                 250                 255
Val Ala Gly Phe Asn Leu Leu Met Thr Leu Arg Leu Trp Ser Ser
```

<210> SEQ ID NO 15
<211> LENGTH: 277
<212> TYPE: PRT
<213> ORGANISM: Homo sapiens

<400> SEQUENCE: 15

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Thr Trp Thr Asp Arg Gly Ser Thr Leu Gly Arg Leu Tyr Phe Gly Arg
        115                 120                 125

Gly Thr Gln Leu Thr Val Trp Pro Asp Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 16
<211> LENGTH: 280
<212> TYPE: PRT
<213> ORGANISM: Homo sapiens

<400> SEQUENCE: 16

Met Ala Met Leu Leu Gly Ala Ser Val Leu Ile Leu Trp Leu Gln Thr
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn

```
            35                  40                  45
Cys Asp Tyr Thr Asn Ser Met Phe Asp Tyr Phe Leu Trp Tyr Lys Lys
 50                  55                  60

Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                 85                  90                  95

Lys His Leu Ser Leu His Ile Val Pro Ser Gln Pro Gly Asp Ser Ala
            100                 105                 110

Val Tyr Phe Cys Ala Ala Ser Leu Tyr Asn Gln Gly Gly Lys Leu Ile
        115                 120                 125

Phe Gly Gln Gly Thr Glu Leu Ser Val Lys Pro Asn Ile Gln Asn Pro
130                 135                 140

Asp Pro Ala Val Tyr Gln Leu Arg Asp Ser Lys Ser Ser Asp Lys Ser
145                 150                 155                 160

Val Cys Leu Phe Thr Asp Phe Asp Ser Gln Thr Asn Val Ser Gln Ser
                165                 170                 175

Lys Asp Ser Asp Val Tyr Ile Thr Asp Lys Thr Val Leu Asp Met Arg
            180                 185                 190

Ser Met Asp Phe Lys Ser Asn Ser Ala Val Ala Trp Ser Asn Lys Ser
        195                 200                 205

Asp Phe Ala Cys Ala Asn Ala Phe Asn Asn Ser Ile Ile Pro Glu Asp
210                 215                 220

Thr Phe Phe Pro Ser Pro Glu Ser Ser Cys Asp Val Lys Leu Val Glu
225                 230                 235                 240

Lys Ser Phe Glu Thr Asp Thr Asn Leu Asn Phe Gln Asn Leu Ser Val
                245                 250                 255

Ile Gly Phe Arg Ile Leu Leu Leu Lys Val Ala Gly Phe Asn Leu Leu
            260                 265                 270

Met Thr Leu Arg Leu Trp Ser Ser
        275                 280

<210> SEQ ID NO 17
<211> LENGTH: 274
<212> TYPE: PRT
<213> ORGANISM: Homo sapiens

<400> SEQUENCE: 17

Met Glu Lys Asn Pro Leu Ala Ala Pro Leu Leu Ile Leu Trp Phe His
 1               5                  10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
 50                  55                  60

Ser Pro Glu Ala Leu Phe Val Met Thr Leu Asn Gly Asp Glu Lys Lys
 65                  70                  75                  80

Lys Gly Arg Ile Ser Ala Thr Leu Asn Thr Lys Glu Gly Tyr Ser Tyr
                 85                  90                  95

Leu Tyr Ile Lys Gly Ser Gln Pro Glu Asp Ser Ala Thr Tyr Leu Cys
            100                 105                 110

Ala Ser Gly Asp Ser Gly Tyr Ala Leu Asn Phe Gly Lys Gly Thr Ser
        115                 120                 125
```

```
Leu Leu Val Thr Pro His Ile Gln Asn Pro Asp Pro Ala Val Tyr Gln
        130                 135                 140

Leu Arg Asp Ser Lys Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 18
<211> LENGTH: 276
<212> TYPE: PRT
<213> ORGANISM: Homo sapiens

<400> SEQUENCE: 18

Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
                20                  25                  30

Ser Glu Glu Ala Phe Leu Thr Ile Asn Cys Thr Tyr Thr Ala Thr Gly
            35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Thr
            100                 105                 110

Ile Trp Asp Tyr Gly Gly Ser Gln Gly Asn Leu Ile Phe Gly Lys Gly
        115                 120                 125

Thr Lys Leu Ser Val Lys Pro Asn Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
                180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
    210                 215                 220
```

```
Ser Pro Glu Ser Ser Cys Asp Val Lys Leu Val Lys Ser Phe Glu
225                 230                 235                 240

Thr Asp Thr Asn Leu Asn Phe Gln Asn Leu Ser Val Ile Gly Phe Arg
            245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 19
<211> LENGTH: 269
<212> TYPE: PRT
<213> ORGANISM: Homo sapiens

<400> SEQUENCE: 19

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Glu Asn Ser
            100                 105                 110

Gly Tyr Ala Leu Asn Phe Gly Lys Gly Thr Ser Leu Leu Val Thr Pro
        115                 120                 125

His Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 20
<211> LENGTH: 275
<212> TYPE: PRT
<213> ORGANISM: Homo sapiens

<400> SEQUENCE: 20
```

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Leu Ser Gly Gly Ser Tyr Ile Pro Thr Phe Gly Arg Gly Thr
        115                 120                 125

Ser Leu Ile Val His Pro Tyr Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
    195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
            245                 250                 255

Leu Leu Leu Lys Val Ala Gly Phe Asn Leu Leu Met Thr Leu Arg Leu
        260                 265                 270

Trp Ser Ser
        275

<210> SEQ ID NO 21
<211> LENGTH: 275
<212> TYPE: PRT
<213> ORGANISM: Homo sapiens

<400> SEQUENCE: 21

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95
```

Ser Ile Pro Ser Asp Val Gly Ile Tyr Phe Cys Ala Gly Gln Leu Gly
            100                 105                 110

Gly Ala Gly Gly Thr Ser Tyr Gly Lys Leu Thr Phe Gly Gln Gly Thr
        115                 120                 125

Ile Leu Thr Val His Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 22
<211> LENGTH: 274
<212> TYPE: PRT
<213> ORGANISM: Homo sapiens

<400> SEQUENCE: 22

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Asn
            100                 105                 110

Trp Ser Pro Gln Gly Asn Glu Lys Leu Thr Phe Gly Thr Gly Thr Arg
        115                 120                 125

Leu Thr Ile Ile Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser

```
                    180                 185                 190
Asn Ser Ala Val Ala Trp Ser Asn Lys Ser Asp Phe Ala Cys Ala Asn
            195                 200                 205
Ala Phe Asn Asn Ser Ile Ile Pro Glu Asp Thr Phe Pro Ser Pro
        210                 215                 220
Glu Ser Ser Cys Asp Val Lys Leu Val Glu Lys Ser Phe Glu Thr Asp
225                 230                 235                 240
Thr Asn Leu Asn Phe Gln Asn Leu Ser Val Ile Gly Phe Arg Ile Leu
                245                 250                 255
Leu Leu Lys Val Ala Gly Phe Asn Leu Leu Met Thr Leu Arg Leu Trp
            260                 265                 270
Ser Ser

<210> SEQ ID NO 23
<211> LENGTH: 267
<212> TYPE: PRT
<213> ORGANISM: Homo sapiens

<400> SEQUENCE: 23

Met Trp Gly Val Phe Leu Leu Tyr Val Ser Met Lys Met Gly Gly Thr
1               5                   10                  15
Thr Gly Gln Asn Ile Asp Gln Pro Thr Glu Met Thr Ala Thr Glu Gly
            20                  25                  30
Ala Ile Val Gln Ile Asn Cys Thr Tyr Gln Thr Ser Gly Phe Asn Gly
        35                  40                  45
Leu Phe Trp Tyr Gln Gln His Ala Gly Glu Ala Pro Thr Phe Leu Ser
    50                  55                  60
Tyr Asn Val Leu Asp Gly Leu Glu Glu Lys Gly Arg Phe Ser Ser Phe
65                  70                  75                  80
Leu Ser Arg Ser Lys Gly Tyr Ser Tyr Leu Leu Leu Lys Glu Leu Gln
                85                  90                  95
Met Lys Asp Ser Ala Ser Tyr Leu Cys Ala Ser Met Asp Ser Asn Tyr
            100                 105                 110
Gln Leu Ile Trp Gly Ala Gly Thr Lys Leu Ile Ile Lys Pro Asp Ile
        115                 120                 125
Gln Asn Pro Asp Pro Ala Val Tyr Gln Leu Arg Asp Ser Lys Ser Ser
    130                 135                 140
Asp Lys Ser Val Cys Leu Phe Thr Asp Phe Asp Ser Gln Thr Asn Val
145                 150                 155                 160
Ser Gln Ser Lys Asp Ser Asp Val Tyr Ile Thr Asp Lys Thr Val Leu
                165                 170                 175
Asp Met Arg Ser Met Asp Phe Lys Ser Asn Ser Ala Val Ala Trp Ser
            180                 185                 190
Asn Lys Ser Asp Phe Ala Cys Ala Asn Ala Phe Asn Asn Ser Ile Ile
        195                 200                 205
Pro Glu Asp Thr Phe Phe Pro Ser Pro Glu Ser Ser Cys Asp Val Lys
    210                 215                 220
Leu Val Glu Lys Ser Phe Glu Thr Asp Thr Asn Leu Asn Phe Gln Asn
225                 230                 235                 240
Leu Ser Val Ile Gly Phe Arg Ile Leu Leu Leu Lys Val Ala Gly Phe
                245                 250                 255
Asn Leu Leu Met Thr Leu Arg Leu Trp Ser Ser
            260                 265
```

-continued

<210> SEQ ID NO 24
<211> LENGTH: 274
<212> TYPE: PRT
<213> ORGANISM: Homo sapiens

<400> SEQUENCE: 24

```
Met Ile Ser Leu Arg Val Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Arg Phe Thr Arg Asp Gly Asn Lys Leu Val Phe Gly Ala Gly Thr Ile
        115                 120                 125

Leu Arg Val Lys Ser Tyr Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 25
<211> LENGTH: 312
<212> TYPE: PRT
<213> ORGANISM: Homo sapiens

<400> SEQUENCE: 25

```
Met Ser Ile Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60
```

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Ser Glu Val Thr Gly Gly Tyr Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 26
<211> LENGTH: 311
<212> TYPE: PRT
<213> ORGANISM: Homo sapiens

<400> SEQUENCE: 26

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Ala
            100                 105                 110

Gly Gln Gly Pro Tyr Thr Asp Thr Gln Tyr Phe Gly Pro Gly Thr Arg

```
            115                 120                 125
Leu Thr Val Leu Glu Asp Leu Lys Asn Val Phe Pro Pro Glu Val Ala
130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
                180                 185                 190
Gln Pro Leu Lys Glu Gln Pro Ala Leu Asn Asp Ser Arg Tyr Cys Leu
                195                 200                 205
Ser Ser Arg Leu Arg Val Ser Ala Thr Phe Trp Gln Asn Pro Arg Asn
210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
                260                 265                 270
Gly Val Leu Ser Ala Thr Ile Leu Tyr Glu Ile Leu Leu Gly Lys Ala
                275                 280                 285
Thr Leu Tyr Ala Val Leu Val Ser Ala Leu Val Leu Met Ala Met Val
                290                 295                 300
Lys Arg Lys Asp Ser Arg Gly
305                 310

<210> SEQ ID NO 27
<211> LENGTH: 311
<212> TYPE: PRT
<213> ORGANISM: Homo sapiens

<400> SEQUENCE: 27

Met Gly Ile Arg Leu Leu Cys Arg Val Ala Phe Cys Phe Leu Ala Val
1               5                   10                  15
Gly Leu Val Asp Val Lys Val Thr Gln Ser Ser Arg Tyr Leu Val Lys
                20                  25                  30
Arg Thr Gly Glu Lys Val Phe Leu Glu Cys Val Gln Asp Met Asp His
                35                  40                  45
Glu Asn Met Phe Trp Tyr Arg Gln Asp Pro Gly Leu Gly Leu Arg Leu
50                  55                  60
Ile Tyr Phe Ser Tyr Asp Val Lys Met Lys Glu Lys Gly Asp Ile Pro
65                  70                  75                  80
Glu Gly Tyr Ser Val Ser Arg Glu Lys Lys Glu Arg Phe Ser Leu Ile
                85                  90                  95
Leu Glu Ser Ala Ser Thr Asn Gln Thr Ser Met Tyr Leu Cys Ala Ser
                100                 105                 110
Ser Leu Gly Ala Thr Gly Ala Asn Glu Lys Leu Phe Phe Gly Ser Gly
                115                 120                 125
Thr Gln Leu Ser Val Leu Glu Asp Leu Asn Lys Val Phe Pro Pro Glu
130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Phe Pro Asp His Val Glu
                165                 170                 175
```

-continued

Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
290                 295                 300

Met Val Lys Arg Lys Asp Phe
305                 310

<210> SEQ ID NO 28
<211> LENGTH: 308
<212> TYPE: PRT
<213> ORGANISM: Homo sapiens

<400> SEQUENCE: 28

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asp Tyr Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Tyr Arg Gly Thr Glu Ala Phe Phe Gly Gln Gly Thr Arg Leu
        115                 120                 125

Thr Val Val Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

```
Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 29
<211> LENGTH: 309
<212> TYPE: PRT
<213> ORGANISM: Homo sapiens

<400> SEQUENCE: 29

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln His Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Phe Asp Val Gly Leu Pro Pro Leu His Phe Gly Asn Gly Thr Arg
        115                 120                 125

Leu Thr Val Thr Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
```

```
                290                 295                 300

Lys Arg Lys Asp Phe
305

<210> SEQ ID NO 30
<211> LENGTH: 309
<212> TYPE: PRT
<213> ORGANISM: Homo sapiens

<400> SEQUENCE: 30

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Arg Glu Trp Glu Thr Gln Tyr Phe Gly Pro Gly Thr Arg Leu Leu
        115                 120                 125

Val Leu Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 31
<211> LENGTH: 315
<212> TYPE: PRT
<213> ORGANISM: Homo sapiens
```

<400> SEQUENCE: 31

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Gln Leu Tyr Arg Asp Thr Ser Asn Thr Gly Glu Leu Phe Phe Gly
        115                 120                 125

Glu Gly Ser Arg Leu Thr Val Leu Glu Asp Leu Lys Asn Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
    290                 295                 300

Met Ala Met Val Lys Arg Lys Asp Ser Arg Gly
305                 310                 315

<210> SEQ ID NO 32
<211> LENGTH: 313
<212> TYPE: PRT
<213> ORGANISM: Homo sapiens

<400> SEQUENCE: 32

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

```
Glu Tyr Met Ser Trp Tyr Arg Gln Asp Pro Gly Met Gly Leu Arg Leu
 50                  55                  60

Ile His Tyr Ser Val Gly Ala Gly Ile Thr Asp Gln Gly Glu Val Pro
 65                  70                  75                  80

Asn Gly Tyr Asn Val Ser Arg Ser Thr Thr Glu Asp Phe Pro Leu Arg
                 85                  90                  95

Leu Leu Ser Ala Ala Pro Ser Gln Thr Ser Val Tyr Phe Cys Ala Ser
                100                 105                 110

Gly Ile Ser Gly Thr Ala Ser Ser Tyr Asn Ser Pro Leu His Phe Gly
                115                 120                 125

Asn Gly Thr Arg Leu Thr Val Thr Glu Asp Leu Asn Lys Val Phe Pro
130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
                180                 185                 190

Ser Thr Asp Pro Gln Pro Leu Lys Glu Gln Pro Ala Leu Asn Asp Ser
                195                 200                 205

Arg Tyr Cys Leu Ser Ser Arg Leu Arg Val Ser Ala Thr Phe Trp Gln
210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
                260                 265                 270

Ser Tyr Gln Gln Gly Val Leu Ser Ala Thr Ile Leu Tyr Glu Ile Leu
                275                 280                 285

Leu Gly Lys Ala Thr Leu Tyr Ala Val Leu Val Ser Ala Leu Val Leu
                290                 295                 300

Met Ala Met Val Lys Arg Lys Asp Phe
305                 310
```

<210> SEQ ID NO 33
<211> LENGTH: 312
<212> TYPE: PRT
<213> ORGANISM: Homo sapiens

<400> SEQUENCE: 33

```
Met Gly Phe Arg Leu Leu Cys Cys Val Ala Phe Cys Leu Leu Gly Ala
1                   5                  10                  15

Gly Pro Val Asp Ser Gly Val Thr Gln Thr Pro Lys His Leu Ile Thr
                 20                  25                  30

Ala Thr Gly Gln Arg Val Thr Leu Arg Cys Ser Pro Arg Ser Gly Asp
                 35                  40                  45

Leu Ser Val Tyr Trp Tyr Gln Gln Ser Leu Asp Gln Gly Leu Gln Phe
 50                  55                  60

Leu Ile Gln Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                 85                  90                  95

Leu Ser Ser Leu Glu Leu Gly Asp Ser Ala Leu Tyr Phe Cys Ala Ser
                100                 105                 110
```

-continued

Ser Val Gly Gly Gly Leu Ala Asp Thr Gln Tyr Phe Gly Pro Gly Thr
            115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 34
<211> LENGTH: 311
<212> TYPE: PRT
<213> ORGANISM: Homo sapiens

<400> SEQUENCE: 34

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Glu Tyr Ile Gln Tyr Ser Gly Asn Thr Ile Tyr Phe Gly Glu Gly
        115                 120                 125

Ser Trp Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu

```
                165                 170                 175
Leu Ser Trp Trp Val Asn Gly Lys Glu Val His Ser Gly Val Ser Thr
            180                 185                 190
Asp Pro Gln Pro Leu Lys Glu Gln Pro Ala Leu Asn Asp Ser Arg Tyr
        195                 200                 205
Cys Leu Ser Ser Arg Leu Arg Val Ser Ala Thr Phe Trp Gln Asn Pro
    210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Val Ser Tyr
            260                 265                 270
Gln Gln Gly Val Leu Ser Ala Thr Ile Leu Tyr Glu Ile Leu Leu Gly
        275                 280                 285
Lys Ala Thr Leu Tyr Ala Val Leu Val Ser Ala Leu Val Leu Met Ala
    290                 295                 300
Met Val Lys Arg Lys Asp Phe
305                 310

<210> SEQ ID NO 35
<211> LENGTH: 314
<212> TYPE: PRT
<213> ORGANISM: Homo sapiens

<400> SEQUENCE: 35

Met Leu Leu Leu Leu Leu Leu Gly Pro Gly Ser Gly Leu Gly Ala
1               5                   10                  15
Val Val Ser Gln His Pro Ser Trp Val Ile Cys Lys Ser Gly Thr Ser
            20                  25                  30
Val Lys Ile Glu Cys Arg Ser Leu Asp Phe Gln Ala Thr Thr Met Phe
        35                  40                  45
Trp Tyr Arg Gln Phe Pro Lys Gln Ser Leu Met Leu Met Ala Thr Ser
    50                  55                  60
Asn Glu Gly Ser Lys Ala Thr Tyr Glu Gln Gly Val Glu Lys Asp Lys
65                  70                  75                  80
Phe Leu Ile Asn His Ala Ser Leu Thr Leu Ser Thr Leu Thr Val Thr
                85                  90                  95
Ser Ala His Pro Glu Asp Ser Ser Phe Tyr Ile Cys Ser Ala Lys Val
            100                 105                 110
Thr Ser Gly Gln His Gln Gly Thr Thr Asp Thr Gln Tyr Phe Gly Pro
        115                 120                 125
Gly Thr Arg Leu Thr Val Leu Glu Asp Leu Lys Asn Val Phe Pro Pro
    130                 135                 140
Glu Val Ala Val Phe Glu Pro Ser Glu Ala Glu Ile Ser His Thr Gln
145                 150                 155                 160
Lys Ala Thr Leu Val Cys Leu Ala Thr Gly Phe Tyr Pro Asp His Val
                165                 170                 175
Glu Leu Ser Trp Trp Val Asn Gly Lys Glu Val His Ser Gly Val Ser
            180                 185                 190
Thr Asp Pro Gln Pro Leu Lys Glu Gln Pro Ala Leu Asn Asp Ser Arg
        195                 200                 205
Tyr Cys Leu Ser Ser Arg Leu Arg Val Ser Ala Thr Phe Trp Gln Asn
    210                 215                 220
```

```
Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
        260                 265                 270

Tyr Gln Gln Gly Val Leu Ser Ala Thr Ile Leu Tyr Glu Ile Leu Leu
    275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310
```

<210> SEQ ID NO 36
<211> LENGTH: 307
<212> TYPE: PRT
<213> ORGANISM: Homo sapiens

<400> SEQUENCE: 36

```
Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Gly
            100                 105                 110

Arg Gly Tyr Glu Gln Tyr Phe Gly Pro Gly Thr Arg Leu Thr Val Thr
        115                 120                 125

Glu Asp Leu Lys Asn Val Phe Pro Pro Glu Val Ala Val Phe Glu Pro
    130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Ser Thr Asp Pro Gln Pro Leu Lys
            180                 185                 190

Glu Gln Pro Ala Leu Asn Asp Ser Arg Tyr Cys Leu Ser Ser Arg Leu
        195                 200                 205

Arg Val Ser Ala Thr Phe Trp Gln Asn Pro Arg Asn His Phe Arg Cys
    210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285
```

```
Val Leu Val Ser Ala Leu Val Leu Met Ala Met Val Lys Arg Lys Asp
    290                 295                 300
Ser Arg Gly
305

<210> SEQ ID NO 37
<211> LENGTH: 801
<212> TYPE: DNA
<213> ORGANISM: Homo sapiens

<400> SEQUENCE: 37
atgtggggag ttttccttct ttatgtttcc atgaagatgg gaggcactac aggacaaaac      60
attgaccagc ccactgagat gacagctacg gaaggtgcca ttgtccagat caactgcacg     120
taccagacat ctgggttcaa cgggctgttc tggtaccagc aacatgctgg cgaagcaccc     180
acatttctgt cttacaatgt tctggatggt ttggaggaga aggtcgtttt tcttcattc      240 cttagtcggt ctaaagggta cagttacctc cttttgaagg agctccagat gaaagactct     300
gcctcttacc tctgtgctgt gatggatagc agctataaat tgatcttcgg gagtgggacc     360
agactgctgg tcaggcctga tatccagaac cctgaccctg ccgtgtacca gctgagagac     420
tctaaatcca gtgacaagtc tgtctgccta ttcaccgatt ttgattctca aacaaatgtg     480
tcacaaagta aggattctga tgtgtatatc acagacaaaa ctgtgctaga catgaggtct     540
atggacttca agagcaacag tgctgtggcc tggagcaaca atctgactt tgcatgtgca      600 aacgccttca caacagcat tattccagaa gacaccttct ccccagccc agaaagttcc      660 tgtgatgtca agctggtcga gaaaagcttt gaaacagata cgaacctaaa cttttcaaaac    720 ctgtcagtga ttgggttccg aatcctcctc ctgaaagtgg ccgggtttaa tctgctcatg     780
acgctgcggc tgtggtccag c                                               801

<210> SEQ ID NO 38
<211> LENGTH: 813
<212> TYPE: DNA
<213> ORGANISM: Homo sapiens

<400> SEQUENCE: 38
atgctactca tcacatcaat gttggtctta tggatgcaat tgtcacaggt gaatggacaa      60
caggtaatgc aaattcctca gtaccagcat gtacaagaag gagaggactt caccacgtac     120
tgcaattcct caactacttt aagcaatata cagtggtata gcaaaggcc tggtggacat      180 cccgttttt tgatacagtt agtgaagagt ggagaagtga agaagcagaa aagactgaca      240
tttcagtttg gagaagcaaa aaagaacagc tccctgcaca tcacagccac ccagactaca     300
gatgtaggaa cctacttctg tgcggctgct ggtggtacta gctatggaaa gctgacattt     360
ggacaaggga ccatcttgac tgtccatcca atatccaga ccctgacccc tgccgtgtac      420
cagctgagag actctaaatc cagtgacaag tctgtctgcc tattcaccga ttttgattct     480
caaacaaatg tgtcacaaag taaggattct gatgtgtata tcacagacaa aactgtgcta     540
gacatgaggt ctatggactt caagagcaac agtgctgtgg cctggagcaa caaatctgac     600
tttgcatgtg caaacgcctt caacaacagc attattccag aagacacctt ctccccagc      660 ccagaaagtt cctgtgatgt caagctggtc gagaaaagct ttgaaacaga tacgaaccta     720
aactttcaaa acctgtcagt gattgggttc cgaatcctcc tctgaaagt ggccgggttt      780 aatctgctca tgacgctgcg gctgtggtcc agc                                  813
```

<210> SEQ ID NO 39
<211> LENGTH: 831
<212> TYPE: DNA
<213> ORGANISM: Homo sapiens

<400> SEQUENCE: 39

| | | | | | |
|---|---|---|---|---|---|
| atgaagacat | ttgctggatt | ttcgttcctg | tttttgtggc | tgcagctgga | ctgtatgagt | 60 |
| agaggagagg | atgtggagca | gagtcttttc | ctgagtgtcc | gagagggaga | cagctccgtt | 120 |
| ataaactgca | cttacacaga | cagctcctcc | acctactyat | actggtataa | gcaagaacct | 180 |
| ggagcaggtc | tccagttgct | gacgtatatt | ttttcaaata | tggacatgaa | acaagaccaa | 240 |
| agactcactg | ttctattgaa | taaaaaggat | aaacatctgt | ctctgcgcat | tgcagacacc | 300 |
| cagactgggg | actcagctat | ctacttctgt | gcagagacct | ggaccgacag | aggctcaacc | 360 |
| ctggggaggc | tatactttgg | aagaggaact | cagttgactg | tctggcctga | tatccagaac | 420 |
| cctgaccctg | ccgtgtacca | gctgagagac | tctaaatcca | gtgacaagtc | tgtctgccta | 480 |
| ttcaccgatt | ttgattctca | aacaaatgtg | tcacaaagta | aggattctga | tgtgtatatc | 540 |
| acagacaaaa | ctgtgctaga | catgaggtct | atggacttca | agagcaacag | tgctgtggcc | 600 |
| tggagcaaca | atctgacttt | gcatgtgcaa | acgccttca | acaacagcat | tattccagaa | 660 |
| gacaccttct | cccccagccc | agaaagttcc | tgtgatgtca | agctggtcga | gaaaagcttt | 720 |
| gaaacagata | cgaacctaaa | ctttcaaaac | ctgtcagtga | ttgggttccg | aatcctcctc | 780 |
| ctgaaagtgg | ccgggtttaa | tctgctcatg | acgttgcggc | tgtggtccag c | 831 |

<210> SEQ ID NO 40
<211> LENGTH: 840
<212> TYPE: DNA
<213> ORGANISM: Homo sapiens

<400> SEQUENCE: 40

| | | | | | |
|---|---|---|---|---|---|
| atggccatgc | tcctgggggc | atcagtgctg | attctgtggc | ttcagacaga | ctgggtaaac | 60 |
| agtcaacaga | agaatgatga | ccagcaagtt | aagcaaaatt | caccatccct | gagcgtccag | 120 |
| gaaggaagaa | tttctattct | gaactgtgac | tatactaaca | gcatgttga | ttatttccta | 180 |
| tggtacaaaa | ataccctgc | tgaaggtcct | acattcctga | tatctataag | ttccattaag | 240 |
| gataaaaatg | aagatggaag | attcactgtc | ttcttaaaca | aaagtgccaa | gcacctctct | 300 |
| ctgcacattg | tgccctccca | gcctggagac | tctgcagtgt | acttctgtgc | agcaagtctt | 360 |
| tataaccagg | gaggaaagct | tatcttcgga | cagggaacgg | agttatctgt | gaaacccaat | 420 |
| atccagaacc | ctgaccctgc | cgtgtaccag | ctgagagact | ctaaatccag | tgacaagtct | 480 |
| gtctgcctat | tcaccgattt | tgattctcaa | acaaatgtgt | cacaaagtaa | ggattctgat | 540 |
| gtgtatatca | cagacaaaac | tgtgctagac | atgaggtcta | tggacttcaa | gagcaacagt | 600 |
| gctgtggcct | ggagcaacaa | atctgacttt | gcatgtgcaa | acgccttcaa | caacagcatt | 660 |
| attccagaag | acaccttctt | ccccagccca | gaaagttcct | gtgatgtcaa | gctggtcgag | 720 |
| aaaagctttg | aaacagatac | gaacctaaac | tttcaaaacc | tgtcagtgat | tgggttccga | 780 |
| atcctcctcc | tgaaagtggc | cgggtttaat | ctgctcatga | cgctgcggct | gtggtccagc | 840 |

<210> SEQ ID NO 41
<211> LENGTH: 822
<212> TYPE: DNA
<213> ORGANISM: Homo sapiens

<400> SEQUENCE: 41

```
atggagaaga atcctttggc agccccatta ctaatcctct ggtttcatct tgactgcgtg    60
agcagcatac tgaacgtgga acaaagtcct cagtcactgc atgttcagga gggagacagc   120
accaatttca cctgcagctt cccttccagc aattttatg ccttacactg gtacagatgg    180
gaaactgcaa aaagccccga ggccttgttt gtaatgactt aaatgggga tgaaaagaag    240 aaaggacgaa taagtgccac tcttaatacc aaggagggtt acagctattt gtacatcaaa   300
ggatcccagc ctgaagactc agccacatac ctctgtgcct cggggattc cgggtatgca    360 ctcaacttcg gcaaaggcac ctcgctgttg gtcacacccc atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
actgtgctag acatgaggtc tatgacttc aagagcaaca gtgctgtggc ctggagcaac    600
aaatctgact ttgcatgtgc aaacgccttc aacaacagca ttattccaga agacaccttc   660
ttccccagcc cagaaagttc ctgtgatgtc aagctggtcg agaaaagctt gaaacagat    720 acgaacctaa actttcaaaa cctgtcagtg attgggttcc gaatcctcct cctgaaagtg   780
gccgggttta atctgctcat gacgctgcgg ctgtggtcca gc                      822
```

<210> SEQ ID NO 42
<211> LENGTH: 828
<212> TYPE: DNA
<213> ORGANISM: Homo sapiens

<400> SEQUENCE: 42

```
atgaactatt ctccaggctt agtatctctg atactcttac tgcttggaag aacccgtgga    60
aattcagtga cccagatgga agggccagtg actctctcag aagaggcctt cctgactata   120
aactgcacgt acacagccac aggataccct tccctttct ggtatgtcca atatcctgga    180
gaaggtctac agctcctcct gaaagccacg aaggctgatg acaagggaag caacaaaggt   240
tttgaagcca cataccgtaa agaaaccact tctttccact ggagaaagg ctcagttcaa    300 gtgtcagact cagcggtgta cttctgtgct ctgacaatat gggattatgg aggaagccaa   360
ggaaatctca tctttggaaa aggcactaaa ctctctgtta aaccaaatat ccagaaccct   420
gaccctgccg tgtaccagct gagagactct aaatccagtg acaagtctgt ctgcctattc   480
accgattttg attctcaaac aaatgtgtca caaagtaagg attctgatgt gtatatcaca   540
gacaaaactg tgctagacat gaggtctatg acttcaaga gcaacagtgc tgtggcctgg    600
agcaacaaat ctgactttgc atgtgcaaac gccttcaaca acagcattat tccagaagac   660
accttcttcc ccagcccaga aagttcctgt gatgtcaagc tggtcgagaa aagctttgaa   720
acagatacga acctaaactt tcaaaacctg tcagtgattg ggttccgaat cctcctcctg   780
aaagtggccg ggtttaatct gctcatgacg ctgcggctgt ggtccagc                828
```

<210> SEQ ID NO 43
<211> LENGTH: 807
<212> TYPE: DNA
<213> ORGANISM: Homo sapiens

<400> SEQUENCE: 43

```
atggtcctga aattctccgt gtccattctt tggattcagt tggcatgggt gagcacccag    60
ctgctggagc agagccctca gtttctaagc atccaagagg gagaaaatct cactgtgtac   120
tgcaactcct caagtgtttt ttccagctta caatggtaca cagcaggagcc tggggaaggt   180
```

-continued

| | |
|---|---|
| cctgtcctcc tggtgacagt agttacgggt ggagaagtga agaagctgaa gagactaacc | 240 |
| tttcagtttg gtgatgcaag aaaggacagt tctctccaca tcactgcagc ccagcctggt | 300 |
| gatacaggcc tctacctctg tgcaggagaa aattccgggt atgcactcaa cttcggcaaa | 360 |
| ggcacctcgc tgttggtcac accccatatc cagaaccctg accctgccgt gtaccagctg | 420 |
| agagactcta atccagtgac aagtctgtc tgcctattca ccgattttga ttctcaaaca | 480 |
| aatgtgtcac aaagtaagga ttctgatgtg tatatcacag acaaaactgt gctagacatg | 540 |
| aggtctatgg acttcaagag caacagtgct gtggcctgga gcaacaaatc tgactttgca | 600 |
| tgtgcaaacg ccttcaacaa cagcattatt ccagaagaca ccttcttccc cagcccagaa | 660 |
| agttcctgtg atgtcaagct ggtcgagaaa agctttgaaa cagatacgaa cctaaacttt | 720 |
| caaaaccctgt cagtgattgg gttccgaatc ctcctcctga agtggccgg gttttaatctg | 780 |
| ctcatgacgc tgcggctgtg gtccagc | 807 |

<210> SEQ ID NO 44
<211> LENGTH: 825
<212> TYPE: DNA
<213> ORGANISM: Homo sapiens

<400> SEQUENCE: 44

| | |
|---|---|
| atgatgaaat ccttgagagt tttactggtg atcctgtggc ttcagttaag ctgggtttgg | 60 |
| agccaacaga aggaggtgga gcaggatcct ggaccactca gtgttccaga gggagccatt | 120 |
| gtttctctca actgcactta cagcaacagt gcttttcaat acttcatgtg gtacagacag | 180 |
| tattccagaa aaggccctga gttgctgatg tacacatact ccagtggtaa caaagaagat | 240 |
| ggaaggttta cagcacaggt cgataaatcc agcaagtata tctccttgtt catcagagac | 300 |
| tcacagccca gtgattcagc cacctacctc tgtgcaatga gctatcagg aggaagctac | 360 |
| atacctacat ttggaagagg aaccagcctt attgttcatc cgtatatcca gaaccctgac | 420 |
| cctgccgtgt accagctgag agactctaaa tccagtgaca gtctgtctg cctattcacc | 480 |
| gattttgatt ctcaaacaaa tgtgtcacaa agtaaggatt ctgatgtgta tatcacagac | 540 |
| aaaactgtgc tagacatgag gtctatggac ttcaagagca acagtgctgt ggcctggagc | 600 |
| aacaaatctg actttgcatg tgcaaacgcc ttcaacaaca gcattattcc agaagacacc | 660 |
| ttcttcccca gcccagaaag ttcctgtgat gtcaagctgg tcgagaaaag ctttgaaaca | 720 |
| gatacgaacc taaactttca aaacctgtca gtgattgggt tccgaatcct cctcctgaaa | 780 |
| gtggccgggt taatctgct catgacgctg cggctgtggt ccagc | 825 |

<210> SEQ ID NO 45
<211> LENGTH: 825
<212> TYPE: DNA
<213> ORGANISM: Homo sapiens

<400> SEQUENCE: 45

| | |
|---|---|
| atgctccttg aacatttatt aataatcttg tggatgcagc tgacatgggt cagtggtcaa | 60 |
| cagctgaatc agagtcctca atctatgttt atccaggaag agaagatgt ctccatgaac | 120 |
| tgcacttctt caagcatatt taacccctgg ctatggtaca agcaggaccc tgggaaggt | 180 |
| cctgtcctct tgatagcctt atataaggct ggtgaattga cctcaaatgg aagactgact | 240 |
| gctcagtttg gtataaccag aaaggacagc ttcctgaata tctcagcatc catacctagt | 300 |
| gatgtaggca tctacttctg tgctgggcag ctaggaggg ctggtggtac tagctatgga | 360 |
| aagctgacat ttggacaagg gaccatcttg actgtccatc caaatatcca gaaccctgac | 420 |

```
cctgccgtgt accagctgag agactctaaa tccagtgaca agtctgtctg cctattcacc    480
gattttgatt ctcaaacaaa tgtgtcacaa agtaaggatt ctgatgtgta tcacagac      540 aaaactgtgc tagacatgag gtctatggac ttcaagagca acagtgctgt ggcctggagc    600
aacaaatctg actttgcatg tgcaaacgcc ttcaacaaca gcattattcc agaagacacc    660
ttcttcccca gcccagaaag ttcctgtgat gtcaagctgg tcgagaaaag ctttgaaaca    720
gatacgaacc taaactttca aaacctgtca gtgattgggt tccgaatcct cctcctgaaa    780
gtggccgggt ttaatctgct catgacgctg cggctgtggt ccagc                    825
```

<210> SEQ ID NO 46
<211> LENGTH: 822
<212> TYPE: DNA
<213> ORGANISM: Homo sapiens

<400> SEQUENCE: 46

```
atgacatcca ttcgagctgt atttatattc ctgtggctgc agctggactt ggtgaatgga     60
gagaatgtgg agcagcatcc ttcaaccctg agtgtccagg agggagacag cgctgttatc    120
aagtgtactt attcagacag tgcctcaaac tacttccctt ggtataagca agaacttgga    180
aaaggacctc agcttattat agacattcgt tcaaatgtgg gcgaaaagaa agaccaacga    240
attgctgtta cattgaacaa gacagccaaa catttctccc tgcacatcac agagacccaa    300
cctgaagact cggctgtcta cttctgtgca gcaaactgga gcccgcaagg aaatgagaaa    360
ttaacctttg ggactggaac aagactcacc atcataccca atatccagaa ccctgaccct    420
gccgtgtacc agctgagaga ctctaaatcc agtgacaagt ctgtctgcct attcaccgat    480
tttgattctc aaacaaatgt gtcacaaagt aaggattctg atgtgtatat cacagacaaa    540
actgtgctag acatgaggtc tatggacttc aagagcaaca gtgctgtggc ctggagcaac    600
aaatctgact ttgcatgtgc aaacgccttc aacaacagca ttattccaga agacaccttc    660
ttccccagcc cagaaagttc ctgtgatgtc aagctggtcg agaaaagctt tgaaacagat    720
acgaacctaa actttcaaaa cctgtcagtg attgggttcc gaatcctcct cctgaaagtg    780
gccgggttta atctgctcat gacgctgcgg ctgtggtcca gc                       822
```

<210> SEQ ID NO 47
<211> LENGTH: 801
<212> TYPE: DNA
<213> ORGANISM: Homo sapiens

<400> SEQUENCE: 47

```
atgtggggag ttttccttct ttatgtttcc atgaagatgg gaggcactac aggacaaaac     60
attgaccagc ccactgagat gacagctacg gaaggtgcca ttgtccagat caactgcacg    120
taccagacat ctgggttcaa cgggctgttc tggtaccagc aacatgctgg cgaagcaccc    180
acatttctgt cttacaatgt tctggatggt ttggaggaga aggtcgtttt tcttcattc     240 cttagtcggt ctaaagggta cagttacctc cttttgaagg agctccagat gaaagactct    300
gcctcttacc tctgtgcttc catggatagc aactatcagt taatctgggg cgctgggacc    360
aagctaatta taaagccaga tatccagaac cctgaccctg ccgtgtacca gctgagagac    420
tctaaatcca gtgacaagtc tgtctgccta ttcaccgatt ttgattctca aacaaatgtg    480
tcacaaagta aggattctga tgtgtatatc acagacaaaa ctgtgctaga catgaggtct    540
atggacttca agagcaacag tgctgtggcc tggagcaaca aatctgactt tgcatgtgca    600
```

```
aacgccttca caacagcat tattccagaa gacaccttct tccccagccc agaaagttcc    660
tgtgatgtca agctggtcga gaaaagcttt gaaacagata cgaacctaaa ctttcaaaac   720
ctgtcagtga ttgggttccg aatcctcctc ctgaaagtgg ccgggtttaa tctgctcatg   780
acgctgcggc tgtggtccag c                                            801

<210> SEQ ID NO 48
<211> LENGTH: 822
<212> TYPE: DNA
<213> ORGANISM: Homo sapiens

<400> SEQUENCE: 48
atgatatcct tgagagtttt actggtgatc ctgtggcttc agttaagctg ggtttggagc    60
caacggaagg aggtggagca ggatcctgga cccttcaatg ttccagaggg agccactgtc   120
gctttcaact gtacttacag caacagtgct tctcagtctt tcttctggta cagacaggat   180
tgcaggaaag aacctaagtt gctgatgtcc gtatactcca gtggtaatga agatggaagg   240
tttacagcac agctcaatag agccagccag tatatttccc tgctcatcag agactccaag   300
ctcagtgatt cagccaccta cctctgtgtg gtgaacagat tcacaaggga tggaaacaaa   360
ctggtctttg gcgcaggaac cattctgaga gtcaagtcct atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
actgtgctag acatgaggtc tatggacttc aagagcaaca gtgctgtggc ctggagcaac   600
aaatctgact ttgcatgtgc aaacgccttc aacaacagca ttattccaga agacaccttc   660
ttccccagcc agaaagttc tgtgatgtc aagctggtcg agaaaagctt gaaacagat   720 acgaaccta actttcaaaa cctgtcagtg attgggttcc gaatcctcct cctgaaagtg   780
gccgggttta atctgctcat gacgctgcgg ctgtggtcca gc                       822

<210> SEQ ID NO 49
<211> LENGTH: 936
<212> TYPE: DNA
<213> ORGANISM: Homo sapiens

<400> SEQUENCE: 49
atgagcatcg gcctcctgtg ctgtgtggcc ttttctctcc tgtgggcaag tccagtgaat    60
gctggtgtca ctcagacccc aaaattccag gtcctgaaga caggacagag catgacactg   120
cagtgtgccc aggatatgaa ccataactcc atgtactggt atcgacaaga cccaggcatg   180
ggactgaggc tgatttatta ctcagcttct gagggtacca ctgacaaagg agaagtcccc   240
aatggctaca atgtctccag attaaacaaa cgggagttct cgctcaggct ggagtcggct   300
gctccctccc agacatctgt gtacttctgt gccagcagtg aggtgacagg gggatacaat   360
gagcagttct cgggccagg acacggctc accgtgctag aggacctgaa aaacgtgttc   420
ccacccgagg tcgctgtgtt tgagccatca gaagcagaga tctcccacac ccaaaaggcc   480
acactggtgt gcctggccac aggcttctac cccgaccacg tggagctgag ctggtgggtg   540
aatgggaagg aggtgcacag tggggtcagc acagacccgc agccctcaa ggagcagccc   600 gccctcaatg actccagata ctgcctgagc agccgcctga gggtctcggc caccttctgg   660
cagaaccccg caaccactt ccgctgtcaa gtccagttct acgggctctc ggagaatgac   720
gagtggaccc aggataggc caaacctgtc acccagatcg tcagcgccga ggcctggggt   780
agagcagact gtggcttcac ctccgagtct taccagcaag gggtcctgtc tgccaccatc   840
```

```
ctctatgaga tcttgctagg gaaggccacc ttgtatgccg tgctggtcag tgccctcgtg    900
ctgatggcca tggtcaagag aaaggattcc agaggc                              936
```

<210> SEQ ID NO 50
<211> LENGTH: 933
<212> TYPE: DNA
<213> ORGANISM: Homo sapiens

<400> SEQUENCE: 50

```
atgctgagtc ttctgctcct tctcctggga ctaggctctg tgttcagtgc tgtcatctct     60
caaaagccaa gcagggatat ctgtcaacgt ggaacctccc tgacgatcca gtgtcaagtc    120
gatagccaag tcaccatgat gttctggtac cgtcagcaac ctggacagag cctgacactg    180
atcgcaactg caaatcaggg ctctgaggcc acatatgaga gtggatttgt cattgacaag    240
tttcccatca gccgcccaaa cctaacattc tcaactctga ctgtgagcaa catgagccct    300
gaagacagca gcatatatct ctgcagcgtt ggggcggggc aaggacctta cacagatacg    360
cagtattttg gcccaggcac ccggctgaca gtgctcgagg acctgaaaaa cgtgttccca    420
cccgaggtcg ctgtgtttga gccatcagaa gcagagatct cccacaccca aaaggccaca    480
ctggtgtgcc tggccacagg cttctacccc gaccacgtgg agctgagctg gtgggtgaat    540
gggaaggagg tgcacagtgg ggtcagcaca gacccgcagc ccctcaagga gcagcccgcc    600
ctcaatgact ccagatactg cctgagcagc cgcctgaggg tctcggccac cttctggcag    660 aaccccgca accacttccg ctgtcaagtc cagttctacg gctctcgga gaatgacgag    720 tggacccagg atagggccaa acctgtcacc cagatcgtca gcgccgaggc tggggtaga    780 gcagactgtg gcttcacctc cgagtcttac cagcaagggg tcctgtctgc caccatcctc    840
tatgagatct gctagggaa ggccaccttg tatgccgtgc tggtcagtgc cctcgtgctg    900
atggccatgg tcaagagaaa ggattccaga ggc                                 933
```

<210> SEQ ID NO 51
<211> LENGTH: 933
<212> TYPE: DNA
<213> ORGANISM: Homo sapiens

<400> SEQUENCE: 51

```
atgggaatca ggctcctgtg tcgtgtggcc ttttgtttcc tggctgtagg cctcgtagat     60
gtgaaagtaa cccagagctc gagatatcta gtcaaaagga cgggagagaa agttttctg    120 gaatgtgtcc aggatatgga ccatgaaaat atgttctggt atcgacaaga cccaggtctg    180 ggctacggc tgatctattt ctcatatgat gttaaaatga agaaaaagg agatattcct    240 gaggggtaca gtgtctctag agagaagaag gagcgcttct ccctgattct ggagtccgcc    300
agcaccaacc agacatctat gtacctctgt gccagcagct taggggcgac aggggctaat    360
gaaaaactgt tttttggcag tggaacccag ctctctgtct tggaggacct gaacaaggtg    420
ttcccacccg aggtcgctgt gtttgagcca tcagaagcag agatctccca cacccaaaag    480
gccacactgg tgtgcctggc cacaggcttc tccctgacc acgtggagct gagctggtgg    540
gtgaatggga aggaggtgca cagtgggtc agcacgacc gcagcccct caaggagcag    600 cccgccctca atgactccag atactgcctg agcagccgcc tgagggtctc ggccaccttc    660
tggcagaacc ccgcaaccca cttccgctgt caagtccagt tctacgggct ctcggagaat    720
gacgagtgga cccaggatag ggccaaaccc gtcacccaga tcgtcagcgc cgaggcctgg    780
```

| | |
|---|---:|
| ggtagagcag actgtggctt acctcggtg tcctaccagc aaggggtcct gtctgccacc | 840 |
| atcctctatg agatcctgct agggaaggcc accctgtatg ctgtgctggt cagcgccctt | 900 |
| gtgttgatgg ccatggtcaa gagaaaggat ttc | 933 |

```
<210> SEQ ID NO 52
<211> LENGTH: 924
<212> TYPE: DNA
<213> ORGANISM: Homo sapiens

<400> SEQUENCE: 52
```

| | |
|---|---:|
| atgggctcct ggaccctctg ctgtgtgtcc ctttgcatcc tggtagcaaa gcacacagat | 60 |
| gctggagtta tccagtcacc ccggcacgag gtgacagaga tgggacaaga agtgactctg | 120 |
| agatgtaaac caatttcagg acacgactac ctttttctggt acagacagac catgatgcgg | 180 |
| ggactggagt tgctcattta cttttaacaac aacgttccga tagatgattc agggatgccc | 240 |
| gaggatcgat tctcagctaa gatgcctaat gcatcattct ccactctgaa gatccagccc | 300 |
| tcagaaccca gggactcagc tgtgtacttc tgtgccagca gctacagggg cactgaagct | 360 |
| ttcttttggac aaggcaccag actcacagtt gtagaggacc tgaacaaggt gttcccaccc | 420 |
| gaggtcgctg tgtttgagcc atcagaagca gagatctccc acacccaaaa ggccacactg | 480 |
| gtgtgcctgg ccacaggctt cttccctgac cacgtggagc tgagctggtg ggtgaatggg | 540 |
| aaggaggtgc acagtgggt cagcacggac ccgcagcccc tcaaggagca gcccgccctc | 600 |
| aatgactcca gatactgcct gagcagccgc ctgagggtct cggccacctt ctggcagaac | 660 |
| ccccgcaacc acttccgctg tcaagtccag ttctacgggc tctcggagaa tgacgagtgg | 720 |
| acccaggata gggccaaacc cgtcacccag atcgtcagcg ccgaggcctg ggtagagca | 780 |
| gactgtggct ttacctcggt gtcctaccag caaggggtcc tgtctgccac catcctctat | 840 |
| gagatcctgc tagggaaggc caccctgtat gctgtgctgg tcagcgccct tgtgttgatg | 900 |
| gccatggtca agagaaagga tttc | 924 |

```
<210> SEQ ID NO 53
<211> LENGTH: 927
<212> TYPE: DNA
<213> ORGANISM: Homo sapiens

<400> SEQUENCE: 53
```

| | |
|---|---:|
| atgggccctg ggctcctctg ctgggtgctg ctttgtctcc tgggagcagg cccagtggac | 60 |
| gctggagtca cccaaaagtcc cacacacctg atcaaaacga gaggacagca cgtgactctg | 120 |
| agatgctctc ctatctctgg gcacaagagt gtgtcctggt accaacaggt cctgggtcag | 180 |
| gggcccagt ttatctttca gtattatgag aaagaagaga gaggaagagg aaacttccct | 240 |
| gatcgattct cagctcgcca gttccctaac tatagctctg agctgaatgt gaacgccttg | 300 |
| ttgctggggg actcggccct gtatctctgt gccagcagct tgacgttgg tttgccaccc | 360 |
| ctccactttg ggaacgggac caggctcact gtgacagagg acctgaacaa ggtgttccca | 420 |
| cccgaggtcg ctgtgtttga gccatcagaa gcagagatct cccacaccca aaaggccaca | 480 |
| ctggtgtgcc tggccacagg cttcttccct gaccacgtgg agctgagctg tgggtgaat | 540 |
| gggaaggagg tgcacagtgg ggtcagcacg gacccgcagc ccctcaagga gcagcccgcc | 600 |
| ctcaatgact ccagatactg cctgagcagc cgcctgaggg tctcggccac cttctggcag | 660 |
| aaccccgca accacttccg ctgtcaagtc cagttctacg gctctcgga gaatgacgag | 720 |
| tggacccagg atagggccaa acccgtcacc cagatcgtca gcgccgaggc ctggggtaga | 780 |

| | |
|---|---:|
| gcagactgtg gctttacctc ggtgtcctac cagcaagggg tcctgtctgc caccatcctc | 840 |
| tatgagatcc tgctagggaa ggccaccctg tatgctgtgc tggtcagcgc ccttgtgttg | 900 |
| atggccatgg tcaagagaaa ggatttc | 927 |

<210> SEQ ID NO 54
<211> LENGTH: 927
<212> TYPE: DNA
<213> ORGANISM: Homo sapiens

<400> SEQUENCE: 54

| | |
|---|---:|
| atgggtcctg ggcttctcca ctggatggcc ctttgtctcc ttggaacagg tcatggggat | 60 |
| gccatggtca tccagaaccc aagataccag gttacccagt ttggaaagcc agtgaccctg | 120 |
| agttgttctc agactttgaa ccataacgtc atgtactggt accagcagaa gtcaagtcag | 180 |
| gccccaaagc tgctgttcca ctactatgac aaagatttta caatgaagc agacacccct | 240 |
| gataacttcc aatccaggag gccgaacact tctttctgct tcttgacat ccgctcacca | 300 |
| ggcctggggg acgcagccat gtacctgtgt gccaccagca gagtggga gacccagtac | 360 |
| ttcgggccag gcacgcggct cctggtgctc gaggacctga aaaacgtgtt cccacccgag | 420 |
| gtcgctgtgt ttgagccatc agaagcagag atctcccaca cccaaaaggc cacactggtg | 480 |
| tgcctggcca caggcttcta ccccgaccac gtggagctga ctggtgggt gaatgggaag | 540 |
| gaggtgcaca gtggggtcag cacagacccg cagcccctca aggagcagcc cgccctcaat | 600 |
| gactccagat actgcctgag cagccgcctg agggtctcgg ccaccttctg gcagaacccc | 660 |
| cgcaaccact ccgctgtca gtccagttc tacgggctct cggagaatga cgagtggacc | 720 |
| caggataggg ccaaacctgt cacccagatc gtcagcgccg aggcctgggg tagagcagac | 780 |
| tgtggcttca cctccgagtc ttaccagcaa ggggtcctgt ctgccaccat cctctatgag | 840 |
| atcttgctag gaaggccac cttgtatgcc gtgctggtca gtgccctcgt gctgatggcc | 900 |
| atggtcaaga gaaaggattc cagaggc | 927 |

<210> SEQ ID NO 55
<211> LENGTH: 945
<212> TYPE: DNA
<213> ORGANISM: Homo sapiens

<400> SEQUENCE: 55

| | |
|---|---:|
| atgactatca ggctcctctg ctacatgggc ttttattttc tggggcagg cctcatggaa | 60 |
| gctgacatct accagacccc aagataccct tgttatggga caggaaagaa gatcactctg | 120 |
| gaatgttctc aaaccatggg ccatgacaaa atgtactggt atcaacaaga tccaggaatg | 180 |
| gaactacacc tcatccacta ttcctatgga gttaattcca cagagaaggg agatctttcc | 240 |
| tctgagtcaa cagtctccag aataaggacg gagcattttc ccctgaccct ggagtctgcc | 300 |
| aggcccctcac atacctctca gtacctctgt gccagcagcc aactttaccg ggacacctcg | 360 |
| aacaccgggg agctgttttt tggagaaggc tctaggctga ccgtactgga ggacctgaaa | 420 |
| aacgtgttcc cacccgaggt cgctgtgttt gagccatcag aagcagagat ctcccacacc | 480 |
| caaaaggcca cactggtgtg cctggccaca ggcttctacc ccgaccacgt ggagctgagc | 540 |
| tggtgggtga atgggaagga ggtgcacagt ggggtcagca cagacccgca gcccctcaag | 600 |
| gagcagcccg ccctcaatga ctccagatac tgcctgagca gccgcctgag ggtctcggcc | 660 |
| accttctggc agaaccccg caaccacttc cgctgtcaag tccagttcta cgggctctcg | 720 |

| | |
|---|---|
| gagaatgacg agtggaccca ggatagggcc aaacctgtca cccagatcgt cagcgccgag | 780 |
| gcctggggta gagcagactg tggcttcacc tccgagtctt accagcaagg ggtcctgtct | 840 |
| gccaccatcc tctatgagat cttgctaggg aaggccacct tgtatgccgt gctggtcagt | 900 |
| gccctcgtgc tgatggccat ggtcaagaga aaggattcca gaggc | 945 |

<210> SEQ ID NO 56
<211> LENGTH: 939
<212> TYPE: DNA
<213> ORGANISM: Homo sapiens

<400> SEQUENCE: 56

| | |
|---|---|
| atgagcatcg gcctcctgtg ctgtgcagcc ttgtctctcc tgtgggcagg tccagtgaat | 60 |
| gctggtgtca ctcagacccc aaaattccag gtcctgaaga caggacagag catgacactg | 120 |
| cagtgtgccc aggatatgaa ccatgaatac atgtcctggt atcgacaaga cccaggcatg | 180 |
| gggctgaggc tgattcatta ctcagttggt gctggtatca ctgaccaagg agaagtcccc | 240 |
| aatggctaca atgtctccag atcaaccaca gaggatttcc cgctcaggct gctgtcggct | 300 |
| gctccctccc agacatctgt gtacttctgt gccagcggaa tcagcgggac agcgagctcc | 360 |
| tataattcac ccctccactt tgggaacggg accaggctca ctgtgacaga ggacctgaac | 420 |
| aaggtgttcc cacccgaggt cgctgtgttt gagccatcag aagcagagat ctcccacacc | 480 |
| caaaaggcca cactggtgtg cctggccaca ggcttcttcc ctgaccacgt ggagctgagc | 540 |
| tggtgggtga atgggaagga ggtgcacagt ggggtcagca cggacccgca gcccctcaag | 600 |
| gagcagcccg ccctcaatga ctccagatac tgcctgagca gccgcctgag ggtctcggcc | 660 |
| accttctggc agaaccccg caaccacttc cgctgtcaag tccagttcta cgggctctcg | 720 |
| gagaatgacg agtggaccca ggatagggcc aaacccgtca cccagatcgt cagcgccgag | 780 |
| gcctggggta gagcagactg tggctttacc tcggtgtcct accagcaagg ggtcctgtct | 840 |
| gccaccatcc tctatgagat cctgctaggg aaggccaccc tgtatgctgt gctggtcagc | 900 |
| gcccttgtgt tgatggccat ggtcaagaga aaggatttc | 939 |

<210> SEQ ID NO 57
<211> LENGTH: 936
<212> TYPE: DNA
<213> ORGANISM: Homo sapiens

<400> SEQUENCE: 57

| | |
|---|---|
| atgggcttca ggctcctctg ctgtgtggcc ttttgtctcc tgggagcagg cccagtggat | 60 |
| tctggagtca cacaaacccc aaagcacctg atcacagcaa ctggacagcg agtgacgctg | 120 |
| agatgctccc ctaggtctgg agacctctct gtgtactggt accaacgaga cctgaccag | 180 |
| ggcctccagt tcctcattca gtattataat ggagaagaga gagcaaaagg aaacattctt | 240 |
| gaacgattct ccgcacaaca gttccctgac ttgcactctg aactaaacct gagctctctg | 300 |
| gagctggggg actcagcttt gtatttctgt gccagcagcg tcgagggggg attggcagat | 360 |
| acgcagtatt ttggcccagg cacccggctg acagtgctcg aggacctgaa aaacgtgttc | 420 |
| ccacccgagg tcgctgtgtt tgagccatca gaagcagaga tctcccacac ccaaaaggcc | 480 |
| acactggtgt gcctggccac aggcttctac cccgaccacg tggagctgag ctggtgggtg | 540 |
| aatgggaagg aggtgcacag tggggtcagc acagacccgc agcccctcaa ggagcagccc | 600 |
| gccctcaatg actccagata ctgcctgagc agccgcctga ggtctcggc caccttctgg | 660 |
| cagaaccccc gcaaccactt ccgctgtcaa gtccagttct acgggctctc ggagaatgac | 720 |

| | |
|---|---|
| gagtggaccc aggatagggc caaacctgtc acccagatcg tcagcgccga ggcctggggt | 780 |
| agagcagact gtggcttcac ctccgagtct taccagcaag gggtcctgtc tgccaccatc | 840 |
| ctctatgaga tcttgctagg gaaggccacc ttgtatgccg tgctggtcag tgccctcgtg | 900 |
| ctgatggcca tggtcaagag aaaggattcc agaggc | 936 |

<210> SEQ ID NO 58
<211> LENGTH: 933
<212> TYPE: DNA
<213> ORGANISM: Homo sapiens

<400> SEQUENCE: 58

| | |
|---|---|
| atgactatca ggctcctctg ctacatgggc ttttattttc tgggggcagg cctcatggaa | 60 |
| gctgacatct accagacccc aagatacctt gttataggga caggaaagaa gatcactctg | 120 |
| gaatgttctc aaaccatggg ccatgacaaa atgtactggt atcaacaaga tccaggaatg | 180 |
| gaactcaccc tcatccacta ttcctatgga gttaattcca cagagaaggg agatctttcc | 240 |
| tctgagtcaa cagtctccag aataaggacg gagcattttc ccctgaccct ggagtctgcc | 300 |
| aggccctcac atacctctca gtacctctgt gccagcagtg aatatatcca gtactctgga | 360 |
| aacaccatat attttggaga gggaagttgg ctcactgttg tagaggacct gaacaaggtg | 420 |
| ttcccacccg aggtcgctgt gtttgagcca tcagaagcag agatctccca cacccaaaag | 480 |
| gccacactgg tgtgcctggc cacaggcttc ttccctgacc acgtggagct gagctggtgg | 540 |
| gtgaatggga aggaggtgca cagtgggtc agcacggacc cgcagcccct caaggagcag | 600 |
| cccgccctca atgactccag atactgcctg agcagccgcc tgagggtctc ggccaccttc | 660 |
| tggcagaacc cccgcaacca cttccgctgt caagtccagt tctacgggct ctcggagaat | 720 |
| gacgagtgga cccaggatag gccaaaccc gtcacccaga tcgtcagcgc cgaggcctgg | 780 |
| ggtagagcag actgtggctt tacctcggtg tcctaccagc aagggtcct gtctgccacc | 840 |
| atcctctatg agatcctgct agggaaggcc accctgtatg ctgtgctggt cagcgcccttt | 900 |
| gtgttgatgg ccatggtcaa gagaaaggat ttc | 933 |

<210> SEQ ID NO 59
<211> LENGTH: 942
<212> TYPE: DNA
<213> ORGANISM: Homo sapiens

<400> SEQUENCE: 59

| | |
|---|---|
| atgctgctgc ttctgctgct tctggggcca ggctccgggc ttggtgctgt cgtctctcaa | 60 |
| catccgagct gggttatctg taagagtgga acctctgtga agatcgagtg ccgttccctg | 120 |
| gactttcagg ccacaactat gttttggtat cgtcagttcc cgaaacagag tctcatgctg | 180 |
| atggcaactt ccaatgaggg ctccaaggcc acatacgagc aaggcgtcga aaggacaag | 240 |
| tttctcatca accatgcaag cctgaccttg tccactctga cagtgaccag tgcccatcct | 300 |
| gaagacagca gcttctacat ctgcagtgcg aaggtgacta gcgggcaaca ccaagggacc | 360 |
| acagatacgc agtattttgg cccaggcacc cggctgacag tgctcgagga cctgaaaaac | 420 |
| gtgttcccac ccgaggtcgc tgtgtttgag ccatcagaag cagagatctc cacacccaa | 480 |
| aaggccacac tggtgtgcct ggccacaggc ttctaccccg accacgtgga gctgagctgg | 540 |
| tgggtgaatg ggaaggaggt gcacagtggg gtcagcacag acccgcagcc cctcaaggag | 600 |
| cagcccgccc tcaatgactc cagatactgc ctgagcagcc gcctgagggt ctcggccacc | 660 |

```
ttctggcaga accccccgcaa ccacttccgc tgtcaagtcc agttctacgg gctctcggag    720
aatgacgagt ggacccagga tagggccaaa cctgtcaccc agatcgtcag cgccgaggcc    780
tggggtagag cagactgtgg cttcacctcc gagtcttacc agcaaggggt cctgtctgcc    840
accatcctct atgagatctt gctagggaag gccaccttgt atgccgtgct ggtcagtgcc    900
ctcgtgctga tggccatggt caagagaaag gattccagag gc                       942
```

<210> SEQ ID NO 60
<211> LENGTH: 921
<212> TYPE: DNA
<213> ORGANISM: Homo sapiens

<400> SEQUENCE: 60

```
atgctgagtc ttctgctcct ctcctggga ctaggctctg tgttcagtgc tgtcatctct      60
caaaagccaa gcagggatat ctgtcaacgt ggaacctccc tgacgatcca gtgtcaagtc    120
gatagccaag tcaccatgat gttctggtac cgtcagcaac ctggacagag cctgacactg    180
atcgcaactg caaatcaggg ctctgaggcc acatatgaga gtggatttgt cattgacaag    240
tttcccatca gccgcccaaa cctaacattc tcaactctga ctgtgagcaa catgagccct    300
gaagacagca gcatatatct ctgcagcgtt gaaggcaggg gttacgagca gtacttcggg    360
ccgggcacca ggctcacggt cacagaggac ctgaaaaacg tgttcccacc cgaggtcgct    420
gtgtttgagc catcagaagc agagatctcc cacacccaaa aggccacact ggtgtgcctg    480
gccacaggct ctaccccga ccacgtggag ctgagctggt gggtgaatgg aaggaggtg     540 cacagtgggg tcagcacaga cccgcagccc tcaaggagc agcccgccct caatgactcc    600
agatactgcc tgagcagccg cctgagggtc tcggccacct tctggcagaa ccccgcaac    660 cacttccgct gtcaagtcca gttctacggg ctctcggaga atgacgagtg gacccaggat    720
agggccaaac ctgtcaccca gatcgtcagc gccgaggcct ggggtagagc agactgtggc    780
ttcacctccg agtcttacca gcaaggggtc ctgtctgcca ccatcctcta tgagatcttg    840
ctagggaagg ccaccttgta tgccgtgctg gtcagtgccc tcgtgctgat ggccatggtc    900
aagagaaagg attccagagg c                                              921
```

<210> SEQ ID NO 61
<211> LENGTH: 310
<212> TYPE: PRT
<213> ORGANISM: Homo sapiens

<400> SEQUENCE: 61

```
Met Gln Trp Ala Leu Ala Val Leu Leu Ala Phe Leu Ser Pro Ala Ser
1               5                  10                  15

Gln Lys Ser Ser Asn Leu Glu Gly Arg Thr Lys Ser Val Ile Arg Gln
            20                  25                  30

Thr Gly Ser Ser Ala Glu Ile Thr Cys Asp Leu Ala Glu Gly Ser Thr
        35                  40                  45

Gly Tyr Ile His Trp Tyr Leu His Gln Glu Gly Lys Ala Pro Gln Arg
    50                  55                  60

Leu Leu Tyr Tyr Asp Ser Tyr Thr Ser Ser Val Val Leu Glu Ser Gly
65                  70                  75                  80

Ile Ser Pro Gly Lys Tyr Asp Thr Tyr Gly Ser Thr Arg Lys Asn Leu
                85                  90                  95

Arg Met Ile Leu Arg Asn Leu Ile Glu Asn Asp Ser Gly Val Tyr Tyr
            100                 105                 110
```

```
Cys Ala Thr Trp Glu Thr Gln Glu Leu Gly Lys Lys Ile Lys Val Phe
            115                 120                 125

Gly Pro Gly Thr Lys Leu Ile Ile Thr Asp Lys Gln Leu Asp Ala Asp
130                 135                 140

Val Ser Pro Lys Pro Thr Ile Phe Leu Pro Ser Ile Ala Glu Thr Lys
145                 150                 155                 160

Leu Gln Lys Ala Gly Thr Tyr Leu Cys Leu Leu Glu Lys Phe Phe Pro
                165                 170                 175

Asp Val Ile Lys Ile His Trp Gln Glu Lys Lys Ser Asn Thr Ile Leu
            180                 185                 190

Gly Ser Gln Glu Gly Asn Thr Met Lys Thr Asn Asp Thr Tyr Met Lys
        195                 200                 205

Phe Ser Trp Leu Thr Val Pro Glu Lys Ser Leu Asp Lys Glu His Arg
210                 215                 220

Cys Ile Val Arg His Glu Asn Asn Lys Asn Gly Val Asp Gln Glu Ile
225                 230                 235                 240

Ile Phe Pro Pro Ile Lys Thr Asp Val Ile Thr Met Asp Pro Lys Asp
                245                 250                 255

Asn Cys Ser Lys Asp Ala Asn Asp Thr Leu Leu Leu Gln Leu Thr Asn
            260                 265                 270

Thr Ser Ala Tyr Tyr Met Tyr Leu Leu Leu Leu Lys Ser Val Val
        275                 280                 285

Tyr Phe Ala Ile Ile Thr Cys Cys Leu Leu Arg Arg Thr Ala Phe Cys
290                 295                 300

Cys Asn Gly Glu Lys Ser
305                 310

<210> SEQ ID NO 62
<211> LENGTH: 295
<212> TYPE: PRT
<213> ORGANISM: Homo sapiens

<400> SEQUENCE: 62

Met Leu Phe Ser Ser Leu Leu Cys Val Phe Val Ala Phe Ser Tyr Ser
1               5                   10                  15

Gly Ser Ser Val Ala Gln Lys Val Thr Gln Ala Gln Ser Ser Val Ser
            20                  25                  30

Met Pro Val Arg Lys Ala Val Thr Leu Asn Cys Leu Tyr Glu Thr Ser
        35                  40                  45

Trp Trp Ser Tyr Tyr Ile Phe Trp Tyr Lys Gln Leu Pro Ser Lys Glu
    50                  55                  60

Met Ile Phe Leu Ile Arg Gln Gly Ser Asp Glu Gln Asn Ala Lys Ser
65                  70                  75                  80

Gly Arg Tyr Ser Val Asn Phe Lys Lys Ala Val Lys Ser Val Ala Leu
                85                  90                  95

Thr Ile Ser Ala Leu Gln Leu Glu Asp Ser Ala Lys Tyr Phe Cys Ala
            100                 105                 110

Leu Gly Val Gln Ala Leu Leu Pro Ile Leu Gly Asp Thr Thr Asp Lys
        115                 120                 125

Leu Ile Phe Gly Lys Gly Thr Arg Val Thr Val Glu Pro Arg Ser Gln
130                 135                 140

Pro His Thr Lys Pro Ser Val Phe Val Met Lys Asn Gly Thr Asn Val
145                 150                 155                 160

Ala Cys Leu Val Lys Glu Phe Tyr Pro Lys Asp Ile Arg Ile Asn Leu
                165                 170                 175
```

```
Val Ser Ser Lys Lys Ile Thr Glu Phe Asp Pro Ala Ile Val Ile Ser
            180                 185                 190

Pro Ser Gly Lys Tyr Asn Ala Val Lys Leu Gly Lys Tyr Glu Asp Ser
        195                 200                 205

Asn Ser Val Thr Cys Ser Val Gln His Asp Asn Lys Thr Val His Ser
    210                 215                 220

Thr Asp Phe Glu Val Lys Thr Asp Ser Thr Asp His Val Lys Pro Lys
225                 230                 235                 240

Glu Thr Glu Asn Thr Lys Gln Pro Ser Lys Ser Cys His Lys Pro Lys
                245                 250                 255

Ala Ile Val His Thr Glu Lys Val Asn Met Met Ser Leu Thr Val Leu
            260                 265                 270

Gly Leu Arg Met Leu Phe Ala Lys Thr Val Ala Val Asn Phe Leu Leu
        275                 280                 285

Thr Ala Lys Leu Phe Phe Leu
    290                 295

<210> SEQ ID NO 63
<211> LENGTH: 930
<212> TYPE: DNA
<213> ORGANISM: Homo sapiens

<400> SEQUENCE: 63
atgcagtggg ccctagcggt gcttctagct ttcctgtctc ctgccagtca gaaatcttcc      60
aacttggaag ggagaacgaa gtcagtcatc aggcagactg ggtcatctgc tgaaatcact     120
tgtgatcttg ctgaaggaag taccggctac atccactggt acctacacca ggaggggaag     180
gccccacagc gtcttctgta ctatgactcc tacacctcca cgttgtgtt ggaatcagga      240 atcagcccag ggaagtatga tacttatgga agcacaagga gaacttgag aatgatactg      300 cgaaatctta ttgaaaatga ctctggagtc tattactgtg ccacctggga aactcaagag     360
ttgggcaaaa aaatcaaggt atttggtccc ggaacaaagc ttatcattac agataaacaa     420
cttgatgcag atgtttcccc caagcccact attttctcc cttcaattgc tgaaacaaag      480
ctccagaagg ctgaacata cctttgtctt cttgagaaat ttttccctga tgttattaag      540
atacattggc aagaaaagaa gagcaacacg attctgggat cccaggaggg aacaccatg      600 aagactaacg acacatacat gaaatttagc tggttaacgg tgccagaaaa gtcactggac     660
aaagaacaca gatgtatcgt cagacatgag aataataaaa acggagttga tcaagaaatt     720
atctttcctc aataaagac agatgtcatc acaatggatc ccaaagacaa ttgttcaaaa     780
gatgcaaatg atacactact gctgcagctc acaaacacct ctgcatatta catgtacctc     840
ctcctgctcc tcaagagtgt ggtctatttt gccatcatca cctgctgtct gcttagaaga     900
acggctttct gctgcaatgg agagaaatca                                      930

<210> SEQ ID NO 64
<211> LENGTH: 885
<212> TYPE: DNA
<213> ORGANISM: Homo sapiens

<400> SEQUENCE: 64
atgctgttct ccagcctgct gtgtgtattt gtggccttca gctactctgg atcaagtgtg      60
gcccagaagg ttactcaagc ccagtcatca gtatccatgc cagtgaggaa agcagtcacc     120
ctgaactgcc tgtatgaaac aagttggtgg tcatattata tttttttggta caagcaactt     180
```

```
cccagcaaag agatgatttt ccttattcgc cagggttctg atgaacagaa tgcaaaaagt    240
ggtcgctatt ctgtcaactt caagaaagca gtgaaatccg tcgccttaac catttcagcc    300
ttacagctag aagattcagc aaagtacttt tgtgctcttg gggtccaagc cctcctaccc    360
atactggggg ataccaccga taaactcatc tttggaaaag aacccgtgt gactgtggaa     420
ccaagaagtc agcctcatac caaccatcc gttttgtca tgaaaatgg aacaaatgtc       480
gcttgtctgg tgaaggaatt ctaccccaag gatataagaa taaatctcgt gtcatccaag    540
aagataacag agtttgatcc tgctattgtc atctctccca gtgggaagta caatgctgtc    600
aagcttggta aatatgaaga ttcaaattca gtgacatgtt cagttcaaca cgacaataaa    660
actgtgcact ccactgactt tgaagtgaag acagattcta cagatcacgt aaaaccaaag    720
gaaactgaaa acacaaagca accttcaaag agctgccata aacccaaagc catagttcat    780
accgagaagg tgaacatgat gtccctcaca gtgcttgggc tacgaatgct gtttgcaaag    840
actgttgccg tcaattttct cttgactgcc aagttatttt tcttg                    885

<210> SEQ ID NO 65
<211> LENGTH: 17
<212> TYPE: PRT
<213> ORGANISM: Homo sapiens

<400> SEQUENCE: 65

Cys Ala Ala Gln Ile Tyr Asn Gln Gly Gly Lys Leu Ile Phe Gly Gln
1               5                   10                  15

Gly

<210> SEQ ID NO 66
<211> LENGTH: 13
<212> TYPE: PRT
<213> ORGANISM: Homo sapiens

<400> SEQUENCE: 66

Cys Val Val Thr Gly Asn Gln Phe Tyr Phe Gly Thr Gly
1               5                   10

<210> SEQ ID NO 67
<211> LENGTH: 18
<212> TYPE: PRT
<213> ORGANISM: Homo sapiens

<400> SEQUENCE: 67

Cys Ala Leu Ser Glu Glu Pro Ser Asn Thr Gly Lys Leu Ile Phe Gly
1               5                   10                  15

Gln Gly

<210> SEQ ID NO 68
<211> LENGTH: 15
<212> TYPE: PRT
<213> ORGANISM: Homo sapiens

<400> SEQUENCE: 68

Cys Ala Val Met Asp Ser Ser Tyr Lys Leu Ile Phe Gly Ser Gly
1               5                   10                  15

<210> SEQ ID NO 69
<211> LENGTH: 17
<212> TYPE: PRT
<213> ORGANISM: Homo sapiens

<400> SEQUENCE: 69
```

Cys Ala Ala Gly Gly Thr Ser Tyr Gly Lys Leu Thr Phe Gly Gln
1               5                   10                  15

Gly

<210> SEQ ID NO 70
<211> LENGTH: 20
<212> TYPE: PRT
<213> ORGANISM: Homo sapiens

<400> SEQUENCE: 70

Cys Ala Glu Thr Trp Thr Asp Arg Gly Ser Thr Leu Gly Arg Leu Tyr
1               5                   10                  15

Phe Gly Arg Gly
            20

<210> SEQ ID NO 71
<211> LENGTH: 17
<212> TYPE: PRT
<213> ORGANISM: Homo sapiens

<400> SEQUENCE: 71

Cys Ala Ala Ser Leu Tyr Asn Gln Gly Gly Lys Leu Ile Phe Gly Gln
1               5                   10                  15

Gly

<210> SEQ ID NO 72
<211> LENGTH: 15
<212> TYPE: PRT
<213> ORGANISM: Homo sapiens

<400> SEQUENCE: 72

Cys Ala Ser Gly Asp Ser Gly Tyr Ala Leu Asn Phe Gly Lys Gly
1               5                   10                  15

<210> SEQ ID NO 73
<211> LENGTH: 20
<212> TYPE: PRT
<213> ORGANISM: Homo sapiens

<400> SEQUENCE: 73

Cys Ala Leu Thr Ile Trp Asp Tyr Gly Gly Ser Gln Gly Asn Leu Ile
1               5                   10                  15

Phe Gly Lys Gly
            20

<210> SEQ ID NO 74
<211> LENGTH: 15
<212> TYPE: PRT
<213> ORGANISM: Homo sapiens

<400> SEQUENCE: 74

Cys Ala Gly Glu Asn Ser Gly Tyr Ala Leu Asn Phe Gly Lys Gly
1               5                   10                  15

<210> SEQ ID NO 75
<211> LENGTH: 17
<212> TYPE: PRT
<213> ORGANISM: Homo sapiens

<400> SEQUENCE: 75

Cys Ala Met Ser Leu Ser Gly Gly Ser Tyr Ile Pro Thr Phe Gly Arg
1               5                   10                  15

Gly

<210> SEQ ID NO 76
<211> LENGTH: 21
<212> TYPE: PRT
<213> ORGANISM: Homo sapiens

<400> SEQUENCE: 76

Cys Ala Gly Gln Leu Gly Gly Ala Gly Gly Thr Ser Tyr Gly Lys Leu
1               5                   10                  15

Thr Phe Gly Gln Gly
            20

<210> SEQ ID NO 77
<211> LENGTH: 18
<212> TYPE: PRT
<213> ORGANISM: Homo sapiens

<400> SEQUENCE: 77

Cys Ala Ala Asn Trp Ser Pro Gln Gly Asn Glu Lys Leu Thr Phe Gly
1               5                   10                  15

Thr Gly

<210> SEQ ID NO 78
<211> LENGTH: 15
<212> TYPE: PRT
<213> ORGANISM: Homo sapiens

<400> SEQUENCE: 78

Cys Ala Ser Met Asp Ser Asn Tyr Gln Leu Ile Trp Gly Ala Gly
1               5                   10                  15

<210> SEQ ID NO 79
<211> LENGTH: 18
<212> TYPE: PRT
<213> ORGANISM: Homo sapiens

<400> SEQUENCE: 79

Cys Val Val Asn Arg Phe Thr Arg Asp Gly Asn Lys Leu Val Phe Gly
1               5                   10                  15

Ala Gly

<210> SEQ ID NO 80
<211> LENGTH: 15
<212> TYPE: PRT
<213> ORGANISM: Homo sapiens

<400> SEQUENCE: 80

Cys Ala Ser Ser Phe Ser Ser Gly Lys Gln Tyr Phe Gly Pro Gly
1               5                   10                  15

<210> SEQ ID NO 81
<211> LENGTH: 19
<212> TYPE: PRT
<213> ORGANISM: Homo sapiens

<400> SEQUENCE: 81

Cys Ala Thr Ser Asp Val Gly Thr Gly Asp Thr Gly Glu Leu Phe Phe
1               5                   10                  15

Gly Glu Gly

<210> SEQ ID NO 82
<211> LENGTH: 19
<212> TYPE: PRT
<213> ORGANISM: Homo sapiens

<400> SEQUENCE: 82

Cys Ala Ser Ser Arg Leu Leu Ala Gly Gly Gln Asn Glu Gln Phe Phe
1               5                   10                  15

Gly Pro Gly

<210> SEQ ID NO 83
<211> LENGTH: 18
<212> TYPE: PRT
<213> ORGANISM: Homo sapiens

<400> SEQUENCE: 83

Cys Ala Ser Ser Glu Val Thr Gly Gly Tyr Asn Glu Gln Phe Phe Gly
1               5                   10                  15

Pro Gly

<210> SEQ ID NO 84
<211> LENGTH: 19
<212> TYPE: PRT
<213> ORGANISM: Homo sapiens

<400> SEQUENCE: 84

Cys Ser Val Gly Ala Gly Gln Gly Pro Tyr Thr Asp Thr Gln Tyr Phe
1               5                   10                  15

Gly Pro Gly

<210> SEQ ID NO 85
<211> LENGTH: 19
<212> TYPE: PRT
<213> ORGANISM: Homo sapiens

<400> SEQUENCE: 85

Cys Ala Ser Ser Leu Gly Ala Thr Gly Ala Asn Glu Lys Leu Phe Phe
1               5                   10                  15

Gly Ser Gly

<210> SEQ ID NO 86
<211> LENGTH: 15
<212> TYPE: PRT
<213> ORGANISM: Homo sapiens

<400> SEQUENCE: 86

Cys Ala Ser Ser Tyr Arg Gly Thr Glu Ala Phe Phe Gly Gln Gly
1               5                   10                  15

<210> SEQ ID NO 87
<211> LENGTH: 17
<212> TYPE: PRT
<213> ORGANISM: Homo sapiens

<400> SEQUENCE: 87

Cys Ala Ser Ser Phe Asp Val Gly Leu Pro Pro Leu His Phe Gly Asn
1               5                   10                  15

Gly

<210> SEQ ID NO 88
<211> LENGTH: 15
<212> TYPE: PRT

<213> ORGANISM: Homo sapiens

<400> SEQUENCE: 88

Cys Ala Thr Ser Arg Glu Trp Glu Thr Gln Tyr Phe Gly Pro Gly
1               5                   10                  15

<210> SEQ ID NO 89
<211> LENGTH: 21
<212> TYPE: PRT
<213> ORGANISM: Homo sapiens

<400> SEQUENCE: 89

Cys Ala Ser Ser Gln Leu Tyr Arg Asp Thr Ser Asn Thr Gly Glu Leu
1               5                   10                  15

Phe Phe Gly Glu Gly
            20

<210> SEQ ID NO 90
<211> LENGTH: 21
<212> TYPE: PRT
<213> ORGANISM: Homo sapiens

<400> SEQUENCE: 90

Cys Ala Ser Gly Ile Ser Gly Thr Ala Ser Ser Tyr Asn Ser Pro Leu
1               5                   10                  15

His Phe Gly Asn Gly
            20

<210> SEQ ID NO 91
<211> LENGTH: 18
<212> TYPE: PRT
<213> ORGANISM: Homo sapiens

<400> SEQUENCE: 91

Cys Ala Ser Ser Val Gly Gly Gly Leu Ala Asp Thr Gln Tyr Phe Gly
1               5                   10                  15

Pro Gly

<210> SEQ ID NO 92
<211> LENGTH: 19
<212> TYPE: PRT
<213> ORGANISM: Homo sapiens

<400> SEQUENCE: 92

Cys Ala Ser Ser Glu Tyr Ile Gln Tyr Ser Gly Asn Thr Ile Tyr Phe
1               5                   10                  15

Gly Glu Gly

<210> SEQ ID NO 93
<211> LENGTH: 22
<212> TYPE: PRT
<213> ORGANISM: Homo sapiens

<400> SEQUENCE: 93

Cys Ser Ala Lys Val Thr Ser Gly Gln His Gln Gly Thr Thr Asp Thr
1               5                   10                  15

Gln Tyr Phe Gly Pro Gly
            20

<210> SEQ ID NO 94
<211> LENGTH: 15
<212> TYPE: PRT

<213> ORGANISM: Homo sapiens

<400> SEQUENCE: 94

Cys Ser Val Glu Gly Arg Gly Tyr Glu Gln Tyr Phe Gly Pro Gly
1               5                   10                  15

<210> SEQ ID NO 95
<211> LENGTH: 19
<212> TYPE: PRT
<213> ORGANISM: Homo sapiens

<400> SEQUENCE: 95

Cys Ala Thr Trp Glu Thr Gln Glu Leu Gly Lys Lys Ile Lys Val Phe
1               5                   10                  15

Gly Pro Gly

<210> SEQ ID NO 96
<211> LENGTH: 24
<212> TYPE: PRT
<213> ORGANISM: Homo sapiens

<400> SEQUENCE: 96

Cys Ala Leu Gly Val Gln Ala Leu Leu Pro Ile Leu Gly Asp Thr Thr
1               5                   10                  15

Asp Lys Leu Ile Phe Gly Lys Gly
            20

<210> SEQ ID NO 97
<211> LENGTH: 22
<212> TYPE: DNA
<213> ORGANISM: Artificial Sequence
<220> FEATURE:
<223> OTHER INFORMATION: Primer

<400> SEQUENCE: 97
ctcggcaggc cgagccacgg gc                                             22

<210> SEQ ID NO 98
<211> LENGTH: 22
<212> TYPE: DNA
<213> ORGANISM: Artificial Sequence
<220> FEATURE:
<223> OTHER INFORMATION: Primer

<400> SEQUENCE: 98
gcccgtggct cggcctgccg ag                                             22

<210> SEQ ID NO 99
<211> LENGTH: 27
<212> TYPE: DNA
<213> ORGANISM: Artificial Sequence
<220> FEATURE:
<223> OTHER INFORMATION: Primer

<400> SEQUENCE: 99
ctcgagatgt ctcgctccgt ggcctta                                        27

<210> SEQ ID NO 100
<211> LENGTH: 32
<212> TYPE: DNA
<213> ORGANISM: Artificial Sequence
<220> FEATURE:
<223> OTHER INFORMATION: Primer

<400> SEQUENCE: 100

```
gtgtgagttt tgtcgctagc ctgggggacc tg                                32

<210> SEQ ID NO 101
<211> LENGTH: 32
<212> TYPE: DNA
<213> ORGANISM: Artificial Sequence
<220> FEATURE:
<223> OTHER INFORMATION: Primer

<400> SEQUENCE: 101
caggtccccc aggctagcga caaaactcac ac                                32

<210> SEQ ID NO 102
<211> LENGTH: 31
<212> TYPE: DNA
<213> ORGANISM: Artificial Sequence
<220> FEATURE:
<223> OTHER INFORMATION: Primer

<400> SEQUENCE: 102
gcggccgctc atttacccgg agacagggag a                                 31
```

MR1 RESTRICTED T CELL RECEPTORS FOR CANCER IMMUNOTHERAPY

CROSS-REFERENCE TO RELATED APPLICATIONS

This is a continuation-in-part of International Patent Application No. PCT/EP2018/055620 filed Mar. 7, 2018, which claims the benefit of European Patent Application Nos. EP 17159754.5 filed Mar. 7, 2017 and EP17179309.4 filed Jul. 3, 2017. Benefit is also claimed to European Patent Application No. EP 18194025.5, filed Sep. 12, 2018. The foregoing patent applications are incorporated by reference herein in their entirety.

FIELD

The invention relates to the identification of tumour-reactive human T cell antigen receptors (TCRs) restricted to the non-polymorphic antigen-presenting molecule MR1. The functional TCR transcript sequences were isolated from clones representative of a novel population of human T cells (discovered by the inventors and termed MR1T cells) reacting to MR1-expressing tumour cells in the absence of any added foreign antigen and in MR1-dependent manner. The invention also relates to the use of MR1-restricted tumour-reactive TCR gene sequences in cancer treatment.

BACKGROUND OF THE INVENTION

T lymphocytes can detect a diverse range of non-peptide antigens including lipids and phosphorylated isoprenoids, presented by non-polymorphic cell surface molecules. The heterogeneous phenotypic and functional properties of these T cells support specialized roles in host protection against infections, autoimmunity, and cancer. The repertoire of T cells specific for non-peptide antigens recently increased to include mucosal associated invariant T (MAIT) cells, which respond to small riboflavin precursors produced by a wide range of yeasts and bacteria, and presented by the MHC class I-related protein MR1. MAIT cells are frequent in human blood, kidney and intestine, and comprise a major fraction of T cells resident in the liver. Following activation, MAIT cells release an array of pro-inflammatory and immunomodulatory cytokines, and can mediate direct killing of microbe-infected cells. It remains unknown whether the role of MR1 extends beyond presentation of microbial metabolites to MAIT cells.

MR1 is a non-polymorphic MHC class I-like protein that is expressed at low levels on the surface of many cell types. MR1 is highly conserved across multiple species, with human and mouse MR1 sharing >90% sequence homology at the protein level.

The inventors proposed the existence of human T cells that recognize tumour-associated antigens presented by MR1. These novel T cells might participate in tumour immune surveillance, thus representing novel tools for cancer immunotherapy. Adoptive therapy with donor- or patient-derived T cells engineered to express TCRs specific for selected tumour-associated antigens represents a promising and safe strategy to induce clinically relevant anti-tumour immune response in cancer patients. Nevertheless, the majority of the so far identified tumour-associated antigens are peptides presented by polymorphic MHC molecules. The extreme polymorphism of MHC genes limits the application of this approach to those patients expressing unique MHC alleles. Targeting tumour-antigens bound to non-polymorphic antigen presenting molecules, such as MR1, might overcome this constraint and in principle be applicable to all patients bearing tumours expressing MR1. The use of tumour-reactive T cell receptors that recognize MR1-presented antigens might also have the advantage of complementing anti-tumour responses mediated by MHC-presented peptide antigens, excluding cross-competition of tumour antigens for binding to the same type of presenting molecule. In addition, this strategy may provide the possibility of targeting antigens of different nature on the same tumour cells, thus minimizing the potential occurrence of tumour escape variants under selective immune pressure. Therefore, the identification of MR1-presented tumour-associated antigens and the characterization of MR1-restricted TCRs recognizing these antigens might have important implications for cancer immunotherapy.

Based on this state of the art, the objective of the present invention is to provide novel means and methods of treatment for cancer. This objective is attained by the subject matter of the independent claims, with further advantageous solutions provided by the dependent claims, examples and figures disclosed herein.

SUMMARY OF THE INVENTION

In the broadest sense, the invention relates to a method of treatment of cancer, wherein TCR sequences isolated from T cells reactive to MR1-expressing cancer cells (MR1T cells) are expressed after gene transfer into a population of a patient's T cells. These foreign, transgenically expressed TCR sequences are used for conferring specific recognition of MR1-expressing cancer cells to T cells as a treatment of the patient's tumour.

The invention similarly provides a T cell, and T cell preparations comprising a plurality of T cells, transduced with MR1T cell specific TCR genes. In certain embodiments, the T cells transduced with MR1T cell TCR genes can be used for adoptive cell immunotherapy in combination with other therapeutic interventions.

The invention also relates to a research method facilitating the identification of the TCR sequences isolated from T cells reactive to MR1-expressing cancer cells (MR1T cells) employed in the invention. This encompasses a method to isolate MR1-restricted T cells that recognize tumour-associated antigens. T cells from peripheral blood of normal donors or from cancer patients are stimulated with tumor cell lines representing the same type of tumor in patient. These tumor cell lines are transfected with the MR1 gene and thus express large amounts of MR1 protein on their plasma membrane. Activated T cells are sorted for expression of activation markers, (e.g. CD137, or CD150, or CD69, or ICOS) and are cloned as published (De Libero, Methods for the generation of T cell clones and epithelial cell lines from excised human biopsies or needle aspirates. In MHC 123-140 (IRL, Oxford; 1997)). Individual clones are tested for their capacity to recognize tumor cells in an MR1-restricted manner, for killing tumor cells and for release of inflammatory cytokines. The TCR genes of MR1-restricted and tumor-specific T cell clones are sequenced and identified.

The invention also relates to a method by which tumor-infiltrating T cells are prepared from the same cancer tissue biopsies according to our previously established protocol (De Libero, ibid.). Individual T cell clones are tested against a panel of tumor cell lines expressing MR1 protein. The most reactive T cell clones are studied for their MR1 restriction, tumor killing and release of inflammatory cytokines. The TCR genes of selected T cell clones are sequenced.

Figures 1A, 1B, 1C, 1D, 1E:
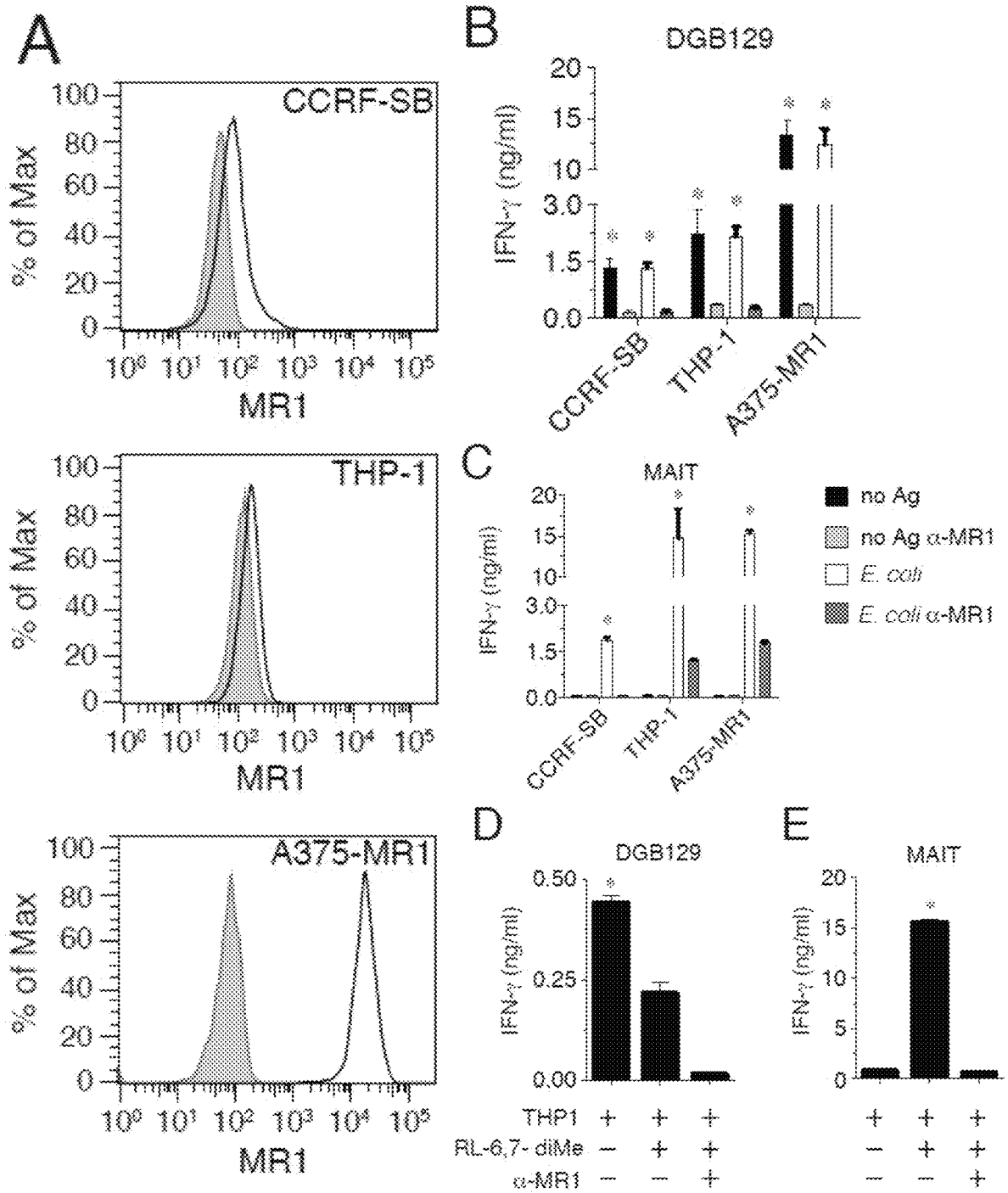
FIGS. 1A-1E. MR1T cells do not recognize microbial antigens. (A) Surface expression of MR1 by CCRFSB, THP-1 and A375-MR1 cells. Grey histograms indicate staining with isotype-matched control mAbs. Stimulation of (B) MR1T cell clone DGB129 or (C) MAIT cell clone SMC3 by the three cell lines in A in the absence (no Ag) or presence of E. coli lysate (E. coli) and/or anti-MR1 blocking mAbs (α-MR1). The MAIT clone SMC3 was previously isolated from PBMC of a healthy donor and expresses canonical MAIT phenotype and function. Columns indicate IFN-γ release (mean+SD). Stimulation of (D) DGB129 MR1T or (E) SMC3 MAIT cells by THP-1 cells, constitutively expressing surface MR1, loaded with synthetic 6,7-dimethyl-8-D-ribityllumazine (RL-6,7-diMe) with or without anti-MR1 mAbs. Columns indicate mean IFN-γ release+SD. Data are representative of four (A, B and C), two (D and E). * P<0.05 (Unpaired Student's t-test).

P<0.0001 (Unpaired Student's t-test).

DETAILED DESCRIPTION OF THE INVENTION

Definitions

The term MR1 in the context of the present specification refers to either the MR1 gene (Entrez 3140) or the MR1 gene product (Uniprot Q95460).

MR1 in the physiological context of a non-tumour bearing patient presents bacterial riboflavin by-products (above referred to as "exogenous microbial-derived antigens") and presents them to mucosal invariant T cells.

An MR1-expressing cancer cell presents a particular cancer antigen, or a number of particular cancer antigens, on MR1.

The term MR1T cell in the context of the present specification refers to a T cell that expresses a T cell receptor capable of binding specifically to an MR1 molecule presented by a cancer cell.

The term MR1T cell receptor in the context of the present specification refers to a T cell receptor capable of binding specifically to an antigen presented by a cancer cell in association with an MR1 molecule.

A TCR sequence or TCR molecule described herein comprises, to be fully functional, a TCR alpha and a TCR beta polypeptide chain, or a TCR gamma and a TCR delta polypeptide chain.

If reference is made to a TCR alpha or beta polypeptide having a particular sequence, it is understood that in order for this to be fully functional in the methods and cells described herein, it requires the presence of a complementary (beta or alpha, respectively) polypeptide chain. The same applies, mutatis mutandis, to the gamma delta pairing. Mention of a specific TCR alpha, beta, gamma or delta sequence implies the possibility that it is paired with the TCR sequence with which it is paired in the original clone as described herein, or a sequence of certain identity to the original pairing sequence, as specified herein. Mention of a specific TCR alpha, beta, gamma or delta sequence also implies the possibility that it is paired with another pairing TCR sequence.

The recognition of MR1-presented cancer antigens is effected mainly through CDR3 sequences. Wherein a TCR sequence characterized only by a specific CDR3 sequence is mentioned herein, it is implied that the TCR sequence is a full alpha, beta, gamma or delta sequence as provided herein, and a resulting TCR molecule is paired with an appropriate second sequence.

In the context of the present specification, the terms sequence identity and percentage of sequence identity refer to a single quantitative parameter representing the result of a sequence comparison determined by comparing two aligned sequences position by position. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless stated otherwise, sequence identity values provided herein refer to the value obtained using the BLAST suite of programs (Altschul et al., J. Mol. Biol. 215:403-410 (1990)) using the above identified default parameters for protein and nucleic acid comparison, respectively. Reference to identical sequences without specification of a percentage value implies 100% identical sequences (i.e. the same sequence).

In the present specification, the term positive, when used in the context of expression of a marker, refers to expression of an antigen assayed by a fluorescent labelled antibody, wherein the fluorescence is at least 30% higher 30%), particularly 50% or 80%, in median fluorescence intensity in comparison to staining with an isotype-matched antibody which does not specifically bind the same target. Such expression of a marker is indicated by a superscript "plus" (+), following the name of the marker, e.g. $CD4^+$.

In the present specification, the term negative, when used in the context of expression of a marker, refers to expression of an antigen assayed by a fluorescent labelled antibody, wherein the median fluorescence intensity is less than 30% higher, particularly less than 15% higher, than the median fluorescence intensity of an isotype-matched antibody which does not specifically bind the same target. Such expression of a marker is indicated by a superscript minus (−), following the name of the marker, e.g. $CD127^-$.

The term nucleic acid expression vector in the context of the present specification relates to a plasmid or a viral genome, which is used to transfect (in case of a plasmid) or transduce (in case of a viral genome) a target cell with a certain gene of interest. The gene of interest is under control of a promoter sequence and the promoter sequence is operational inside the target cell, thus, the gene of interest is transcribed either constitutively or in response to a stimulus or dependent on the cell's status. In certain embodiments, the viral genome is packaged into a capsid to become a viral vector, which is able to transduce the target cell.

A first aspect of the invention relates to a method of identifying and/or isolating a T cell that expresses a T cell receptor capable of binding specifically to a cancer antigen presented by a cancer cell in association with a non-polymorphic MHC I-related MR1 antigen-presenting molecule. This method comprises the steps of
a. providing a preparation of T cells isolated from a patient or a healthy donor, then
b. contacting, particularly co-culturing, this preparation of isolated T cells with cancer cells expressing MR1 protein in the absence of exogenous microbial-derived antigens in a contacting step, then
c. isolating a T cell that is specifically reactive to said cancer cells in an MR1-dependent manner in an isolation step.

In certain embodiments, the contacting step comprises an expansion step, wherein the preparation of isolated T cells is expanded in the presence of cancer cells expressing MR1. In certain particular embodiments, the cancer cells are irradiated in order to prohibit their growth prior to being brought into contact with the T cells. This is going to be advantageous if the two cell types are meant to be kept in co-culture for extended periods of time and overgrowing of the culture by the cancer cells is to be avoided.

In other settings, particularly in clinical use (see below), where culturing times are short, the cancer cells may be used without irradiation.

In certain embodiments, the expansion step is conducted in the presence of IL-2, IL-7 and IL-15.

In certain embodiments, the isolation step comprises staining with one or more ligands, in particular one or more (monoclonal) antibodies specific for a cell surface marker selected from CD3, CD69, CD137, CD150, and/or ICOS). In particularly preferred embodiments the isolation step comprises selecting $CD3^+CD137^+$, and/or $CD3^+CD69^+$, and/or $CD3^+CD150^+$, and/or $CD3^+ICOS^+$ T cells, followed by flow cytometric analysis and cell sorting, particularly by using FACS or magnetic separation (MACS). Here positive expression (+) of a marker means at least 30% increase of the median fluorescence intensity over staining with isotype-matched antibody which does not specifically bind the same cell. In other words, T cells that express CD3 and CD137, and/or CD3 and CD69, and/or CD3 and CD150, and/or CD3 and ICOS are isolated using FACS or MACS. The skilled person is aware that in instances where the cells are isolated via FACS, cells that are positive for the expression of two (or more) different markers can be isolated in a single step. If magnetic separation is used, two separate steps have to be performed to isolate cells that are positive for the expression of two different markers.

The isolating step comprises selecting T cells that display MR1-restricted activity. In other words, this step comprises isolating T cells that are activated by an antigen presented on MR1.

In certain embodiments, the isolating step comprises selecting T cells that exhibit 2× increased expression of a cytokine selected from IFN-γ and/or GM-CSF release when stimulated with cells expressing MR1 compared to stimulation with cells not expressing MR1.

The skilled person is aware that an MR1-expressing cancer cell presents a particular cancer antigen, or a number of particular cancer antigens, on MR1.

In certain embodiments, the isolating step comprises selecting T cells that exhibit 2× increased expression of a cytokine selected from IFN-γ and/or GM-CSF release when stimulated with tumour cells expressing MR1 compared to stimulation with tumour cells (of the same origin, or same cell line) not expressing MR1.

Reactive cells are those that, in response to being contacted by an MR1-expressing cancer cell (presenting a cancer antigen in an MR1-restricted fashion), upregulate activation markers (particularly the markers cited in the preceding paragraphs), release cytokines and start to proliferate.

In other words, T cells that display MR1-restricted activity are T cells that can be activated by a tumour-associated antigen displayed by MR1.

These cells can be sorted by fluorescence activated cell sorting (FACS) after staining with the appropriate fluorescently labelled antibodies specific for the marker, or by sorting by magnetic beads labelled with the appropriate antibodies (which is the usual sorting method in a clinical setting).

In certain embodiments, the isolating step comprises expanding individual clones of the cells sorted as a function of their activation status, and then selecting T cell clones that display MR1-restricted activity, particularly cells that exhibit 2× increased expression of a cytokine selected from IFN-γ and/or GM-CSF when stimulated with cells expressing MR1 compared to stimulation with cells not expressing MR1.

In certain embodiments, the method further includes determining a nucleic acid sequence encoding a T cell receptor of the T cell isolated in the isolation step. In certain embodiments, the method includes determining two nucleic acid sequences encoding both T cell receptor chains of the T cell isolated in the isolation step.

Another aspect of the invention relates to a method of producing a preparation of transgenic MR1T cells reactive to MR1 in the absence of exogenous antigens. The method encompasses firstly, determining which T cell receptors are most likely to be reactive to a particular MR1-expressing cancer in a patient, then preparing a T cell population expressing these specific T cell receptor genes from expression constructs transferred into the cells, and administering these engineered T cells into the patient.

This method comprises the steps of
a. providing a tumour sample obtained from a patient;
b. contacting said tumour sample with a plurality of MR1T cell receptor molecule reactive to MR1, either presented on a plurality of T cell clones, wherein each T cell clone is characterized by an MR1T cell receptor molecule reactive to MR1; or
as soluble MR1T cell receptor molecules that are labelled, and their recognition is assayed in a non-cell-dependent fashion;
c. identifying a number of T cell clone(s) specifically reactive to said tumour sample;
d. providing a T cell preparation, particularly a T cell preparation obtained from the same patient;
e. introducing a nucleic acid expression construct encoding an MR1-reactive T cell receptor molecule expressed on a T cell clone identified as being specifically reactive to said tumour sample in step c into said T cell preparation, yielding a transgene T cell preparation.

The transgene T cell preparation to the patient could thus be administered to the patient.

In certain embodiments, each of the MR1-specific T cell clones or isolated, soluble monomeric or labelled and multimerized soluble T cell receptors is characterized by a CDR3 sequence tract selected from any one of SEQ ID NO 065 to SEQ ID NO 096. Likewise, the CDR3 sequence tract can be characterized by a sequence identical to a sequence selected from any one of SEQ ID NO 065 to SEQ ID NO 096 with one or two amino acid substitutions. In particular embodiments, the substitutions made to the CDR3 sequence are selected according to the following substitution rules:

glycine (G) and alanine (A) are interchangeable; valine (V), leucine (L), and isoleucine (I) are interchangeable, A and V are interchangeable;
tryptophan (W) and phenylalanine (F) are interchangeable, tyrosine (Y) and F are interchangeable;
serine (S) and threonine (T) are interchangeable;
aspartic acid (D) and glutamic acid (E) are interchangeable
asparagine (N) and glutamine (Q) are interchangeable; N and S are interchangeable; N and D are interchangeable; E and Q are interchangeable;
methionine (M) and Q are interchangeable;
cysteine (C), A and S are interchangeable;
proline (P), G and A are interchangeable;
arginine (R) and lysine (K) are interchangeable.

In certain embodiments, each of the MR1-specific T cell clones or isolated, labelled and multimerized soluble T cell receptors is characterized by a CDR3 sequence tract selected from any one of SEQ ID NO 065 to SEQ ID NO 096 wherein the sequence comprises a maximum total of 0, 1, or 2 substitutions in the three N and/or C terminal positions according to the above substitution rules in the three N and/or C terminal positions, whereas the central amino acids of the CDR3 sequence as indicated are not changed It is known that the central part of the CDR3 sequence contributes most to antigen binding or recognition specificity.

In certain embodiments, each of the MR1-specific T cell clones or isolated, labelled and multimerized soluble T cell receptors is characterized by a nucleic acid sequence selected from SEQ ID NO 007 to SEQ ID NO 012 or SEQ ID NO 037 to SEQ ID NO 060 or SEQ ID NO 063 to SEQ ID NO 064 and/or an amino acid sequence selected from SEQ ID NO 001 to SEQ ID 006 or SEQ ID NO 013 to SEQ ID NO 036 or SEQ ID NO 061 to SEQ ID NO 062.

In certain embodiments, each of the MR1-specific T cell clones or isolated, labelled and multimerized soluble T cell receptors is characterized by "The same biological activity" in this context refers to the ability of a recombinant TCR sequence to recognize (or contribute in the recognition of) an MR1 molecule presenting a cancer antigen on a cancer cell. Assays and methods to determine such interaction are described herein.

In certain embodiments, each of the MR1-specific T cell clones or isolated, labelled and multimerized soluble T cell receptors is characterized by a T cell receptor α chain nucleic acid sequence selected from SEQ ID NO 007, 009 to 011 or SEQ ID NO 037 to SEQ ID NO 048 and/or an amino acid sequence selected from SEQ ID NO 001, 003 to 005 or SEQ ID NO 013 to SEQ ID NO 024.

In certain embodiments, each of the MR1-specific T cell clones or isolated, soluble monomeric or labelled and multimerized soluble T cell receptors is characterized by a T cell receptor α chain amino acid sequence at least 85% (≥90%, 95%, 98) identical to SEQ ID NO 001, 003 to 005 or SEQ ID NO 013 to SEQ ID NO 024 and having the same biological activity, particularly an amino acid sequence at least 85% (≥90%, 95%, 98) identical to SEQ ID NO 001, 003 to 005 or SEQ ID NO 013 to SEQ ID NO 024 comprising a CDR sequence selected from SEQ ID NO 065 to SEQ ID NO 079

In certain embodiments, each of the MR1-specific T cell clones or isolated, labelled and multimerized soluble T cell receptors is characterized by a T cell receptor β chain nucleic acid sequence selected from SEQ ID NO 008, 010 to 012 or SEQ ID NO 049 to SEQ ID NO 060 and/or an amino acid sequence selected from SEQ ID NO 002, 004 to 006 or SEQ ID NO 025 to SEQ ID NO 036.

In certain embodiments, each of the MR1-specific T cell clones or isolated, labelled and multimerized soluble T cell receptors is characterized by a T cell receptor β chain amino acid sequence at least 85% (≥90%, 95%, 98) identical to SEQ ID SEQ ID NO 002, 004 to 006 or SEQ ID NO 025 to SEQ ID NO 036 and having the same biological activity, particularly an amino acid sequence at least 85% (≥90%, 95%, 98) identical to SEQ ID NO 002, 004 to 006 or SEQ ID NO 025 to SEQ ID NO 036 comprising a CDR sequence selected from SEQ ID NO 080 to SEQ ID NO 094.

In certain embodiments, each of the MR1-specific T cell clones or isolated, labelled and multimerized soluble T cell receptors is characterized by a T cell receptor γ chain nucleic acid sequence SEQ ID NO 61 and/or an amino acid sequence SEQ ID NO 063, or a sequence at least 85% (≥90%, 95%, 98) identical thereto and having the same biological activity, particularly an amino acid sequence at least 85% (≥90%, 95%, 98) identical to SEQ ID NO 063 and comprising a CDR3 of SEQ ID NO 095

In certain embodiments, each of the MR1-specific T cell clones or isolated, labelled and multimerized soluble T cell receptors is characterized by a T cell receptor δ chain nucleic acid sequence SEQ ID NO 64 and/or an amino acid sequence SEQ ID NO 062, or an amino acid sequence at least 85% (≥90%, 95%, 98) identical to SEQ ID NO 062 and comprising a CDR3 of SEQ ID NO 096.

In certain embodiments, each of the MR1-specific T cell clones or isolated, labelled and multimerized soluble T cell receptors is characterized by a T cell receptor α chain and β chain nucleic acid sequence pair selected from the pairs: SEQ ID NO 007 and SEQ ID NO 008, SEQ ID NO 009 and SEQ ID NO 010, SEQ ID NO 011 and SEQ ID NO 012, SEQ ID NO 037 and SEQ ID NO 049, SEQ ID NO 038 and SEQ ID NO 050, SEQ ID NO 039 and SEQ ID NO 051, SEQ ID NO 040 and SEQ ID NO 052, SEQ ID NO 041 and SEQ ID NO 053, SEQ ID NO 042 and SEQ ID NO 054, SEQ ID NO 043 and SEQ ID NO 055, SEQ ID NO 044 and SEQ ID NO 056, SEQ ID NO 045 and SEQ ID NO 057, SEQ ID NO 046 and SEQ ID NO 058, SEQ ID NO 047 and SEQ ID NO 059 or SEQ ID NO 048 and SEQ ID NO 060.

In certain embodiments, each of the MR1-specific T cell clones or isolated, labelled and multimerized soluble T cell receptors is characterized by a T cell receptor γ chain and δ chain nucleic acid sequence pair selected from SEQ ID NO 063 and SEQ ID NO 064, or a sequence at least 85% (≥90%, 95%, 98) identical thereto having the same biological activity as the unmutated pair.

In certain embodiments, each of the MR1-specific T cell clones or isolated, labelled and multimerized soluble T cell receptors is characterized by a T cell receptor α chain and β chain amino acid sequence pair selected from the pairs: SEQ ID NO 001 and SEQ ID NO 002, SEQ ID NO 003 and SEQ ID NO 004, SEQ ID NO 005 and SEQ ID NO 006, SEQ ID NO 013 and SEQ ID NO 025, SEQ ID NO 014 and SEQ ID NO 026, SEQ ID NO 015 and SEQ ID NO 027, SEQ ID NO 016 and SEQ ID NO 028, SEQ ID NO 017 and SEQ ID NO 029, SEQ ID NO 018 and SEQ ID NO 030, SEQ ID NO 019 and SEQ ID NO 031, SEQ ID NO 20 and SEQ ID NO 032, SEQ ID NO 021 and SEQ ID NO 033, SEQ ID NO 022 and SEQ ID NO 034, SEQ ID NO 023 and SEQ ID NO 035, SEQ ID NO 024 and SEQ ID NO 036, or a pair selected from the pairs given in the previous paragraph, wherein each of the partners may have a sequence at least 85% (≥90%, 95%, 98) identical to the indicated SEQ ID NO and the pair has the same biological activity as the unmutated pair.

In particular embodiments, each of the amino acid sequences comprises a CDR3 sequence identical to the indicated SEQ ID NO as can be inferred from the table below.

In certain embodiments, each of the MR1-specific T cell clones or isolated, labelled and multimerized soluble T cell receptors is characterized by a T cell receptor γ chain and δ chain amino acid sequence pair selected from SEQ ID NO 061 and SEQ ID NO 062.

In certain embodiments, the T cell preparation according to the invention is obtained from the same patient (autologous adoptive T cell therapy). This method has the advantage of avoiding the risk of adverse reactions, particularly an allo-immune reaction driven by the endogenous T cell receptors of the engineered T cell preparation.

In certain embodiments, the T cell preparation according to the invention is obtained from another subject, particularly a HLA-matched subject (allogeneic adoptive T cell therapy). While depending on the quality of the HLA match, the risk of alloimmunity may be significant, the logistics and procedural advantages of having a large selection of pre-made TC preparations to select from may facilitate this therapy to a vastly larger patient community in comparison to the far higher costs and regulatory hurdles of a bespoke, patient-individual therapy.

Introduction of the MR1T cell receptor expression construct into the T cell preparation may be achieved by lentiviral transduction, which the inventors have routinely used in their work on MR1T cells, or by standard methods of DNA expression vector (plasmid) or RNA transfection. The skilled person is aware of the relevant protocols and procedures.

Optionally, the transgene T cell preparation may be kept in culture for some time prior to being administered to the patient in order to expand their number and, again optionally, to further stimulate their differentiation into a particularly desired T cell subset.

In certain embodiments, the T cell preparation obtained from said patient is obtained from peripheral blood of the patient, particularly wherein said T cell preparation is obtained by selecting peripheral blood mononuclear cells (PBMC) for expression of one or several T cell markers selected from the group containing CD4, CD8, CD27, CD45RA and CD57.

In certain embodiments, the T cell preparation obtained from said patient is obtained from a tumour biopsy followed by subsequent expansion in-vitro. In certain embodiments, T cells are expanded in the presence of phytohemagglutinin, IL-2, IL-7 and IL-15. Proliferating T cells are isolated by magnetic sorting and used for T cell receptor engineering or for cloning and isolation of tumour-specific MR1-restricted T cells. The isolated MR1T cells are used for TCR gene cloning.

The plurality of MR1-specific T cell clones can be prepared in advance of the procedure and held in form of a library or panel for ad-hoc use whenever the need for rapid characterization of a tumour arises. This step is essentially an identification of the MR1-specific T cell receptor molecules that will recognize a particular tumour entity.

Alternatively, soluble MR1T TCRs may be generated and multimerized (see Subbramanian et al. *Nature Biotechnology*, 22, 1429, (2004)). TCR multimers will be labeled with fluorochromes and used to stain tumour cells isolated from tumour biopsies. Binding of soluble MR1T TCR multimers will indicate the capacity of that MR1T TCR to recognize tumour cells and thus will facilitate selection of the MR1T TCRs suitable for gene therapy in that patient.

Another aspect of the invention relates to an expression vector comprising, and leading to the transcription of, a nucleic acid sequence encoding a functional T cell receptor heterodimer, or a T cell receptor α chain capable of forming a functional T cell receptor heterodimer together with a T cell receptor β chain, and/or a T cell receptor β chain capable of forming a functional T cell receptor heterodimer together with a T cell receptor α chain. Of note, also MR1-specific γ-δ heterodimers have been found by the inventors, so the same applies to these chains.

In embodiments where the expression vector comprises a nucleic acid sequence encoding a T cell receptor α chain or a T cell receptor β chain (or a γ or δ chain), two different expression vectors (one encoding an α chain (γ chain) and one encoding a β chain (δ chain)) have to be introduced into a cell in order to enable expression of a functional T cell receptor heterodimer by said cell. The T cell receptor heterodimer specifically binds to an MR1 molecule, wherein said MR1 molecule is expressed on a tumour cell and presents a tumour-associated antigen.

The expression of the above mentioned nucleic acid sequences is controlled by a promoter sequence operable in a mammalian cell, particularly a human T-cell. In certain embodiments, the promoter is a constitutively activated promoter, for example the CMV immediate early promoter commonly used in molecular biology. In certain other embodiments, the promoter is an inducible promoter.

In certain embodiments of this aspect of the invention, the nucleic acid sequence comprised in the expression vector is or comprises a nucleic acid sequence that is selected from SEQ ID NO 007, SEQ ID NO 009 or SEQ ID NO 011, and/or encodes an amino acid sequence selected from SEQ ID NO 001, SEQ ID NO 003 or SEQ ID NO 005 (alpha chains).

In certain embodiments of this aspect of the invention, the nucleic acid sequence comprised in the expression vector is or comprises a nucleic acid sequence that is selected from SEQ ID NO 008, SEQ ID NO 010 or SEQ ID NO 012 and/or encodes an amino acid sequence selected from SEQ ID NO 002, SEQ ID NO 004 or SEQ ID NO 006 (beta chains).

Another aspect of the invention relates to a nucleic acid sequence encoding a functional T cell receptor heterodimer. The T cell receptor heterodimer specifically binds to a non-polymorphic MHC I-related (MR1) antigen-presenting molecule expressed on a tumour cell presenting a tumour-associated antigen.

In certain embodiments, the nucleic acid sequence encodes a T cell receptor α chain and is selected from SEQ ID NOs SEQ ID NO 007, SEQ ID NO 009 or SEQ ID NO 011, or encodes a T cell receptor α chain specified by an amino acid sequence selected from SEQ ID NO 001, SEQ ID NO 003 or SEQ NO ID 005.

In certain embodiments, the nucleic acid sequence encodes a T cell receptor β chain and is selected from SEQ ID NO 008, SEQ ID NO 010 or SEQ ID NO 012 or encodes a T cell receptor β chain specified by an amino acid sequence selected from SEQ ID NO 002, SEQ ID NO 004 or SEQ ID NO 006, or a sequence at least 85% (≥90%, 95%, 98) identical to an amino acid sequence selected from SEQ ID NOs 001 to 006 and having the same biological activity. In particular embodiments, each of the amino acid sequences comprises a CDR3 sequence selected from SEQ ID 65, 66, 67, 80, 81 and 82.

Another aspect of the invention relates to a T cell receptor protein that binds to a non-polymorphic MHC I-related MR1 antigen-presenting molecule. The MR1 molecule is expressed on a tumour cell and presents a tumour-associated antigen. In certain embodiments, the T cell receptor protein that binds to a non-polymorphic MHC I-related MR1 antigen-presenting molecule is identified by the method according to the first aspect of the invention.

In certain embodiments, the T cell receptor protein comprises a T cell receptor α chain characterized by an amino acid sequence selected from SEQ ID NO 001, SEQ ID NO 003 or SEQ NO ID 005 and a T cell receptor β chain characterized by an amino acid sequence selected from SEQ ID NO 002, SEQ ID NO 004 or SEQ ID NO 006.

Another aspect of the invention relates to a recombinant cell comprising the expression vector according to the invention, and/or the T cell receptor polypeptide according to the invention as specified in the preceding paragraphs. The skilled person is aware that in instances where the expression vector only comprises a nucleic acid sequence encoding a T cell receptor α chain (or a γ chain) or a T cell receptor β chain (or a δ chain), but not both, two different expression vectors (one encoding an α/γ chain and one encoding a β/δ chain) have to be introduced into the recombinant cell in order to enable expression of a functional T cell receptor heterodimer by said cell. In certain embodiments, the recombinant cell is a T cell derived from peripheral blood. In certain embodiments, the recombinant cell is derived from a tumour infiltrating lymphocyte.

Yet another aspect of the invention relates to the use of the recombinant cell according to the previously specified aspect of the invention for use in a method of therapy or prevention of cancer. The method comprises administration of the recombinant cell.

In certain embodiments, the cancer is characterized by MR1 expression.

In certain embodiments, the administration is effected by adoptive T cell immunotherapy.

The invention further relates to a method of treatment, or prevention of recurrence, of cancer, comprising administration of the recombinant cell according to the invention. In certain embodiments, the cancer is characterized by MR1 expression.

In certain embodiments, the administration is achieved by adoptive T cell immunotherapy.

The invention also relates to a collection of nucleic acid sequences, wherein each member of the collection encodes a different T cell receptor α chain, T cell receptor β chain, T cell receptor γ chain, T cell receptor δ chain or a T cell receptor α chain and β chain combination, or a T cell receptor γ chain and δ chain combination, wherein said combination is capable of specifically binding to an MR1 molecule presenting a cancer antigen. The nucleic acid sequences are capable to facilitate the expression of the T cell receptor α chain, β chain, or α and β chain combination in a mammalian cell.

Such collection will be used to select transgene constructs for transfer into T cells collected from a patient. After identification of the TCR sequences that are best to fit instigate reaction to a particular set of tumour antigens presented by the tumour in the first phase of the method of treatment, the physician will need to be able to select pre-produced expression vectors from such collection manufactured under GMP, to quickly effect the gene transfer into the patient's T cells.

In certain embodiments, the collection comprises a sequence selected from SEQ 007 to SEQ ID NO 012 and/or the collection comprises sequences encoding a T cell receptor molecule (or a T cell receptor constituting α or β chain) selected from SEQ ID NO 001 to SEQ ID NO 006.

Yet another aspect of the invention relates to a collection of recombinant T cells, wherein each member of the collection expresses as a transgene a T cell receptor capable of specifically binding to an MR1 molecule presenting a cancer antigen. In certain embodiments, the collection comprises a recombinant T cell comprising a T cell receptor protein heterodimer according to the respective aspect of the invention.

The inventors identified and isolated a novel population of human MR1-restricted T cells reactive to a variety of tumour cells in MR1-dependent manner. MR1T cell clones were commonly found in the blood of different healthy individuals, expressed diverse TCR genes and did not recognize previously identified microbial or folate-derived ligands of MR1. Instead, they recognized diverse sets of yet unknown antigens isolated from tumour cells and presented by MR1. The identification and characterization of the stimulatory antigens associated with tumour cells is currently ongoing. MR1T cell clones recognized and killed different types of tumour cells, thus displaying marked anti-tumour activity in vitro. In addition, they released different combinations of Th1, Th2 and Th17 cytokines, and displayed multiple chemokine receptor expression profiles, suggesting phenotypical and functional heterogeneity. Importantly, when paired TCR α and β genes or TCR γ and δ genes isolated from individual MR1T cell clones were transferred into TCR-deficient T cells, the recipient T cells acquired the capacity to recognize MR1-expressing tumour cells, thus indicating that the MR1T cell TCR gene transfer is sufficient for this type of tumour recognition and might be used to instruct select T cells to recognize MR1-expressing tumour cells.

Taken together, these findings reveal a novel functionally diverse population of tumour-reactive human T cells restricted to non-polymorphic MR1 molecules with diverse potential role in tumour immunity, thus providing new conceptual frameworks for cancer immune surveillance and immunotherapies.

In the present specification, the following abbreviations are used: APC, antigen-presenting cell; β2m, β2 microglobulin; DC, dendritic cell; GM-CSF, granulocyte-macrophage colony-stimulating factor; HPLC, high-pressure liquid chromatography; IFN-γ, interferon-γ; mAb, monoclonal antibody; MAIT cell, mucosal associated invariant T cell; MHC, major histocompatibility complex; MR1, MHC class I-related molecule; MR1T cell, MR1-restricted T cell; PBMC, peripheral blood mononuclear cell; TCR, T cell receptor; TIL, tumour-infiltrating lymphocyte.

The invention is further illustrated by the following examples and figures, from which further embodiments and advantages can be drawn. These examples are meant to illustrate the invention but not to limit its scope.

EXAMPLES

Methods

Cells. The following human cell lines were obtained from American Type Culture Collection: A375 (melanoma), THP-1 (myelomonocytic leukemia), J.RT3-T3.5 (TCRβ-deficient T cell leukemia), LS 174T (colon adenocarcinoma), HCT116 (colon carcinoma), Huh7 (hepatocellular carcinoma), HEK 293 (human embryonic kidney), and CCRF-SB (acute B cell lymphoblastic leukemia). SKW-3 cells (human T cell leukemia deficient in TCRα, β, γ and δ genes) were obtained from the Leibniz-Institute DSMZ-German Collection of Microorganisms and Cell Cultures. Two representative MAIT clones (MRC25 and SMC3) and one TCR γδ clone, (G2B9) (Gober et al., *The Journal of experimental medicine* 197, 163-168 (2003)) were used in this study as control cells and were generated from blood of two healthy donors and maintained in culture as previously described (Lepore et al., *Nat Commun* 5, 3866 (2014)). MR1T cells were isolated from the peripheral blood of healthy individuals after informed consent was obtained from donors at the time of blood collection under approval of the "Ethikkommision Nordwest and Zentralschweiz/EKNZ (139/13). Briefly, T cells purified by negative selection (EasySep™ Human T Cell Enrichment Kit, StemCell) were stimulated with irradiated (80 Gray) A375-MR1 cells (ratio 2:1) once a week for three weeks. Human rIL-2 (5 U/ml; Hoffmann-La Roche), rIL-7 and rIL-15 (both at 5 ng/ml, Peprotech) were added at day +2 and +5 after each stimulation. Twelve days after the last stimulation cells were washed and co-cultured overnight with A375-MR1 cells (ratio 2:1). $CD3^+CD69^+CD37^+$ cells were then sorted and cloned by limiting dilution in the presence of PHA (1 μg/ml, Wellcome Research Laboratories), human rIL-2 (100 U/ml, Hoffmann-La Roche) and irradiated PBMC ($5\times10^5$ cells/ml). In other experiments, MR1T cells clones were generated using the same protocol from sorted $CD3^+CD69^+CD137^+$ upon a single overnight stimulation with A375-MR1 cells (ratio 2:1). T cell clones were periodically re-stimulated following the same protocol (Lepore et al., ibid.). Monocytes and B cells were purified (>90% purity) from PBMCs of healthy donors using EasySep Human CD14 and CD19 positive selection kits (Stemcell Technologies) according to the manufacturer instructions. Mo-DCs were differentiated from purified $CD14^+$ monocytes by culture in the presence of GM-CSF and IL-4 as previously described (Lepore et al., ibid.). Human normal gut epithelial cells (GEC) were isolated from gut biopsies of tumour-free individuals according to a published protocol (Graves et al., *Journal of immunological methods* 414, 20-31 (2014)).

Generation of cells expressing MR1A gene covalently linked with β2m. A human MR1A cDNA construct linked to β2m via a flexible Gly-Ser linker was generated by PCR as previously described (Lepore et al., ibid.). The K43A substitution in the MR1A cDNA was introduced into the fusion construct using the following primers: MR1K43A_f 5'-CTCGGCAGGCCGAGCCACGGGC (SEQ ID NO 097) and MR1K43A_r 5'GCCCGTGGCTCGGCCTGCCGAG (SEQ ID NO 098). Resulting WT and mutant constructs were cloned into a bidirectional lentiviral vector (LV) (Lepore et al., ibid.). HEK 293 cells were transfected with individual LV-MR1A-β2m constructs together with the lentivirus packaging plasmids pMD2.G, pMDLg/pRRE and pRSV-REV (Addgene) using Metafectene Pro (Biontex) according to manufacturer instructions. A375, and THP-1, cells were transduced by spin-infection with virus particle containing supernatant in the presence of 8 μg/ml protamine sulfate. Surface expression of MR1 was assessed by flow cytometry and positive cells were FACS sorted.

Soluble recombinant β2m-MR1-Fc fusion protein. β2m-MR1-Fc fusion construct was obtained using human MR1A-β2m construct described above as template. DNA complementary to β2m-MR1A gene was amplified by PCR using primers: β2mXhoI_f 5'-CTCGAGATGTCTCGCTCCGTGGCCTTA (SEQ ID NO 099) and MR1-IgG1_r 5'-GTGTGAGTTTTGTCGCTAGCCTGGGGGACCTG (SEQ ID NO 100), thus excluding MR1 trans-membrane and intracellular domains. The DNA complementary to the hinge region and CH2-CH3 domains of human IgG1 heavy chain was generated using the following primers: NheI-hinge-f 5'-CAGGTCCCCCAGGCTAGCGACAAAACTCACAC (SEQ ID NO 101) and IgG1NotI_r 5'-GCGGCCGCTCATTTACCCGGAGACAGGGAGA (SEQ ID NO 102) from pFUSE-hIgG1-Fc1 (InvivoGen). The β2m-MR1A and IgG1 PCR products were joined together using two-step splicing with overlap extension PCR and the resulting construct subcloned into the XhoI/NotI sites of the BCMGSNeo expression vector. CHO-K1 cells were transfected with the final construct using Metafectene Pro (Biontex), cloned by limiting dilutions and screened by ELISA for the production of β2m-MR1-Fc fusion protein. Selected clones, adapted to EX-CELL ACF CHO serum-free medium (Sigma), were used for protein production and β2m-MR1-Fc was purified using Protein-A-Sepharose (Thermo Fisher Scientific) according to manufacturer instructions. Protein integrity and purity were verified by SDS-PAGE and Western Blot using anti-MR1 mAb 25.6 (Biolegend).

Flow cytometry and antibodies. Cell surface labeling was performed using standard protocols. Intracellular labeling was performed using the True-Nuclear™ Transcription Factor Buffer Set according to the manufacturers' instructions. The following anti-human mAbs were obtained from Biolegend: CD4-APC (OKT4), CD8α-PE (TuGh4), CD161-Alexa Fluor 647 (HP-3G10), CD69-PE (FN50), CD3-PE/Cy7, Brilliant Violet-711, or Alexa-700 (UCHT1), CD137-biotin (n4b4-1), CXCR3-Brilliant Violet 421 (G025H7), CD83-biotin (HB15e), MR1-PE (26.5) and TRAV1-2-PE (10C3). CD86-FITC (2331), CCR4-PECy7 (1G1) and CCR6-PE (11A9) mAbs were from BD Pharmingen. All these mAbs were used at 5 μg/ml. Biotinylated mAbs were revealed with streptavidin-PE, -Alexa Fluor 488, or -Brilliant violet 421 (2 μg/ml, Biolegend). Samples were acquired on LSR Fortessa flow cytometer (Becton Dickinson). Cell sorting experiments were performed using an Influx instrument (Becton Dickinson). Dead cells and doublets were excluded on the basis of forward scatter area and width, side scatter, and DAPI staining. All data were analyzed using FlowJo software (TreeStar).

TCR gene analysis of MR1T cell clones. TCRα and β or gene TCRγ and δ expression by MR1T cell clones was assessed either by RT-PCR using total cDNA and specific primers, or by flow cytometry using the IOTest® Beta Mark TCR Vβ Repertoire Kit (Beckman Coulter) according to the manufacturers' instructions or panγδ TCR-specific monoclonal antibodies (B1, Biolegend). For RT-PCR, RNA was prepared using the NucleoSpin RNA II Kit (Macherey Nagel) and cDNA was synthesized using Superscript III reverse transcriptase (Invitrogen). TCRα, β, γ and δ cDNAs were amplified using sets of Vα, Vβ, Vγ and Vδ primers as directed by the manufacturer (TCR typing amplimer kit, Clontech). Functional transcripts were identified by sequencing and then analyzed using the ImMunoGeneTics information system (http://www.imgt.org).

TCR gene transfer. TCRα and β functional cDNA from the MAIT cell clone MRC25 were cloned into the XhoI/NotI sites of the BCMGSNeo expression vector (Karasuyama and Melchers Eur. J. Immunol. 1988 18:97-104) and the resulting constructs were used to co-transfect J.RT3-13.5 cells by electroporation according to standard procedure. Transfectants expressing TRAV1-2 and CD3 were FACS sorted. The TCRα and β or TCRγ and δ functional cDNAs from MR1T clones were cloned into the XmaI/BamHI sites of a modified version of the plasmid 52962 (Addgene) expression vector. SKW-3 cells were transduced with virus particle-containing supernatant generated as described above. Cells were FACS sorted based on CD3 expression.

Fractionation of cell and whole tumour lysates. Total cell lysates were generated from a single pellet of $2.5 \times 10^9$ THP-1 cells via disruption in water with mild sonication. The sonicated material was then centrifuged (15,000 g for 15 min at 4° C.) and the supernatant collected (S1). Next, the pellet was re-suspended in methanol, sonicated, centrifuged as before, and the supernatant obtained was pooled with the S1 supernatant. The final concentration of methanol was 10%. The total cell extract was then loaded onto a C18 Sep-Pak cartridge (Waters Corporation) and the unbound material was collected and dried (fraction E-FT). Bound material was eluted in batch with 75% (fraction E1) and 100% methanol (fraction E2). The E-FT material was re-suspended in acetonitrile/water (9:1 vol/vol) and loaded onto a $NH_2$ Sep-Pak cartridge (Waters Corporation). Unbound material (fraction N-FT) and 4 additional fractions were eluted with increasing quantities of water. Fraction N1 was eluted with 35% $H_2O$, fraction N2 with 60% $H_2O$, fraction N3 with 100% $H_2O$, and fraction N4 with 100% $H_2O$ and 50 mM ammonium acetate (pH 7.0). All fractions were dried and then re-suspended in 20% methanol (fractions E1, E2 and N-FT) or 100% $H_2O$ (all other fractions) prior to being stored at −70° C.

Mouse EMT6 breast tumours were prepared as described (Zippelius et al., Cancer Immunol Res 3, 236-244 (2015)). Freshly excised tumours were extensively washed in saline, weighted and 4 g masses were homogenized in 7 ml of HPLC-grade water using a Dounce tissue grinder. Tumour homogenate underwent two freeze-thaw cycles, centrifuged (3,250 g) for 10 min at 4° C., and supernatant was collected and stored at −70° C. The pellet was extracted a second time with 2 ml of HPLC-grade water, centrifuged (5,100 g) for 10 min at 4° C. and the supernatant was collected and stored at −70° C. The pellet was further extracted with 9 ml of HPLC-grade methanol for 5 min at room temperature by vortexing, centrifuged (5,100 g) for 10 min at 4° C., and supernatant collected. The three supernatants were pooled, dried, and resuspended in water:methanol (10:1). Material was fractionated using C18 and $NH_2$ Sep-Pak cartridges as above.

T cell activation assays. MR1-restricted T cells ($5 \times 10^4$/well unless otherwise indicated) were co-cultured with indicated target cells ($5 \times 10^4$/well) in 200 μl total volume in duplicates or triplicates. T cells were cultured with indicated APCs for 24 h. In some experiments, anti-MR1 mAbs (clone 26.5) or mouse IgG2a isotype control mAbs (both at 30 μg/ml) were added and incubated for 30 min prior to the addition of T cells. E. coli lysate was prepared from the DH5a strain (Invitrogen) grown in LB medium and collected during exponential growth. Bacterial cells were washed twice in PBS and then lysed by sonication. After centrifugation (15,000 g for 15 min), the supernatant was collected, dried, and stored at −70° C. APCs were pulsed for 4 h with E. coli lysate equivalent to $10^8$ CFU/ml (unless otherwise indicated) before addition of T cells. In some experiments, APCs were pre-incubated with 6-FP or Ac-6-FP (Schircks Laboratories) for 4 h before co-culture with T cells. In control experiments with TCR γδ cells expressing TCR Vγ9 and Vδ2 chains, the APCs were first treated for 6 h with zoledronate (10 μg/ml) prior to T cell addition. Activation experiments with plate-bound recombinant human β2m-MR1-Fc were performed by coating β2m-MR1-Fc onto 96 well plates (4 μg/ml) and loading with cartridge-purified cell lysates for 4 h at 37° C. before washing twice and adding T cells. Supernatants were collected after 24 h and IFN-γ or GM-CSF were assessed by ELISA. Multiple cytokines and chemokines in cell culture supernatants were analyzed using the Milliplex MAP human cytokine/chemokine magnetic bead panel—Premixed 41 plex (HCYTMAG-60K-PX41; Merck Millipore) according to the manufacturer's instructions. Samples were acquired on a Flexmap 3D system (Merck Millipore) and Milliplex analyst software was used to determine mean fluorescence intensity and analyte concentration.

Killing of tumour cells. Killing assays were performed using target cell lines ($2 \times 10^4$ cells/ml) incubated either alone or with T cells at different E/T ratios for 24 h, in the presence or absence of anti-MR1 mAb (30 μg/ml, clone 26.5). The target cells were stained with PE-Annexin V (BD) and propidium iodide (PI) (Sigma-Aldrich), as previously described (2). T cells were identified by staining with anti-CD3 mAbs and excluded from the analysis. Apoptosis was evaluated as follows: Annexin $V^+PI^+$=advanced apoptosis and Annexin $V^-PI^+$=necrosis. The percentage of apoptotic+necrotic cells in the absence of T cells (spontaneous apoptosis; no T cells) is also shown.

Statistics. Data were analyzed using Unpaired Student's t-test (Prism 6, GraphPad software).

Identification and Characterization of Novel Tumour-Reactive MR1-Restricted T Cells in Healthy Donors The inventors detected an atypical MR1-restricted T cell clone that did not react to microbial ligands during earlier studies on the repertoire of human MAIT cells. This T cell clone (DGB129) recognized cell lines constitutively displaying surface MR1 (CCRF-SB lymphoblastic leukemia cells, or THP-1 monocytic leukemia cells; FIG. 1A) or transfected with the MR1 gene (A375 melanoma cells; A375-MR1; FIG. 1A) in the absence of any exogenously added antigens (FIG. 1B). Sterile recognition of MR1$^+$ target cells was fully inhibited by blocking with anti-MR1 monoclonal antibodies (mAbs) (FIG. 1B), and thus resembled the MAIT cell response to *E. coli*-derived antigens assessed in parallel (FIG. 1C). Importantly, DGB129 T cells also failed to recognize the synthetic MAIT cell agonist 6,7-dimethyl-8-D-ribityllumazine (RL-6,7-diMe; FIG. 1D), differently from a control MAIT cell clone, which instead was stimulated in MR1-dependent manner by this compound (FIG. 1E). DGB129 cells did not express the canonical semi-invariant TCR typical of MAIT cells (Table 1).

Figures 2A, 2B, 2C, 2D, 2E:
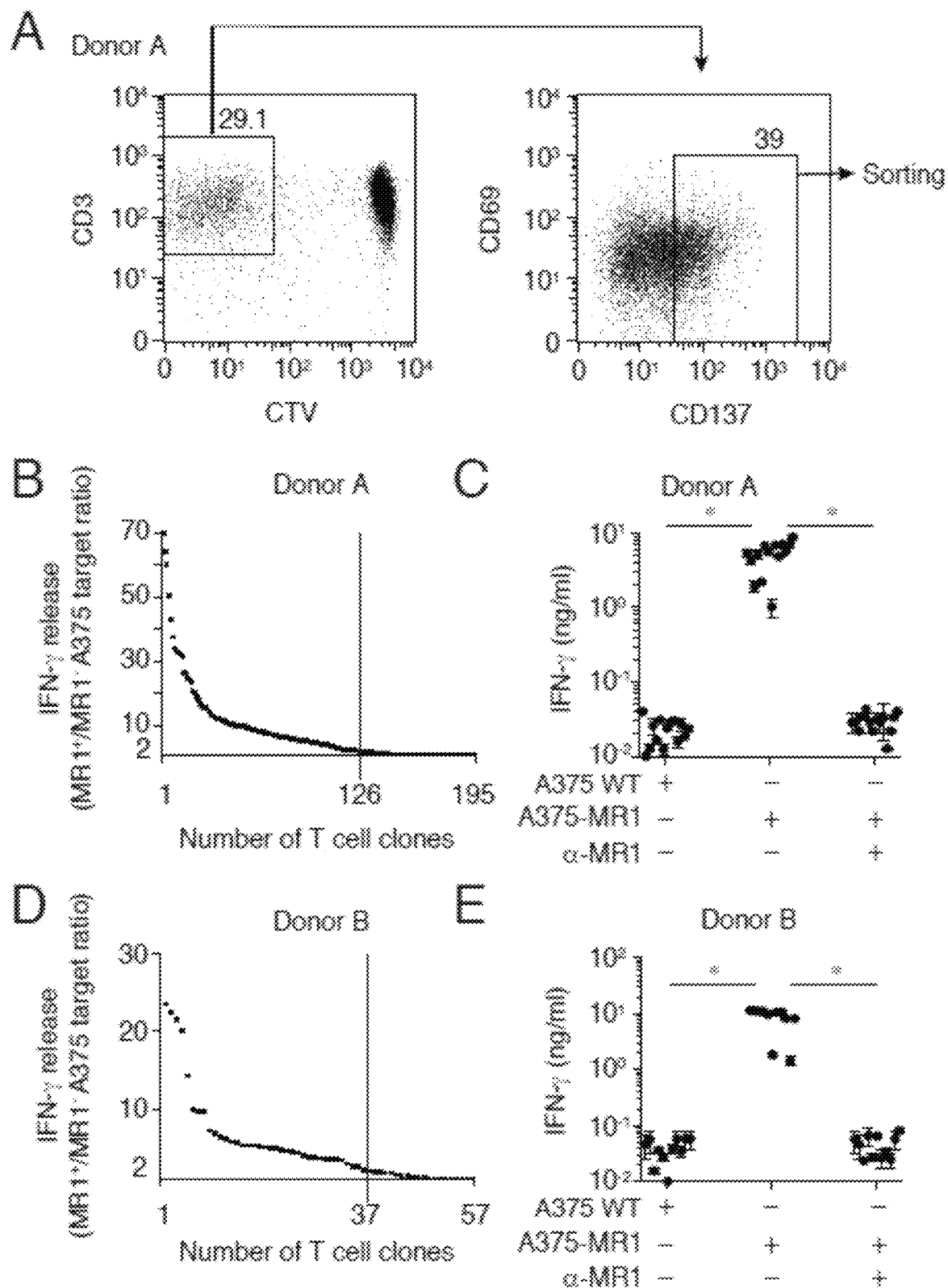
FIGS. 2A-2E. Isolation strategy of MR1T cell clones from peripheral T cells. (A) FACS analysis of purified T cells previously expanded with irradiated A375-MR1 cells following overnight co-culture with A375-MR1 cells in the absence of exogenous antigens. Left dot plot shows CD3 and CellTrace violet (CTV) staining in live cells. Right dot plot shows CD69 and CD137 expression of CD3-positive CTV-negative gated cells. Arrows indicate gating hierarchy. Numbers indicate the percentages of cells within the gates. Cells from Donor A are illustrated as a representative donor. (B, D) Cumulative results of T cell clones screening from Donors A and B. T cell clones were generated from CD3$^+$CTV$^-$CD137$^+$ sorted T cells as depicted in A. Graphs show the individual clones (x axis) and their IFN-γ release (y axis), expressed as ratio between the amount of cytokine secreted in response to A375-MR1 cells vs. A375 WT cells. Each dot represents a single T cell clone, tested at the same time in the indicated experimental conditions. The vertical lines indicate the number of T cell clones displaying MR1-restricted reactivity (i.e. the clones showing an IFN-γ release ratio above the arbitrary cut-off of 2). Results are representative of two independent experiments. (C, E) IFN-γ release by 14 representative clones from Donor A and 11 clones from Donor B after stimulation with A375 WT, A375-MR1 and A375-MR1 in the presence of blocking anti-MR1 mAbs (α-MR1). Dots represent the IFN-γ release (mean±SD of duplicate cultures) by each clone. Results are representative of three independent experiments. * P<0.05 (Unpaired Student's t-test).

The inventors asked whether the DGB129 clone was representative of a novel population of tumour-reactive MR1-restricted T cells different from microbe-reactive MAIT cells. They therefore established a method to isolate and study these unpredicted MR1-restricted T cells. Purified T cells from two healthy donors were labelled with the proliferation marker CellTrace violet (CTV) and stimulated with irradiated A375-MR1 cells in the absence of exogenous antigens. Proliferating cells were re-challenged with A375-MR1 cells and those expressing high levels of the activation marker CD137 were sorted and cloned by limiting dilution (FIG. 2A). Individual T cell clones were then interrogated for their capacity to recognize A375-MR1 and A375 cells lacking MR1 (A375-WT). In both donors the inventors found that a major fraction of T cell clones (126/195 and 37/57, respectively) displayed specific recognition of A375-MR1 cells (FIG. 2B,D), which was inhibited by anti-MR1 blocking mAbs (FIG. 2C,E). Staining with TCR Vβ-specific mAbs of 12 MR1-reactive T cell clones revealed that they expressed 7 different TRBV chains (TRBV4-3, 6-5/6-6/6-9, 9, 18, 25-1, 28, 29-1) with some of the clones sharing the same TRBV gene. Furthermore, none expressed the TRAV1-2 chain, canonical for MAIT cells.

Figures 3A, 3B, 3C, 3D:
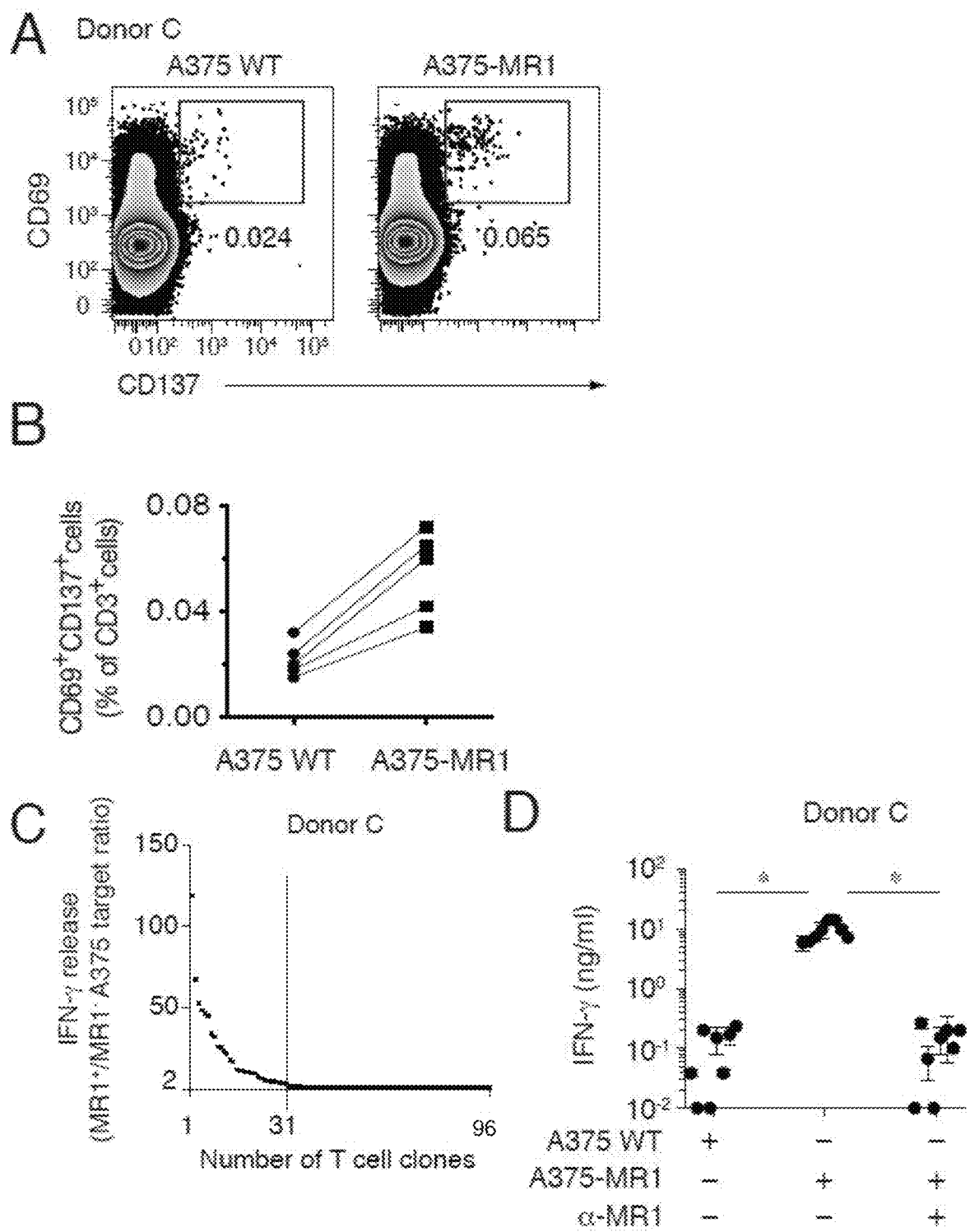
FIGS. 3A-3D. MR1T cells are common in the blood of healthy individuals. (A) Flow cytometry analysis of purified T cells from a representative donor (Donor C) after overnight co-culture with A375 WT or A375-MR1 cells. Dot plots show CD69 and CD137 expression on live CD3$^+$ cells. Numbers indicate the percentage of cells in the gates. (B) Frequency of CD69$^+$CD137$^+$ T cells from 5 different donors after overnight co-culture with A375 WT or A375-MR1 cells. (C) Cumulative results of T cell clone stimulation assays from Donor C. T cell clones were generated from CD3$^+$CD69$^+$CD137$^+$ sorted T cells as depicted in A, right dot plot. The graph shows the number of tested clones (x axis) and IFN-γ release (y axis) expressed as ratio between the amounts of cytokine secreted in response to A375-MR1 cells vs. A375 WT cells. Each dot represents a single T cell clone, tested at the same time in the indicated experimental conditions. The vertical line indicates the number of T cell clones displaying MR1-restricted reactivity (i.e. the clones showing an IFN-γ release ratio above arbitrary cut-off of 2). Results are representative of two independent experiments. (D) Recognition of A375-MR1 but not A375 WT cells in the absence of exogenous antigens by 8 representative MR1-restricted T cell clones from Donor C. Inhibition of T cell clone reactivity to A375-MR1 cells by blocking anti-MR1 mAbs (α-MR1). Dots represent the IFN-γ release (mean±SD of duplicate cultures) by each clone tested in the three experimental conditions. Results are representative of three independent experiments. * P<0.05 (Unpaired Student's t-test).

Lack of specific markers did not allow univocal identification of these novel T cells ex vivo by standard flow cytometry. Therefore, their frequency was estimated by combining flow cytometry analysis after very short-time in vitro stimulation and single T cell cloning experiments. Purified blood T cells from five healthy donors were co-cultured overnight with MR1-deficient or MR1-sufficient A375 cells and analysed for the expression of the activation markers CD69 and CD137 (FIG. 3A). In all of the five donors screened, the percentage of CD69$^+$CD137$^+$ T cells detected was consistently higher after stimulation with A375-MR1 cells (range 0.034-0.072% of T cells) than after co-culture with A375-WT cells (range 0.015-0.032%) (FIG. 3A,B). As the two types of APCs differed for MR1 expression, MR1-reactive T cells accounted for the increased numbers of activated T cells after stimulation with MR1-positive APCs. Using this approach, the inventors estimated that the circulating T cell pool of the analysed individuals contained A375-MR1-reactive T cells at frequency ranging between 1:2,500 (0.072-0.032=0.04%) and 1:5,000 (0.034-0.015=0.019%). This estimated frequency is higher than the frequency of peptide-specific CD4$^+$ T cells after antigen exposure (Lucas et al., J Virol 78:7284-7287; Su et al., Immunity 38:373-383). These observations were supported by parallel experiments in which sorted CD69$^+$CD137$^+$ overnight-activated T cells from one of these donors (Donor C, FIG. 3A, right panel) were cloned. Indeed, 31 out of 96 screened T cell clones (32%) displayed specific reactivity to A375-MR1 cells (FIG. 3C), which was inhibited by anti-MR1 mAbs (FIG. 3D). Accordingly, the calculated frequency of A375-MR1-responsive T cells among blood T cells of this donor was 1:5,000 (0.065×0.32=0.02%), a value consistent with the estimated range. Detailed analysis of representative T cell clones derived from three donors confirmed that they displayed diverse TCRα and β chains and indicated differential expression of CD4, CD8 and CD161 (Table 1).

Collectively, these findings suggested that the identified tumour-reactive MR1-restricted T cells are a novel yet common polyclonal population of lymphocytes in the blood of healthy human individuals (hereafter termed MR1T cells).

MR1T Cell TCR Gene Transfer Confers MR1-Restricted Recognition of Tumour Cells

Figures 4A, 4B, 4C, 4D, 4E:
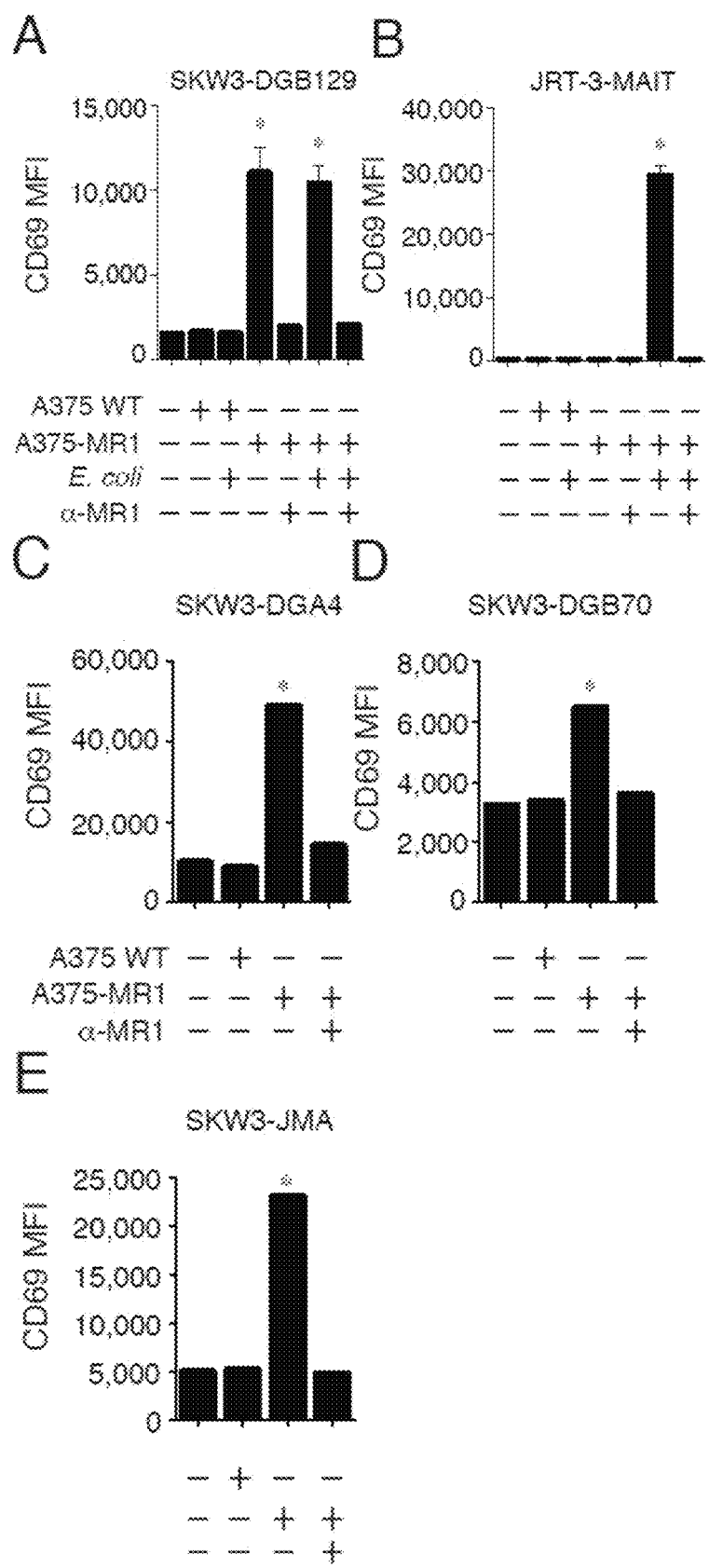
FIGS. 4A-4E. MR1T TCR gene transfer confers MR1-restricted recognition of A375 cells. Stimulation of (A) SKW-3 cells expressing the DGB129 TCR (SKW3-DGB129) and (B) J.RT3-T3.5 cells expressing the MAIT MRC25 TCR (J.RT3-MAIT) with A375 cells that expressed (A375-MR1) or lacked (A375 WT) MR1, with or without E. coli lysate and anti-MR1 mAbs. Stimulation of SKW-3 cells expressing the TCRs of three individual MR1T cell clones (C) DGA4 (SKW3-DGA4), (D) DGB70 (SKW3-DGB70) and (E) JMA (SKW3-JMA) with A375-MR1 or A375 WT cells in the presence or not of or anti-MR1 mAbs. CD69 median fluorescence intensity (MFI)+SD of duplicate cultures of transduced T cells are shown. The CD69 MFI of transduced T cells cultured in the absence of APCs is also shown. Mock-transduced T cells showed background levels of CD69 expression when incubated with A375-MR1 or A375 WT (not shown). Data are representative of three independent experiments. * P<0.05 (Unpaired Student's t-test).

The inventors next investigated whether MR1T cell reactivity to tumour cells was mediated by the TCR. Expression of paired TCRα and β genes cloned from different MR1T cell clones in the TCR-deficient SKW-3 cells, conferred MR1 recognition of tumour cells which was comparable to that displayed by the original MR1T cells and which was completely blocked by anti-MR1-mAbs (FIG. 4A-C). In control experiments, transfer of TCRα and β genes of a representative MAIT cell clone conferred the ability to recognize A375-MR1 cells in MR1-dependent manner only in the presence of *E. coli* antigens (FIG. 4D). These data highlighted the critical role of the TCR in mediating MR1T cell recognition of tumour cells and suggested that MR1T cell TCR gene transfer can effectively redirect the reactivity of selected T cells toward MR1-expressing tumour cells.

Differential Recognition of Tumour Cells by MR1T Cell Clones

Figure 5A:
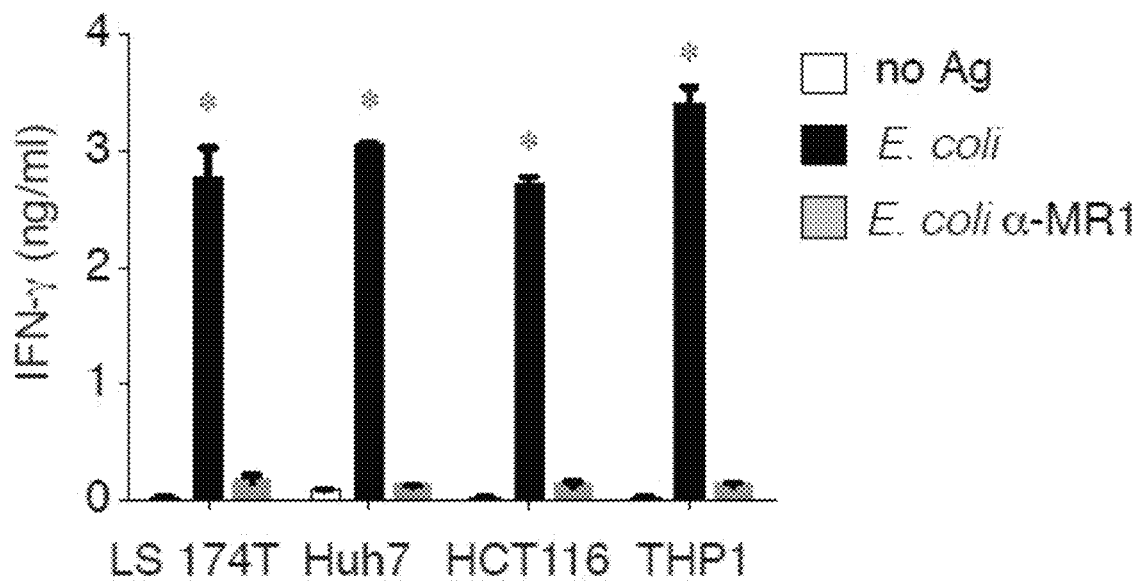
FIGS. 5A-5B. Differential recognition of various types of tumour cells by MR1T cell clones. (A) Recognition of four human cells lines expressing constitutive surface levels of MR1 by the representative SMC3 MAIT cell clone in the absence (no Ag) or presence of E. coli lysate (E. coli) with or without anti-MR1 blocking mAbs (α-MR1). (B) Recognition of the same cell types as in A by thirteen MR1T cell clones with or without anti-MR1 mAbs (α-MR1). Graphs show IFN-γ release (mean±SD of duplicate cultures).
Figure 5B:
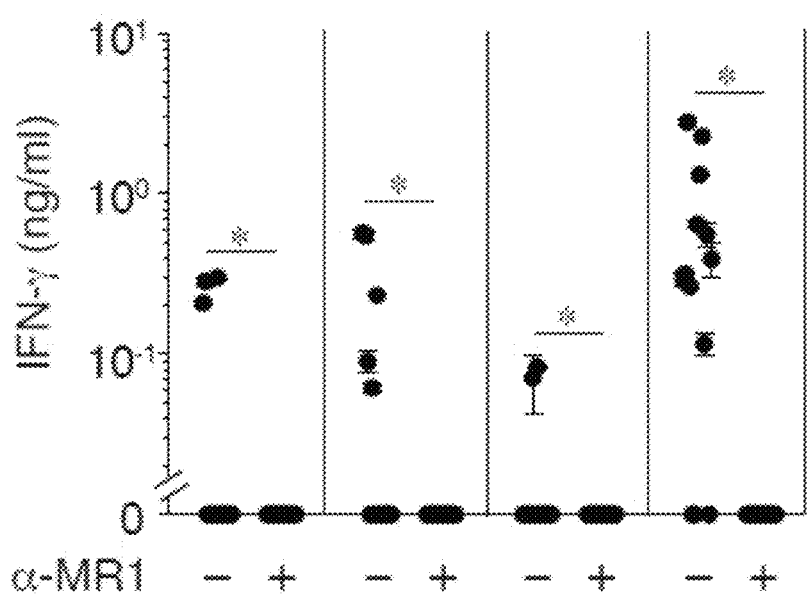

Having generated a large panel of MR1T cell clones reacting to MR1-expressing A375 melanoma cells, the inventors next investigated whether they could also recognize other types of tumour cells constitutively expressing surface MR1, including THP-1 myelomonocytic cells, Huh7 hepatoma cells, HCT116 colon carcinoma cells and LS 174T goblet-like colon adenocarcinoma cells. All these cell types supported MAIT cell activation in the presence of microbial antigens and in an MR1-dependent manner (FIG. 5A). The same cells were able to induce sterile activation of select MR1T cell clones to various extents. THP-1 cells were recognized by the majority of the tested MR1T cell clones, followed by the Huh7 hepatoma cells, the LS 174T goblet-like cells and the HCT116 colon carcinoma cells (FIG. 5B). Importantly, all responses were blocked by anti-MR1 mAbs.

These data further confirmed that MR1T cells are a novel and heterogeneous population of tumour-reactive T cells restricted to the non-polymorphic antigen-presenting molecule MR1.

MR1T Cells Recognize MR1-Bound Antigens Present in Tumour Cells

Figures 6A, 6B, 6C:
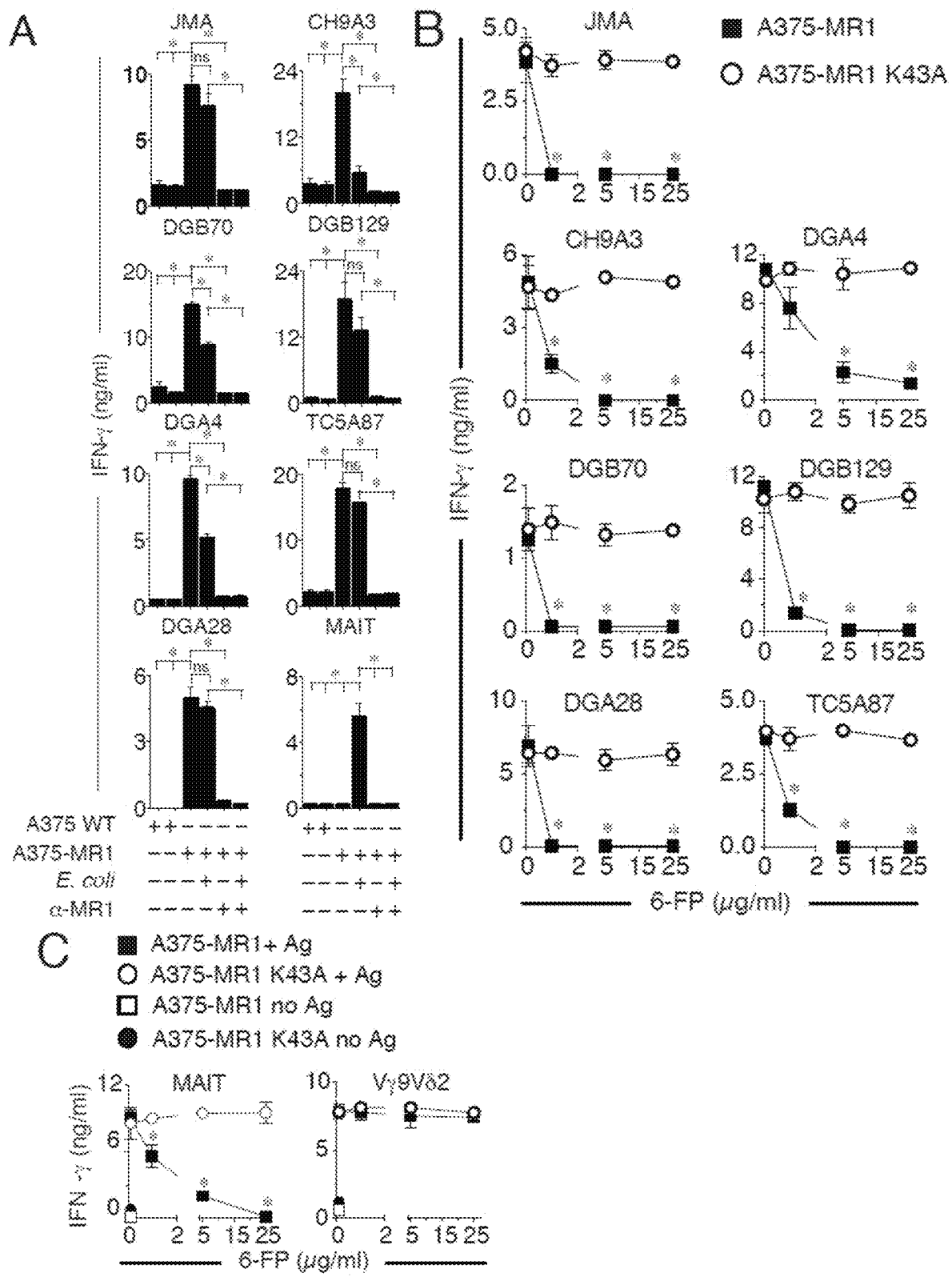
FIGS. 6A-6C. MR1T cell clones do not react to microbial ligands or to 6-FP. (A) Response of seven MR1T cell clones and one control MAIT cell clone co-cultured with A375 cells expressing (A375-MR1) or not (A375 WT) MR1 in the presence or absence of E. coli lysate. Blocking of T cell clone reactivity by anti-MR1 mAbs (α-MR1) is also shown. (B) Response of MR1T cell clones to A375 cells expressing either WT MR1 molecules (A375-MR1) or K43A-mutated MR1 molecules (A375-MR1 K43A) in the presence of 6-formyl pterin (6-FP). (C) Stimulation of control MAIT cell clone MRC25 or control TCR Vγ9Vδ2 clone G2B9 with A375-MR1 or A375-MR1 K43A cells previously incubated with or without E. coli lysate or zoledronate, respectively, either in the absence or presence of 6-FP. Results are expressed as mean±SD of IFN-γ measured in duplicate cultures. Results are representative of three independent experiments. * P<0.05 (Unpaired Student's t-test).
Figure 7A:
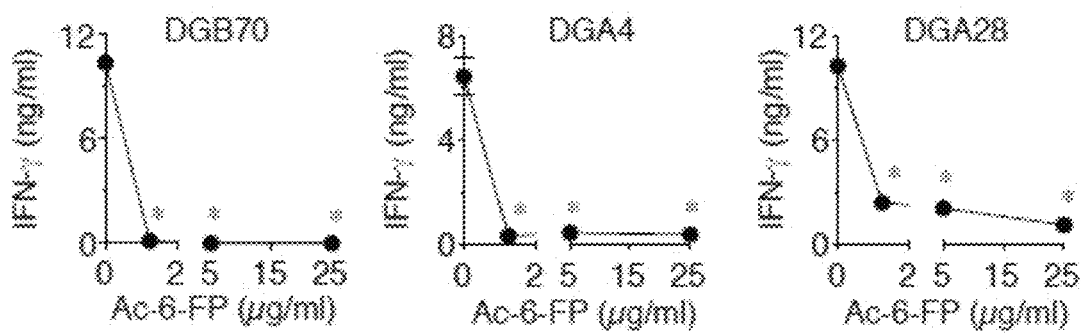
FIGS. 7A-7E. MR1T cell clones do not recognize Ac-6-FP. (A) Stimulation of three representative MR1T cell clones by A375-MR1 cells in the absence or presence of acetyl-6-formyl pterin (Ac-6-FP). (B) Stimulation of two MAIT cell clones (MRC25 and SMC3) by A375-MR1 cells pulsed with E. coli lysate in the absence or presence of Ac-6-FP. (C) A375-MR1 cells were treated with zoledronate (Zol) in the absence or presence of Ac-6-FP (25 µg/ml) and used to stimulate a TCR Vγ9-Vδ2 cell clone (G2B9). (D) A375 cells expressing K43A mutant MR1 molecules (A375-MR1 K43A) were used to stimulate the three MR1T cell clones shown in A, in the absence or presence of Ac-6-FP (25 μg/ml). (E) Stimulation of the two MAIT cell clones used in B by A375-MR1 K43A cells pulsed with E. coli lysate in the absence or presence of Ac-6-FP (25 μg/ml). Results are expressed as mean±SD of IFN-γ release assessed in duplicate cultures and are representative of three independent experiments. * P<0.05 (Unpaired Student's t-test).
Figure 7B:
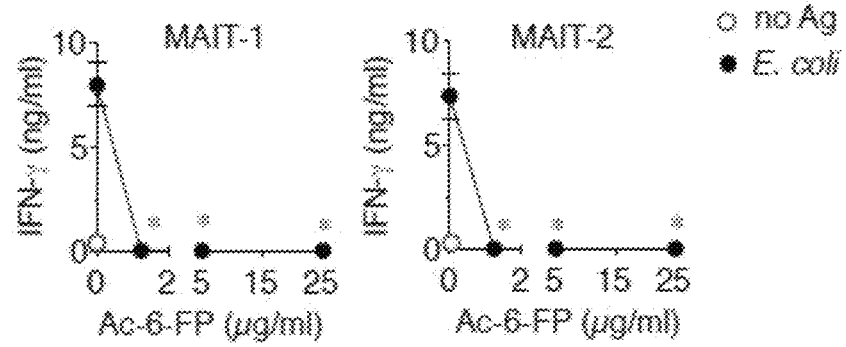
Figure 7C:
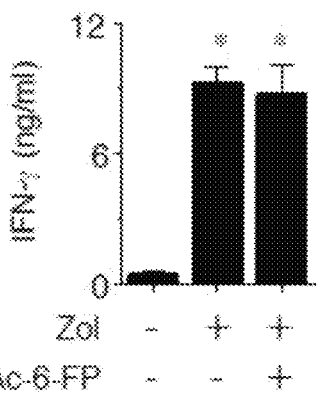
Figure 7D:
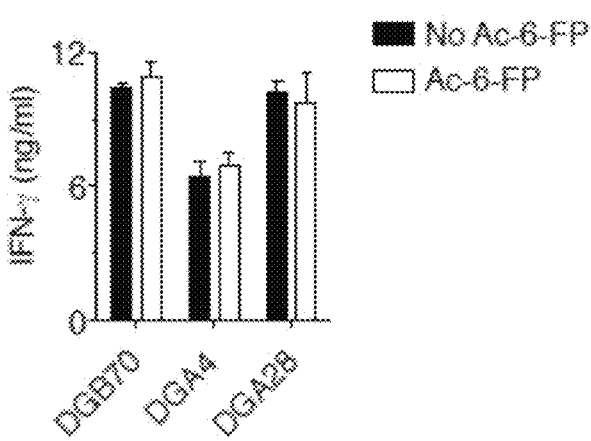
Figure 7E:
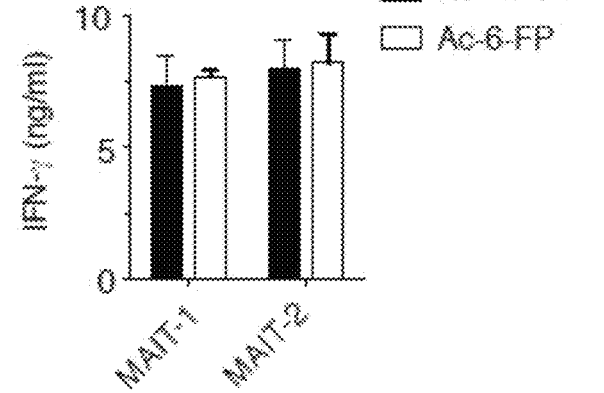

The inventors next studied the basis of MR1T cell reactivity to tumour cells. First, they sought to definitively rule out the possibility that MR1T cell clones could recognize microbial antigens, in analogy to MAIT cells. While a control MAIT cell clone reacted to A375-MR1 cells only in the presence of E. coli lysate, activation of different MR1T cell clones was not enhanced by the E. coli lysate (FIG. 6A). Consistent with these data, MR1-negative A375-WT cells failed to stimulate either type of T cells, irrespective of whether E. coli lysate was added, (FIG. 6A) and importantly anti-MR1 mAbs efficiently blocked both MR1T and MAIT cell responses (FIG. 6A). These findings confirmed that microbial ligands present in E. coli and stimulating MAIT cells do not stimulate the tested MR1T cells.

The inventors then tested the response of MR1T cells to the known MR1 ligands 6-FP and Ac-6-FP, which have previously been reported to stimulate a rare subset of TRAV1-2-negative T cells and inhibit MAIT cell activation by microbial antigens. MR1T cell stimulation was impaired in the presence of 6-FP or Ac-6-FP ligands, which also impaired E. coli stimulation of control MAIT cells, but did not disrupt control TCR γδ cell responses to cognate antigen presented by the same APCs, thus excluding compound toxicity (FIGS. 6B,C and 7A-C). Notably, 6-FP or Ac-6-FP failed to inhibit the activation of MR1T cells or MAIT cells when the target A375 cells were transduced to express mutant MR1 molecules with defective ligand binding capacity (blockade of Schiff base formation with ligands by mutation of Lysine 43 into Alanine, A375-MR1 K34A; FIGS. 6B,C and 7D,E). The specific inhibition observed with 6-FP or Ac-6-FP indicated that MR1T cells i) do not recognize 6-FP and Ac-6-FP, ii) react to MR1-bound cellular antigens, and iii) are stimulated by ligands that do not require the formation of a Schiff base with MR1.

Figures 8A, 8B, 8C, 8D, 8E, 8F:
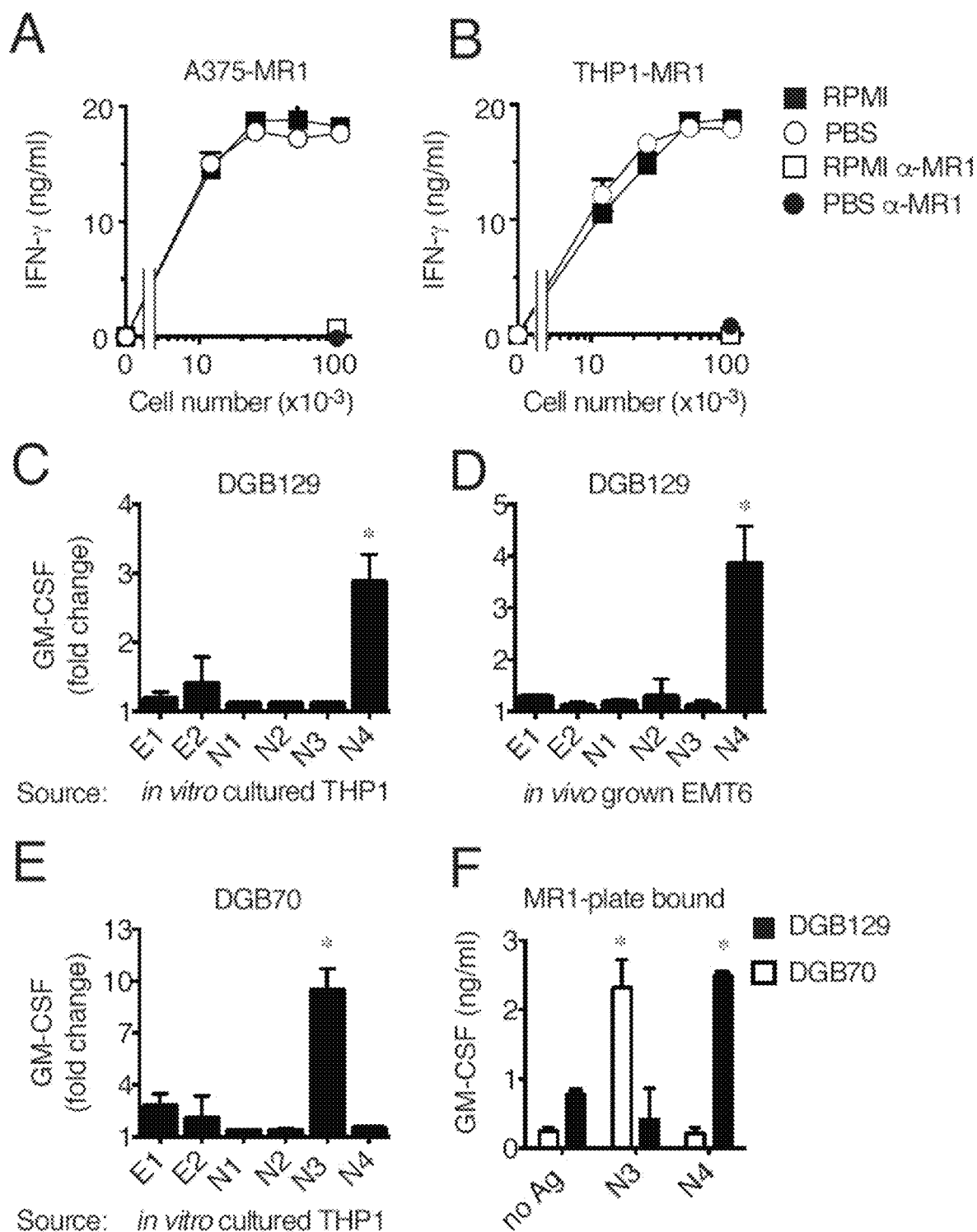
FIGS. 8A-8F. MR1T cells recognize antigens present in tumour cells and not derived from RPMI 1640 medium. Stimulation of the DGB129 MR1T cell clone by MR1-overexpressing (A) A375 cells (A375-MR1) and (B) THP-1 cells (THP1-MR1) grown for 4 days in RPMI 1640 or in PBS both supplemented with 5% human serum. Inhibition of T cell clone reactivity by anti-MR1 blocking mAbs (α-MR1) is shown. DGB129 cells recognize APCs loaded with fractions isolated from (C) THP-1 cell lysate or from (D) in vivo grown mouse breast tumour EMT6. Fractions E1 and E2 contain hydrophobic molecules; fractions N1-N4 contain hydrophilic molecules. (E) DGB70 MR1T cells react to N3 fraction of THP-1 lysate. (F) Stimulation of DGB129 and DGB70 T cells by THP-1-derived fractions N3 and N4 loaded onto plastic-bound recombinant MR1. Shown is T cell release of IFN-γ or GM-CSF mean±SD of duplicate cultures (representative of three independent experiments). Total cytokine release is shown in panels A, B, F; fold increase over background is shown in panels C, D, E. * P<0.05 (Unpaired Student's t-test).

To gain further information on the origin of the recognized antigens the inventors asked whether the stimulatory capacity of tumour target cells was dependent on culture medium constituents, as some MR1 ligands, e.g. 6-FP, may derive from folate present in RPMI 1640 medium used for cell culture. Both THP-1 and A375-MR1 cells were extensively washed and cultivated 4 days in phosphate buffered saline solution (PBS) supplemented exclusively with 5% human serum. Cells were washed daily before being used to stimulate DGB129 MR1T cells and the T cell activation assays were performed in PBS. THP-1 and A375-MR1 cells grown in RPMI 1640 or in PBS showed the same stimulatory capacity (FIG. 8A,B), thus indicating that medium constituents are not responsible for MR1T cell activation. To directly investigate whether the stimulatory antigens were present in target tumour cells, the inventors then performed T cell activation assays using as source of antigen two types of tumour lysates. The first lysate was obtained from in vitro cultured THP-1 cells, while the second one was prepared from mouse breast tumours immediately after resection. Two hydrophobic and four hydrophilic fractions were obtained and tested using as APCs THP-1 cells that constitutively express low levels of MR1. The DGB129 clone reacted only to fraction N4, containing highly hydrophilic compounds isolated from both freshly explanted mouse tumour and in vitro cultured THP-1 cells (FIG. 8C,D). These results ruled out the possibility that stimulatory antigens were derived from RPMI 1640 components and indicated their cellular origin. The inventors also tested the fractions generated from THP-1 lysates with DGB70, another representative MR1T cell clone. DGB70 cells recognized fraction N3 and not N4, (FIG. 8E), suggesting that at least two distinct compounds differentially stimulated the two MR1T clones. The same fractions were also loaded onto plastic-bound MR1 molecules and showed alternative and specific stimulatory capacity, i.e. N3 stimulated only DGB70 cells, while N4 stimulated only DGB129 cells (FIG. 8F). In the absence of N3 and N4 fractions, the two clones did not react to MR1, further indicating the requirement of specific antigens.

In conclusion, these data indicated that MR1T cells recognize MR1 complexed with ligands not derived from culture medium and present also in tumour cells grown in vivo.

MR1T Cells Display Differential Anti-Tumour Responses

Figures 9A, 9B, 9C, 9D, 9E, 9F:
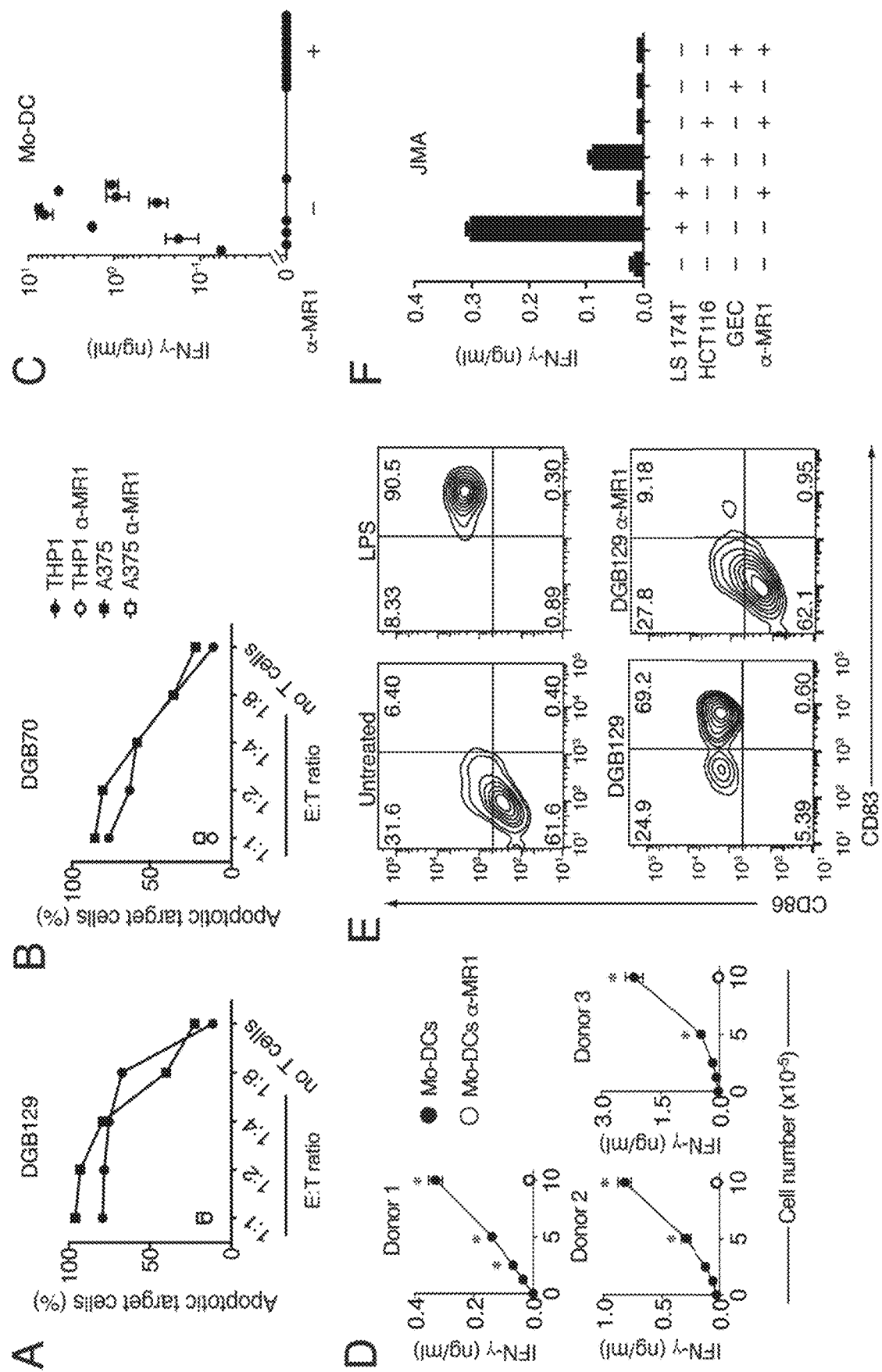
FIGS. 9A-9F. MR1T cells display differential anti-tumour responses. The MR1-expressing tumour cell lines THP-1 and A375 were cultured overnight with the MR1T cell clones (A) DGB129 or (B) DGB70 at the indicated effector:target (E:T) ratios. The graphs show the percentages of apoptotic target cells in individual experimental conditions, assessed by flow cytometry using Annexin V and propidium iodide staining. MR1T cells were identified by staining with anti-CD3 mAbs and excluded from the analysis. Inhibition of MR1T cell clone killing capacity by anti-MR1 (α-MR1) mAbs is also shown at the 1:1 E:T ratio. (C) Recognition of Mo-DCs isolated from a healthy individual by thirteen MR1T cell clones with or without anti-MR1 mAbs (α-MR1). Graphs show IFN-γ release (mean±SD of duplicate cultures). (D) Recognition of Mo-DCs from three donors by the representative DGB129 MR1T cell clone in the absence or presence of anti-MR1 (α-MR1) mAbs. IFN-γ release in the supernatants is shown and expressed as mean±SD. (E) Flow cytometry analysis of co-stimulatory molecules CD83 and CD86 on Mo-DCs after co-culture with DGB129 MR1T cells with or without anti-MR1 mAbs (α-MR1). A control group consisting of Mo-DCs stimulated with LPS (10 ng/ml) in the absence of T cells is also shown. Numbers indicate percentages of cells in each quadrant. (F) Stimulation of JMAN MR1T cell clone by LS 174T and HCT116 gastrointestinal tumour cell lines and by normal gut epithelial cells (GEC) in the presence or not of anti-MR1 mAbs (α-MR1). Columns show IFN-γ release (mean±SD of duplicate cultures). All the results are representative of at least three independent experiments. * P<0.05 (Unpaired Student's t-test).

To assess the anti-tumour activity of MR1T cells the inventors tested their capacity to directly kill tumour cells in vitro. Two representative MR1T cell clones (DGB129 and DGB70) efficiently killed both MR1-expressing THP-1 and A375 cells at various effector:target ratios (FIG. 9A,B). A control MAIT cell clone failed to kill these two cell types, although it was fully capable of killing when targets were E. coli-infected (not shown). These results indicated that MR1T cells display specific cytotoxic activity against MR1-expressing tumour cells.

Having found that MR1 T cells recognized and killed the myelomonocytic tumour cell line THP-1, the inventors next addressed whether they could also recognize normal myeloid cells including monocytes and monocyte-derived dendritic cells (Mo-DC) from different donors. Monocytes were not recognized by any of the tested MR1T cell clones (not shown). By contrast, some MR1T cell clones reacted to Mo-DC in MR1 dependent manner (FIG. 9C). Interestingly, experiments performed with the representative DGB129 MR1T cell clone revealed that recognition of Mo-DC did not result in Mo-DC killing (not shown), but promoted up-regulation of CD83 and CD86 activation markers by Mo-DC (FIG. 9D). Remarkably, the activation of Mo-DC induced by DGB129 cells was fully inhibited by anti-MR1 mAbs (FIG. 9D). These data suggested that some tumour-reactive MR1T cells elicit direct anti-tumour activity and also promote activation of innate immune cells, with important implications in the establishment of effective anti-tumour immune responses.

As the inventors observed that some MR1T cell clones reacted to HCT116 and LS 174T intestinal tumour cells, they next investigated whether they could also recognize normal gut epithelial cells (GEC) prepared from gut biopsies. GEC cells were not stimulatory for any of the tested HCT116- or LS 174T-reactive MR1T cell clones (FIG. 9F,G), thus suggesting that MR1T cell clones may display specific recognition of gastrointestinal tumour cells while not reacting to normal intestinal epithelial cells.

To further assess the specificity of tumour recognition by MR1T cells, the inventors finally investigated whether they could react to other types of normal cells including neutrophils, NK cells, B cells and T cells. None of these cells were recognized by the tested MR1T cells (not shown).

Collectively, these data identify MR1T cells as a novel and heterogeneous population of human MR1-restricted T lymphocytes that i) differently react to various types of tumour cells, ii) display cytotoxic activity against tumour cells, iii) do not recognize normal cells with exception of in vitro-differentiated Mo-DC, and iv) do not kill Mo-DC but instead induce their activation. These findings suggested that MR1T cells display important anti-tumour properties and deserve to be exploited for their immunotherapeutic potential.

MR1T Cells are Functionally Heterogeneous

Figures 10A, 10B:
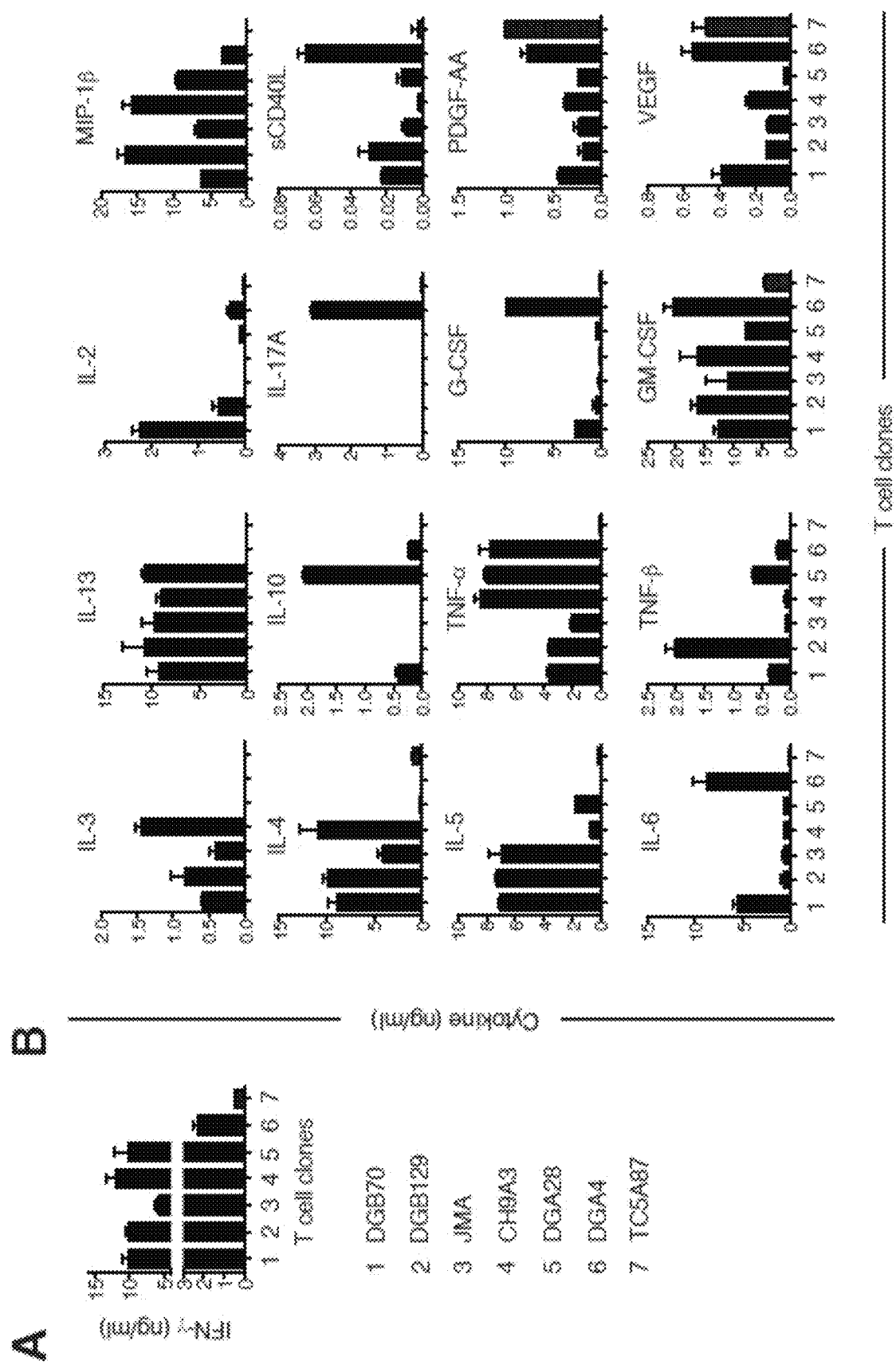
FIGS. 10A-10B. Functional heterogeneity of MR1T cell clones. (A) IFN-γ released by 7 selected MR1T cell clones stimulated with A375-MR1 cells. ELISA results are expressed as mean±SD of IFN-γ release measured in duplicate cultures. (B) Analysis of 16 additional cytokines by multiplex cytokine assay performed on the same supernatants for which IFN-γ is shown in A. Results are representative of two independent experiments.

The inventors finally analyzed the cytokine secretion profile of representative MR1T cell clones upon stimulation by A375-MR1 tumour cells. All clones tested released IFN-γ (FIG. 10A). However, the inventors also observed diverse expression profiles of Th1 (IL-2, TNF-α and TNF-β), Th2 (IL-3, IL-4, IL-5, IL-6, IL-10, IL-13) and Th17 cytokines (IL-17A, G-CSF, GM-CSF), and other soluble factors (MIP-1β, soluble CD40L PDGF-AA and VEGF; FIG. 10B). The variable combinations and quantities of cytokines expressed by MR1T cells suggested considerable functional plasticity within this population. For example, clone DGA4 secreted large quantities of IL-17A, IL-6, TNF-α and GM-CSF, but failed to secrete the prototypic Th2 cytokines IL-4, IL-5, IL-10 or IL-13, and thus displayed an 'atypical' Th17-like phenotype. In contrast, clone TC5A87 released substantial amounts of VEGF and PGDF-AA, but only little Th1 or Th2 cytokines, and no IL-17A. Notably, four of the seven clones studied (DGB129, CH9A3, DGB70, JMA) displayed a Th2-skewed profile of cytokine release, a functional phenotype which has been recently associated with protective anti-tumour immunity.

Figure 11:
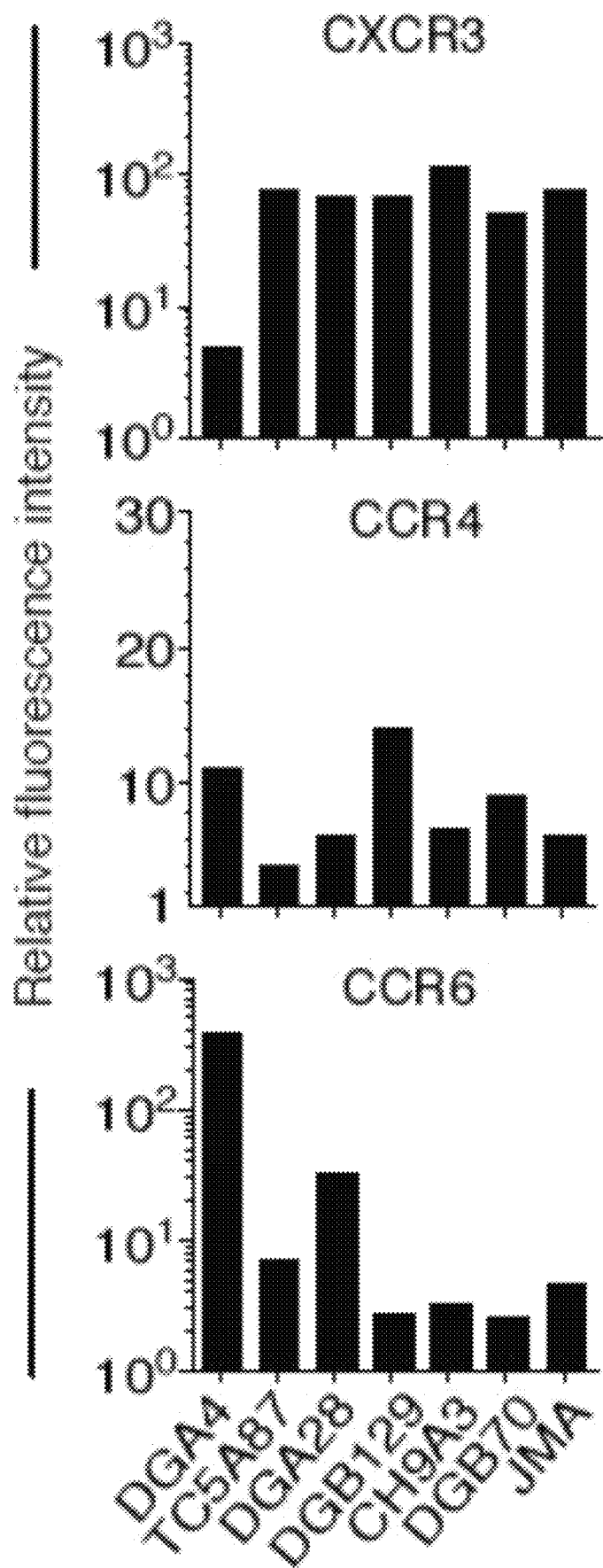
FIG. 11. MR1T cell clones display multiple chemokine-receptor expression profiles. Flow cytometry analysis of CXCR3, CCR4 and CCR6 surface expression by seven selected resting MR1T cell clones. Graphs show the relative fluorescence intensity calculated by dividing the median fluorescence intensity (MFI) of specific mAb staining by the MFI of the corresponding isotype control. Data are representative of two independent experiments.

The inventors next investigated the expression of three selected chemokine receptors known to be differentially expressed by T cell subsets with distinct functions and whose alternative combined expression regulates T cell recirculation and migration to diverse homing sites. All MR1T cell clones but DGA4 displayed high levels of CXCR3 (FIG. 11). In addition, the inventors observed divergent expression patterns of CCR4 and CCR6 (FIG. 11), which further suggested that MR1T cells are heterogeneous.

Figure 12:
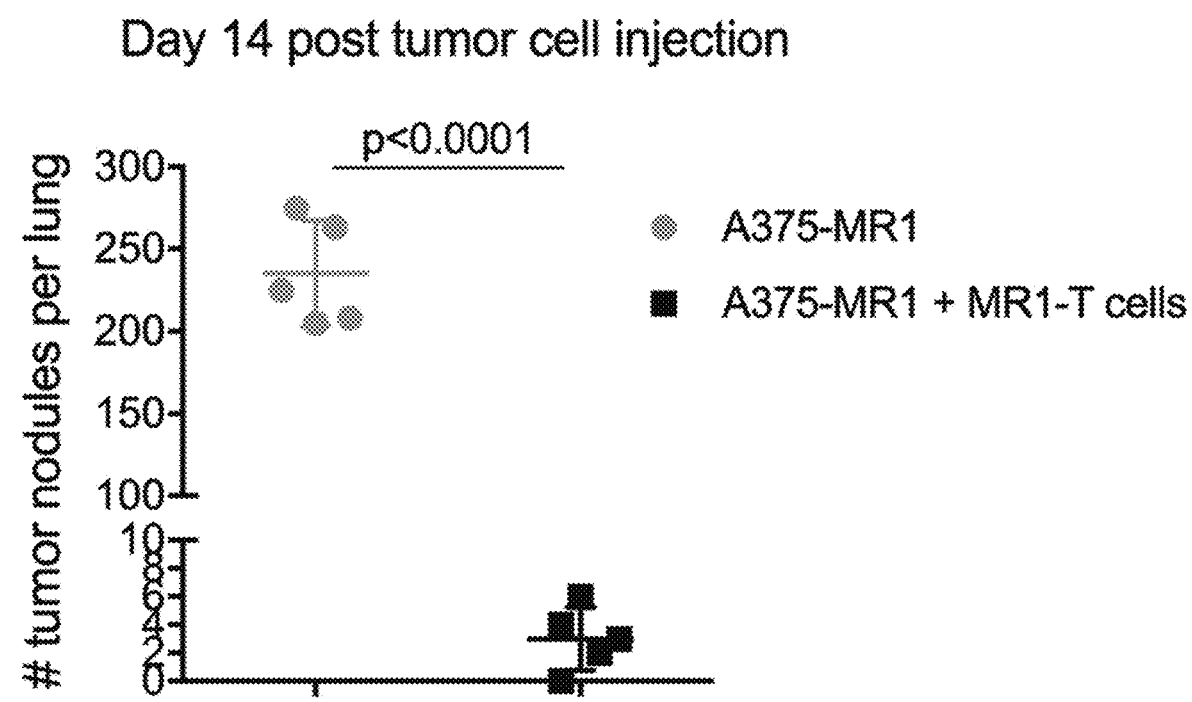
FIG. 12. MR1T cells reduce the number of human melanoma lung nodules in mice. Immunocompromised NSG mice were injected with the human melanoma A375 cells expressing MR1 (A375-MR1) and with MR1T cells. On day 14, mice were sacrificed and lung nodules were counted after India ink perfusion.

In a final series of studies it was investigated whether MR1T cells maintain their tumour-killing capacity in vivo using a lung solid tumour model. Mice intravenously injected with A375 melanoma cells expressing MR1 received DGB129 cells or were left untreated. On day 14, mice were sacrificed and the number of tumour nodules in the lungs was counted. While untreated mice showed 200-250 nodules, those treated with MR1T cells showed 1-6 nodules (FIG. 12). These results confirmed that in vivo growing tumour cells produce the antigens stimulating MR1T cells. Importantly, they provided strong evidence of the efficient capacity of MR1T cells to kill solid tumour cells in vivo.

Taken together, these data indicated that the tumour MR1-reactive T clones tested here are phenotypically and functionally diverse, thus suggesting that MR1T cells include multiple subsets with distinct recirculation patterns and tissue homing capacity and likely different roles in tumour immunity. In conclusion, these data identify MR1T cells as a novel population of human T lymphocytes that recognize MR1:tumour-associated-antigen complexes and may participate in anti-tumour immune responses with multiple effector functions.

TABLE 1

Phenotype of select MR1-reactive T cell clones.

| Clone | CD4 | CD8α | CD161 | TCRβ |
|---|---|---|---|---|
| DGB129 | − | + | − | TRBV12-4 |
| DGB70 | − | − | − | TRBV28 |
| DGA28 | − | + | + | TRBV29-1 |
| DGA4 | − | − | + | TRBV6-1 |
| JMA | − | + | − | TRBV25-1 |
| TC5A87 | − | + | − | TRBV25-1 |
| CH9A3 | − | + | − | TRBV5-5 |

TABLE 2

Tumour cell lines recognized by human MR1T cells.

| Cell line | Origin |
|---|---|
| A375 | Human melanoma |
| CCRF-SB | Human B lymphoblastic leukemia |
| Huh7 | Human hepatocellular carcinoma |
| HCT116 | Human colon carcinoma |
| LS 174T | Human colon adenocarcinoma |
| THP-1 | Human myelomonocytic leukemia |

The following examples further illustrate the clinical workflow in which the invention is applied:

Screening of MR1-Expressing Cancers

A cancer patient's tissue fresh or fresh-frozen tissue biopsies are analyzed for MR1 expression using mAbs specific for human MR1 and PCR amplification of MR1 mRNA.

Cancer Therapy, Example 1: Selection of Best MRT1 TCR Genes for Recognition of Primary MR1-Expressing Cancer Cells I. Primary MR1+ cancer cells isolated ex vivo are used to stimulate a library of previously characterized MR1T cell clones. Each clone expresses different TCR genes and recognizes different types of cancer cells.
II. The MR1T cells clones best responding to the cancer cells of the patient are selected and their TCR genes are used for TCR gene therapy. Response is assayed as a function of cytokine release and/or surface marker expression. Cells are assayed by internal (cytokine) or surface marker staining with antibodies reactive to the assayed activation markers, exemplified but not restricted to CD3, CD69, CD137, CD150, and/or ICOS (surface markers) and INF-γ and GM-CSF (cytokine).
III. When available soluble MR1T TCR will be multimerized and used to stain tumor cells isolated from tumour biopsies. The MR1T TCR multimers binding to tumour cells will allow rapid selection of MR1T TCRs suitable for gene therapy in that patient.
IV. Several circulating patient T cell populations may be used as recipient T cells (naïve, central memory, effector memory, CD4+, CD8+, or CD4, CD8 double negative T cells). Naïve T cells are selected to allow unprimed T lymphocytes to mature in the presence of tumor cells when they are transduced with TCR genes recognizing MR1-tumor antigens. Central and effector memory cells are used because they provide immediate proliferation and effector functions (tumor killing) upon recognition of tumor cells expressing MR1. CD4 cells are selected to provide sufficient numbers of T helper cells that facilitate recruitment and expansion of other cells with anti-tumor functions. CD8 T cells are selected to facilitate killing of tumor cells. CD4-CD8 double negative T cells are selected for their innate-like functions such as immediate release of large amounts of killer effector molecules (TNFα, granzymes and granulysin).

V. T cells expressing the transduced TCR genes and with selected effector functions are used for adoptive cell therapy (ACT).

T cells from peripheral blood of patients are stained with monoclonal antibodies specific for surface markers (CD4, CD8, CD27, CD45RA, CD57) and sorted. Each sorted population is activated with Dynabeads® Human T-Activator CD3/CD28 (ThermoFisher) and 24 h later transfected with the TCR genes encoding the MR1T TCR selected for the individual patient. This yields a modified T cell preparation (recipient T cells). In some cases, recipient T cells are also modified by gene-editing methods to inactivate PD1, ILT2 and ILT4 inhibitory genes or were transduced with CD137 and CD134 genes to promote cell survival, cell expansion and to enhance anti-cancer effector function. Lymphodepletion is made in recipient cancer patients using a non-myeloablative chemotherapy preparative regimen (60 mg/kg cyclophosphamide for 2 days and 25 mg/m$^2$ fludarabine administered for 5 days) followed by transfer of T cells and IL-2 given at 720,000 IU/kg to tolerance. In some instances, 200 or 1200 centigray (cGy; 1 Gy=100 rads) total-body irradiation is added to the preparative regimen. T cells expressing the MR1T exogenous TCR genes (the modified T cell preparation) are transferred into recipient. TCR genes are cloned in safe recombinant lentivirus vectors (see for example Provasi et al., *Nat Med* 18, 807-815 (2012)), which contain suicide genes and cannot produce mature viral particles in the absence of other helper viruses. In some cases, TCR genes are cloned in vectors containing suicide genes (for examples, see Greco et al., *Front Pharmacol* 6, 95 (2015)), thus reducing the risks derived from unwanted gene insertion. In some cases RNA encoding the TCR MR1T genes is transfected in recipient cells (see for example Zhao et al. *Molecular therapy* 13, 151, 2006)).

Cancer Therapy, Example 2: Isolation of MR1T Cells from Tumor-Infiltrating Lymphocytes (TILs) of Patient to be Treated VI. Autologous TILs are prepared from the cancer tissue biopsies according to our previously established protocol (De Libero, ibid.).

VII. T cells are expanded in vitro for 2-3 weeks using medium supplemented with IL-2, IL-7, and IL-15.

VIII. Expanded T cells are tested for reactivity against autologous MR1$^+$ cancer cells. T cells that increase surface expression of activation markers (CD137, CD150, CD69, ICOS) are considered cancer-specific and if they are inhibited by the presence of anti-MR1 monoclonal antibodies, they are considered MR1-dependent.

Cancer-reactive T cells are sorted according to the expression of one of above activation markers and expanded and used for ACT, as outlined above.

TABLE designation of sequence ID NOs

| | Protein | | | | Nucleic acid | |
|---|---|---|---|---|---|---|
| Clone | α | β | α CDR3 | β CDR3 | α | β |
| 1 | 1 | 2 | 65 | 80 | 7 | 8 |
| 2 | 3 | 4 | 66 | 81 | 9 | 10 |
| 3 | 5 | 6 | 67 | 82 | 11 | 12 |
| 4 | 13 | 25 | 68 | 83 | 37 | 49 |
| 5 | 14 | 26 | 69 | 84 | 38 | 50 |
| 6 | 15 | 27 | 70 | 85 | 39 | 51 |
| 7 | 16 | 28 | 71 | 86 | 40 | 52 |
| 8 | 17 | 29 | 72 | 87 | 41 | 53 |
| 9 | 18 | 30 | 73 | 88 | 42 | 54 |
| 10 | 19 | 31 | 74 | 89 | 43 | 55 |
| 11 | 20 | 32 | 75 | 90 | 44 | 56 |
| 12 | 21 | 33 | 76 | 91 | 45 | 57 |
| 13 | 22 | 34 | 77 | 92 | 46 | 58 |
| 14 | 23 | 35 | 78 | 93 | 47 | 59 |
| 15 | 24 | 36 | 79 | 94 | 48 | 60 |
| Clone | γ | δ | γCDR3 | δ CDR3 | γ | δ |
| (1) | 61 | 62 | 95 | 96 | 63 | 64 |

We claim:

1. A method of isolating a T cell that expresses a T cell receptor capable of binding specifically to an antigen presented by a cancer cell in association with an MR1 molecule, said method comprising the steps of
   a. providing a preparation of T cells, then
   b. contacting said preparation of T cells with a cancer cell expressing MR1 in a contacting step, then
   c. isolating a T cell that is specifically reactive to said cancer cell in an isolation step.

2. The method according to claim 1, wherein said contacting step comprises an expansion step, wherein said preparation of isolated T cells is expanded in the presence of a cancer cell expressing MR1.

3. The method according to claim 1, wherein said expansion step is conducted in the presence of IL-2, and/or IL-7 and/or IL-15.

4. The method according to claim 1, wherein said isolation step comprises staining the T cell preparation with a ligand specific for a cell surface marker selected from CD3, CD69, CD137, CD150, and/or ICOS, followed by flow cytometric analysis and cell sorting by using FACS or magnetic separation.

5. The method according to claim 4, wherein said ligand specific for a cell surface marker is an antibody or antibody-like molecule.

6. The method according to claim 1, wherein said isolating step comprises selecting T cells that exhibit 2× increased expression of a cytokine selected from IFN-γ and/or GM-CSF release when stimulated with cells expressing MR1, compared to stimulation with cells not expressing MR1.

7. The method according to claim 1, further including determining a nucleic acid sequence encoding a T cell receptor of the T cell isolated in the isolation step.

8. A method of preparing a preparation of MR1T cells that express a T cell receptor capable of binding to an MR1 molecule expressed on a tumour cell that presents a tumour associated antigen, comprising the steps of
   a. providing a tumour sample obtained from a patient;
   b. contacting said tumour sample with
      i. a plurality of T cell clones, wherein each T cell clone is characterized by an MR1T cell receptor capable of binding specifically to an MRI molecule in association with a tumour associated antigen; or
      ii. a plurality of labelled and multimerized soluble T cell receptors molecules capable of binding specifically to an MR1 molecule in association with a tumour associated antigen;
   c. identifying an MR1T cell receptor or T cell receptor molecule specifically reactive to said tumour sample;
   d. providing a T cell preparation;
   e. introducing into said T cell preparation a nucleic acid expression construct encoding said MR1 T cell receptor identified as being specifically reactive to said tumour sample, or said T cell receptor molecule identified as being specifically reactive to said tumour sample in step c., yielding a trans gene T cell preparation.

9. The method according to claim 8, wherein each of said T cell clones or each of said isolated, labelled and multimerized soluble T cell receptors is characterized by
   a T cell receptor αchain nucleic acid sequence selected from SEQ ID NO 007, 009 to 011 or SEQ ID NO 037 to SEQ ID NO 048 and/or an amino acid sequence selected from SEQ ID NO 001, 003 to 005 or SEQ ID NO 013 to SEQ ID NO 024; comprising a CDR sequence selected from SEQ ID NO 065 to SEQ ID NO 079 and
   a T cell receptor β chain nucleic acid sequence selected from SEQ ID NO 008, 010 to 012 or SEQ ID NO 049 to SEQ ID NO 060 and/or an amino acid sequence selected from SEQ ID NO 002, 004 to 006 or SEQ ID NO 025 to SEQ ID NO 036 comprising a CDR sequence selected from SEQ ID NO 080 to SEQ ID NO 094; or
   wherein each of said T cell clones or said isolated, labelled and multimerized soluble T cell receptors is characterized by a T cell receptor α chain and β chain nucleic acid sequence pair selected from the pairs:
   SEQ ID NO 007 and SEQ ID NO 008; or SEQ ID NO 009 and SEQ ID NO 010;

or SEQ ID NO 011 and SEQ ID NO 012; or SEQ ID NO 037 and SEQ ID NO 037 and SEQ ID NO 049; or SEQ ID NO 038 and SEQ ID NO 050; or SEQ ID NO 039 and SEQ ID NO 051; or SEQ ID NO 040 and SEQ ID NO 052; or SEQ ID NO 041 and SEQ ID NO 053; or SEQ ID NO 042 and SEQ ID NO 054; or SEQ ID NO 043 and SEQ ID NO 055; or SEQ ID NO 044 and SEQ ID NO 056; or SEQ ID NO 045 and SEQ ID NO 057; or SEQ ID NO 046 and SEQ ID NO 058; or SEQ ID NO 047 and SEQ ID NO 059; or SEQ ID NO 048 and SEQ ID NO 060; or wherein each of said T cell clones or said isolated, labelled and multimerized soluble T cell receptors is characterized by a T cell receptor α chain and β chain amino acid sequence pair selected from:

SEQ ID NO 001 and SEQ ID NO 002; or, SEQ ID NO 003 and SEQ ID NO 004;

or SEQ ID NO 005 and SEQ ID NO 006; or SEQ ID NO 013 and SEQ ID NO 025; or SEQ ID NO 014 and SEQ ID NO 026; or SEQ ID NO 015 and SEQ ID NO 027; or SEQ ID NO 016 and SEQ ID NO 028; or SEQ ID NO 017 and SEQ ID NO 029; or SEQ ID NO 018 and SEQ ID NO 030; or SEQ ID NO 019 and SEQ ID NO 031; or SEQ ID NO 20 and SEQ ID NO 032; or SEQ ID NO 021 and SEQ ID NO 033; or SEQ ID NO 022 and SEQ ID NO 034; or SEQ ID NO 023 and SEQ ID NO 035; or SEQ ID NO 024 and SEQ ID NO 036.

10. The method according to claim 8, wherein said T cell preparation is obtained from the same patient (autologous adoptive T cell therapy), or wherein said T cell preparation is obtained from another subject (allogeneic adoptive T cell therapy).

11. The method according to claim 8, wherein said T cell preparation obtained from said patient is obtained from peripheral blood of the patient, wherein said T cell preparation is obtained by selecting PBMC for expression of one or several T cell markers selected from the group containing CD4, CD8, CD27, CD45RA, CD57, $CD3^+$ $CD4^+$, or $CD3^+$ $CD8^+$, or $CD3^+$ $CD27^+$ $CD45RA^+$, or $CD3^+$ $CD27^+$ $CD45RA^-$, or $CD3^+$ $CD27^-$ $CD45RA^-$, or $CD3^+$ $CD57^-$ or $CD3^+$ $CD57^+$ T cells.

12. The method according to claim 8, wherein said T cell preparation obtained from said patient is obtained from a tumour biopsy followed by subsequent expansion in-vitro.

13. The method according to claim 8, wherein said MR1-reactive T cell receptor identified as being specifically reactive to said tumour sample is a T cell receptor protein heterodimer comprising a TCR α chain amino acid sequence and a TCR β chain amino acid sequence, wherein said α and β sequences are selected from SEQ ID NOs: 1-6 and SEQ ID NOs: 13-36, and wherein the selected sequences comprise CDR3 sequences selected from SEQ ID NOs: 65-96.

14. The method according to claim 13, wherein said T cell receptor protein comprises a pair of amino acid sequence selected from SEQ ID NO 001 and SEQ ID NO 002; or SEQ ID NO 003 and SEQ ID NO 004; or SEQ ID NO 005 and SEQ ID NO 006, SEQ ID NO 013 and SEQ ID NO 025; or SEQ ID NO 014 and SEQ ID NO 026; or SEQ ID NO 015 and SEQ ID NO 027; or SEQ ID NO 016 and SEQ ID NO 028; or SEQ ID NO 017 and SEQ ID NO 029; or SEQ ID NO 018 and SEQ ID NO 030; or SEQ ID NO 019 and SEQ ID NO 031; or SEQ ID NO 20 and SEQ ID NO 032; or SEQ ID NO 021 and SEQ ID NO 033; or SEQ ID NO 022 and SEQ ID NO 034; or SEQ ID NO 023 and SEQ ID NO 035; or SEQ ID NO 024 and SEQ ID NO 036.

15. The method according to claim 13, wherein the isolated T cell receptor protein heterodimer that binds to an MR1 molecule binds to a MR1 molecule presenting a tumour-associated antigen.

16. The method according to claim 4, wherein said isolation step comprises a cell surface marker selecting from the group consisting of $CD3^+$ $CD137^+$, and/or $CD3^+$ $CD69^+$, and/or $CD3^+$ $CD150^+$, and/or $CD3^+$ $ICOS^+$ T cells.

* * * * *